US011674176B2

(12) United States Patent
Stoughton et al.

(10) Patent No.: US 11,674,176 B2
(45) Date of Patent: *Jun. 13, 2023

(54) FETAL ANEUPLOIDY DETECTION BY SEQUENCING

(71) Applicants: Verinata Health, Inc., Redwood City, CA (US); The General Hospital Corporation, Boston, MA (US); GPB Scientific, LLC, Richmond, VA (US)

(72) Inventors: Roland Stoughton, The Sea Ranch, CA (US); Ravi Kapur, Sharon, MA (US); Barb Ariel Cohen, Watertown, MA (US); Mehmet Toner, Charlestown, MA (US)

(73) Assignees: Verinata Health, Inc, Redwood City, CA (US); The General Hospital Corporation, Boston, MA (US); GPB Scientific, LLC, Richmond, VA (US)

(*) Notice: Subject to any disclaimer, the term of this patent is extended or adjusted under 35 U.S.C. 154(b) by 109 days.

This patent is subject to a terminal disclaimer.

(21) Appl. No.: 16/917,185

(22) Filed: Jun. 30, 2020

(65) Prior Publication Data

US 2021/0087624 A1 Mar. 25, 2021

Related U.S. Application Data

(63) Continuation of application No. 13/794,503, filed on Mar. 11, 2013, now Pat. No. 10,704,090, which is a continuation of application No. 12/751,940, filed on Mar. 31, 2010, now abandoned, which is a continuation of application No. 11/763,133, filed on Jun. 14, 2007, now abandoned.

(60) Provisional application No. 60/820,778, filed on Jul. 28, 2006, provisional application No. 60/804,816, filed on Jun. 14, 2006.

(51) Int. Cl.
*C12Q 1/6874* (2018.01)
*C12Q 1/6883* (2018.01)

(52) U.S. Cl.
CPC ......... *C12Q 1/6874* (2013.01); *C12Q 1/6883* (2013.01); *C12Q 2600/156* (2013.01)

(58) Field of Classification Search
CPC ................ C12Q 1/6874; C12Q 1/6883; C12Q 2600/156
See application file for complete search history.

(56) References Cited

U.S. PATENT DOCUMENTS

| 4,508,625 A | 9/1985 | Graham |
| 4,675,286 A | 6/1987 | Calenoff |
| 4,683,202 A | 7/1987 | Mullis |
| 4,789,628 A | 12/1988 | Nayak |
| 4,800,159 A | 1/1989 | Mullis et al. |
| 4,971,904 A | 11/1990 | Luddy |
| 4,977,078 A | 12/1990 | Niimura et al. |
| 5,153,117 A | 10/1992 | Simons |
| 5,215,926 A | 6/1993 | Etchells, III et al. |
| 5,296,375 A | 3/1994 | Kricka et al. |
| 5,300,779 A | 4/1994 | Hillman et al. |
| 5,302,509 A | 4/1994 | Cheeseman |
| 5,304,487 A | 4/1994 | Wilding et al. |
| 5,427,663 A | 6/1995 | Atin et al. |
| 5,427,946 A | 6/1995 | Kricka et al. |
| 5,432,054 A | 7/1995 | Saunders et al. |
| 5,447,842 A | 9/1995 | Simons |
| 5,486,335 A | 1/1996 | Wilding et al. |
| 5,498,392 A | 3/1996 | Wilding et al. |
| 5,508,169 A | 4/1996 | Deugau et al. |
| 5,529,903 A | 6/1996 | Kubler et al. |
| 5,556,773 A | 9/1996 | Youmo |
| 5,639,669 A | 6/1997 | Ledley |
| 5,641,628 A | 6/1997 | Bianchi |
| 5,646,001 A | 7/1997 | Terstappen et al. |
| 5,670,325 A | 9/1997 | Lapid et al. |
| 5,676,849 A | 10/1997 | Sammons et al. |
| 5,695,934 A | 12/1997 | Brenner |
| 5,707,799 A | 1/1998 | Hansmann et al. |
| 5,709,943 A | 1/1998 | Coleman et al. |
| 5,715,946 A | 2/1998 | Reichenbach |
| 5,726,026 A | 3/1998 | Wilding et al. |
| 5,750,339 A | 5/1998 | Smith |
| 5,766,843 A | 6/1998 | Asgari et al. |
| 5,770,029 A | 6/1998 | Nelson et al. |
| 5,798,042 A | 8/1998 | Chu et al. |
| 5,837,115 A | 11/1998 | Atin et al. |
| 5,840,502 A | 11/1998 | Van Vlasselaer |
| 5,842,787 A | 12/1998 | Koph-Sill et al. |
| 5,858,649 A | 1/1999 | Asgari et al. |
| 5,866,345 A | 2/1999 | Wilding et al. |
| 5,879,883 A | 3/1999 | Benson et al. |
| 5,891,651 A | 4/1999 | Roche et al. |

(Continued)

FOREIGN PATENT DOCUMENTS

| AU | 2007260676 A1 | 12/2007 |
| CA | 2655272 A1 | 12/2007 |

(Continued)

OTHER PUBLICATIONS

U.S. Appl. No. 11/825,677, filed Jul. 5, 2007, Lopez et al.
U.S. Appl. No. 11/909,959, filed Sep. 27, 2007, Duff.
U.S. Appl. No. 14/705,239, filed May 6, 2015, Kapur et al.
U.S. Appl. No. 60/764,420, filed Feb. 2, 2005, Quake.
U.S. Appl. No. 60/949,227, filed Jul. 11, 2007, Kapur.
U.S. Appl. No. 60/951,438, filed Jul. 23, 2007, Lo et al.
Adams, et al. Complementary DNA Sequencing: Expressed Sequence Tags and Human Genome Project. Science Jun. 21, 1991: vol. 252 No. 5013 pp. 1651-1656 DOI: 10.1126/science.2047873.

(Continued)

*Primary Examiner* — Teresa E Strzelecka
(74) *Attorney, Agent, or Firm* — Fish & Richardson P.C.

(57) ABSTRACT

The present invention provides apparatus and methods for enriching components or cells from a sample and conducting genetic analysis, such as SNP genotyping to provide diagnostic results for fetal disorders or conditions.

11 Claims, 21 Drawing Sheets

(56) References Cited

U.S. PATENT DOCUMENTS

| | | |
|---|---|---|
| 5,928,880 A | 7/1999 | Wilding et al. |
| 5,952,173 A | 9/1999 | Hansmann et al. |
| 5,962,234 A | 10/1999 | Golb |
| 5,962,237 A | 10/1999 | Ts'o et al. |
| 5,962,332 A | 10/1999 | Singer et al. |
| 5,972,721 A | 10/1999 | Bruno et al. |
| 5,993,665 A | 11/1999 | Terstappen et al. |
| 5,994,057 A | 11/1999 | Mansfield |
| 5,994,517 A | 11/1999 | Ts'o et al. |
| 6,007,690 A | 12/1999 | Nelson et al. |
| 6,008,007 A | 12/1999 | Fruehauf et al. |
| 6,013,188 A | 1/2000 | Terstappen et al. |
| 6,027,923 A | 2/2000 | Wallace |
| 6,066,449 A | 5/2000 | Ditkoff et al. |
| 6,074,827 A | 6/2000 | Nelson et al. |
| 6,100,029 A | 8/2000 | Lapid et al. |
| 6,124,120 A | 9/2000 | Lizardi |
| 6,159,685 A | 10/2000 | Pinkel et al. |
| 6,143,496 A | 11/2000 | Brown et al. |
| 6,143,576 A | 11/2000 | Buechler |
| 6,154,707 A | 11/2000 | Livak et al. |
| 6,156,270 A | 12/2000 | Buechler |
| 6,176,962 B1 | 1/2001 | Soane et al. |
| 6,184,029 B1 | 2/2001 | Wilding et al. |
| 6,184,043 B1 | 2/2001 | Fodstad et al. |
| 6,186,660 B1 | 2/2001 | Koph-Sill et al. |
| 6,190,870 B1 | 2/2001 | Schmitz et al. |
| 6,197,523 B1 | 3/2001 | Rimm et al. |
| 6,200,765 B1 | 3/2001 | Murphy et al. |
| 6,210,891 B1 | 4/2001 | Nyren et al. |
| 6,214,558 B1 | 4/2001 | Shuber et al. |
| 6,235,474 B1 | 5/2001 | Feinberg |
| 6,258,540 B1 | 7/2001 | Lo et al. |
| 6,265,229 B1 | 7/2001 | Fodstad et al. |
| 6,300,077 B1 | 10/2001 | Shuber et al. |
| 6,329,150 B1 | 12/2001 | Lizardi et al. |
| 6,344,326 B1 | 2/2002 | Nelson et al. |
| 6,361,958 B1 | 3/2002 | Shieh et al. |
| 6,368,871 B1 | 4/2002 | Christel et al. |
| 6,376,181 B2 | 4/2002 | Ramsey et al. |
| 6,383,759 B1 | 5/2002 | Murphy et al. |
| 6,387,707 B1 | 5/2002 | Seul et al. |
| 6,391,559 B1 | 5/2002 | Brown et al. |
| 6,394,942 B2 | 5/2002 | Moon et al. |
| 6,399,364 B1 | 6/2002 | Reeve et al. |
| 6,432,630 B1 | 8/2002 | Blankenstein |
| 6,440,706 B1 | 8/2002 | Vogelstein et al. |
| 6,444,461 B1 | 9/2002 | Knapp et al. |
| 6,454,938 B2 | 9/2002 | Moon et al. |
| 6,479,299 B1 | 11/2002 | Paree et al. |
| 6,511,967 B1 | 1/2003 | Weissleder et al. |
| 6,517,234 B1 | 2/2003 | Koph-Sill et al. |
| 6,540,895 B1 | 4/2003 | Spence et al. |
| 6,566,101 B1 | 5/2003 | Shuber et al. |
| 6,576,478 B1 | 6/2003 | Wagner et al. |
| 6,582,904 B2 | 6/2003 | Dahm |
| 6,582,969 B1 | 6/2003 | Wagner et al. |
| 6,596,144 B1 | 7/2003 | Regnier et al. |
| 6,596,545 B1 | 7/2003 | Wagner et al. |
| 6,613,525 B2 | 9/2003 | Nelson et al. |
| 6,618,679 B2 | 9/2003 | Loehriein et al. |
| 6,632,619 B1 | 10/2003 | Harrison et al. |
| 6,632,652 B1 | 10/2003 | Atin et al. |
| 6,632,655 B1 | 10/2003 | Mehta et al. |
| 6,637,463 B1 | 10/2003 | Lei et al. |
| 6,645,731 B2 | 11/2003 | Terstappen et al. |
| 6,664,056 B2 | 12/2003 | Lo et al. |
| 6,664,104 B2 | 12/2003 | Pourahmadi et al. |
| 6,673,541 B1 | 1/2004 | Klein et al. |
| 6,674,525 B2 | 1/2004 | Bardell et al. |
| 6,685,841 B2 | 2/2004 | Lopez et al. |
| 6,689,615 B1 | 2/2004 | Murto et al. |
| 6,746,503 B1 | 6/2004 | Benett et al. |
| 6,753,147 B2 | 6/2004 | Vogelstein et al. |
| 6,783,928 B2 | 8/2004 | Hvichia et al. |
| 6,818,184 B2 | 11/2004 | Fulwyler et al. |
| 6,830,936 B2 | 12/2004 | Anderson et al. |
| 6,858,439 B1 | 2/2005 | Xu et al. |
| 6,875,619 B2 | 4/2005 | Blackburn |
| 6,893,881 B1 | 5/2005 | Fodstad et al. |
| 6,906,182 B2 | 6/2005 | Ts'o et al. |
| 6,911,345 B2 | 6/2005 | Quake et al. |
| 6,913,697 B2 | 7/2005 | Lopez et al. |
| 6,927,028 B2 | 8/2005 | Lo et al. |
| 6,953,668 B1 | 10/2005 | Israeli et al. |
| 6,960,449 B2 | 11/2005 | Wang et al. |
| 7,115,709 B1 | 10/2006 | Gray et al. |
| 7,150,812 B2 | 12/2006 | Huang et al. |
| 7,171,975 B2 | 2/2007 | Moon et al. |
| 7,190,818 B2 | 3/2007 | Ellis et al. |
| 7,192,698 B1 | 3/2007 | Kinch et al. |
| 7,198,787 B2 | 4/2007 | Fodstad et al. |
| 7,208,275 B2 | 4/2007 | Goeke et al. |
| 7,208,295 B2 | 4/2007 | Faham et al. |
| 7,212,660 B2 | 5/2007 | Wetzel et al. |
| 7,220,594 B2 | 5/2007 | Foster et al. |
| 7,227,002 B1 | 6/2007 | Kufer et al. |
| 7,229,838 B2 | 6/2007 | Foster et al. |
| 7,250,256 B2 | 7/2007 | Reinhard et al. |
| 7,252,976 B2 | 8/2007 | Lin et al. |
| 7,258,987 B2 | 8/2007 | Lamorte et al. |
| 7,262,177 B2 | 8/2007 | Ts'o et al. |
| 7,262,269 B2 | 8/2007 | Lam et al. |
| 7,264,972 B2 | 9/2007 | Foster |
| 7,272,252 B2 | 9/2007 | De La Torre-Bueno et al. |
| 7,276,170 B2 | 10/2007 | Oakey et al. |
| 7,332,277 B2 | 2/2008 | Dhallan |
| 7,407,757 B2 | 8/2008 | Brenner |
| 7,442,506 B2 | 10/2008 | Dhallan |
| 7,476,363 B2 | 1/2009 | Unger et al. |
| 7,582,420 B2 | 9/2009 | Oliphant et al. |
| 7,645,576 B2 | 1/2010 | Lo et al. |
| 7,655,399 B2 | 2/2010 | Cantor et al. |
| 7,709,194 B2 | 5/2010 | Lo et al. |
| 7,718,367 B2 | 5/2010 | Lo et al. |
| 7,727,720 B2 | 6/2010 | Dhallan et al. |
| 7,754,428 B2 | 7/2010 | Lo et al. |
| 7,799,531 B2 | 9/2010 | Mitchell et al. |
| 7,838,647 B2 | 11/2010 | Hahn et al. |
| 7,888,017 B2 | 2/2011 | Quake et al. |
| RE42,315 E | 5/2011 | Lopez et al. |
| 7,955,794 B2 | 6/2011 | Shen et al. |
| 8,003,354 B2 | 8/2011 | Shen et al. |
| 8,008,018 B2 | 8/2011 | Quake et al. |
| 8,024,128 B2 | 9/2011 | Rabinowitz et al. |
| 8,137,912 B2 | 3/2012 | Kapur et al. |
| 8,168,389 B2 | 5/2012 | Shoemaker et al. |
| 8,195,415 B2 | 6/2012 | Fan et al. |
| 8,293,470 B2 | 10/2012 | Quake et al. |
| 8,296,076 B2 | 10/2012 | Fan et al. |
| 8,318,430 B2 | 11/2012 | Chuu et al. |
| 8,372,584 B2 | 2/2013 | Shoemaker et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 9,017,942 B2 | 4/2015 | Shoemaker et al. |
| 9,347,100 B2 | 5/2016 | Shoemaker et al. |
| 2001/0007749 A1 | 7/2001 | Feinberg |
| 2001/0051341 A1 | 12/2001 | Lo et al. |
| 2001/0053958 A1 | 12/2001 | Ried et al. |
| 2002/0006621 A1 | 1/2002 | Bianchi |
| 2002/0009738 A1 | 1/2002 | Houghton et al. |
| 2002/0012930 A1 | 1/2002 | Rothberg et al. |
| 2002/0012931 A1 | 1/2002 | Waldman et al. |
| 2002/0016450 A1 | 2/2002 | Laugham et al. |
| 2002/0019001 A1 | 2/2002 | Light |
| 2002/0028431 A1 | 3/2002 | Julien |
| 2002/0058332 A1 | 5/2002 | Quake et al. |
| 2002/0076825 A1 | 6/2002 | Cheng et al. |
| 2002/0086329 A1 | 7/2002 | Shvets et al. |
| 2002/0110835 A1 | 8/2002 | Kumar |
| 2002/0119469 A1 | 8/2002 | Shuber et al. |
| 2002/0123078 A1 | 9/2002 | Seul et al. |
| 2002/0127575 A1 | 9/2002 | Hoke et al. |

(56) References Cited

U.S. PATENT DOCUMENTS

| | | |
|---|---|---|
| 2002/0137088 A1 | 9/2002 | Bianchi |
| 2002/0164816 A1 | 11/2002 | Quake |
| 2002/0166760 A1 | 11/2002 | Prentiss et al. |
| 2002/0172987 A1 | 11/2002 | Terstappen et al. |
| 2003/0004402 A1 | 1/2003 | Hitt et al. |
| 2003/0013101 A1 | 1/2003 | Balasubramanian |
| 2003/0017514 A1 | 1/2003 | Pachmann et al. |
| 2003/0022207 A1 | 1/2003 | Balasubramanian |
| 2003/0033091 A1 | 2/2003 | Opalsky et al. |
| 2003/0044388 A1 | 3/2003 | Lo et al. |
| 2003/0044781 A1 | 3/2003 | Korlach et al. |
| 2003/0072682 A1 | 4/2003 | Kikinis |
| 2003/0077292 A1 | 4/2003 | Hanash et al. |
| 2003/0082566 A1 | 5/2003 | Sylvan |
| 2003/0100102 A1 | 5/2003 | Rothberg et al. |
| 2003/0119077 A1 | 6/2003 | Ts'o et al. |
| 2003/0119724 A1 | 6/2003 | Ts'o et al. |
| 2003/0129676 A1 | 7/2003 | Terstappen et al. |
| 2003/0152981 A1 | 8/2003 | Hulten |
| 2003/0153085 A1 | 8/2003 | Leary et al. |
| 2003/0159999 A1 | 8/2003 | Oakey et al. |
| 2003/0165852 A1 | 9/2003 | Schueler et al. |
| 2003/0170631 A1 | 9/2003 | Houghton et al. |
| 2003/0170703 A1 | 9/2003 | Piper et al. |
| 2003/0175990 A1 | 9/2003 | Heyenga |
| 2003/0186255 A1 | 10/2003 | Williams et al. |
| 2003/0190602 A1 | 10/2003 | Pressman et al. |
| 2003/0199685 A1 | 10/2003 | Pressman et al. |
| 2003/0204331 A1 | 10/2003 | Whitney et al. |
| 2003/0206901 A1 | 11/2003 | Chen |
| 2003/0219765 A1 | 11/2003 | Costa |
| 2003/0231791 A1 | 12/2003 | Torre-Bueno et al. |
| 2003/0232350 A1 | 12/2003 | Afar et al. |
| 2004/0005582 A1 | 1/2004 | Shipwash |
| 2004/0009471 A1 | 1/2004 | Cao |
| 2004/0018116 A1 | 1/2004 | Desmond et al. |
| 2004/0018509 A1 | 1/2004 | Bianchi |
| 2004/0043506 A1 | 3/2004 | Hasecker et al. |
| 2004/0048360 A1 | 3/2004 | Wada et al. |
| 2004/0053352 A1 | 3/2004 | Ouyang et al. |
| 2004/0072278 A1 | 4/2004 | Chou et al. |
| 2004/0096892 A1 | 5/2004 | Wang et al. |
| 2004/0137452 A1 | 7/2004 | Levett et al. |
| 2004/0137470 A1 | 7/2004 | Dhallan |
| 2004/0142463 A1 | 7/2004 | Walker et al. |
| 2004/0144651 A1 | 7/2004 | Huang et al. |
| 2004/0157243 A1 | 8/2004 | Huang et al. |
| 2004/0166555 A1 | 8/2004 | Braff et al. |
| 2004/0171091 A1 | 9/2004 | Lesko et al. |
| 2004/0185495 A1 | 9/2004 | Schueler et al. |
| 2004/0203037 A1 | 10/2004 | Lo et al. |
| 2004/0209299 A1 | 10/2004 | Pinter et al. |
| 2004/0214240 A1 | 10/2004 | Cao |
| 2004/0232074 A1 | 11/2004 | Peters et al. |
| 2004/0241707 A1 | 12/2004 | Gao et al. |
| 2005/0014208 A1 | 1/2005 | Krehan et al. |
| 2005/0019792 A1 | 1/2005 | McBride et al. |
| 2005/0037388 A1 | 2/2005 | Antonarakis et al. |
| 2005/0042623 A1 | 2/2005 | Ault-Riche et al. |
| 2005/0042685 A1 | 2/2005 | Albert et al. |
| 2005/0049793 A1 | 3/2005 | Paterlini-Brechot |
| 2005/0061962 A1 | 3/2005 | Mueth et al. |
| 2005/0064476 A1 | 3/2005 | Huang et al. |
| 2005/0095606 A1 | 5/2005 | Hoke et al. |
| 2005/0100932 A1 | 5/2005 | Lapid et al. |
| 2005/0118591 A1 | 6/2005 | Tamak et al. |
| 2005/0129581 A1 | 6/2005 | McBride et al. |
| 2005/0130217 A1 | 6/2005 | Huang et al. |
| 2005/0145496 A1 | 7/2005 | Goodsaid et al. |
| 2005/0147977 A1 | 7/2005 | Koo et al. |
| 2005/0153342 A1 | 7/2005 | Chen |
| 2005/0158754 A1 | 7/2005 | Puffenberger et al. |
| 2005/0164241 A1 | 7/2005 | Hahn et al. |
| 2005/0175996 A1 | 8/2005 | Chen |
| 2005/0181353 A1 | 8/2005 | Rao et al. |
| 2005/0181463 A1 | 8/2005 | Rao et al. |
| 2005/0196785 A1 | 9/2005 | Quake et al. |
| 2005/0207940 A1 | 9/2005 | Butler et al. |
| 2005/0211556 A1 | 9/2005 | Childers et al. |
| 2005/0214855 A1 | 9/2005 | Wagner et al. |
| 2005/0221341 A1 | 10/2005 | Shimkets et al. |
| 2005/0221373 A1 | 10/2005 | Enzelberger et al. |
| 2005/0239101 A1 | 10/2005 | Sukumar et al. |
| 2005/0244843 A1 | 11/2005 | Chen et al. |
| 2005/0250111 A1 | 11/2005 | Xie et al. |
| 2005/0250147 A1 | 11/2005 | Macevicz |
| 2005/0250155 A1 | 11/2005 | Lesko et al. |
| 2005/0250199 A1 | 11/2005 | Anderson et al. |
| 2005/0252773 A1 | 11/2005 | McBride et al. |
| 2005/0255001 A1 | 11/2005 | Padmanabhan et al. |
| 2005/0262577 A1 | 11/2005 | Guelly et al. |
| 2005/0266417 A1 | 12/2005 | Barany et al. |
| 2005/0266433 A1 | 12/2005 | Kapur et al. |
| 2005/0272103 A1 | 12/2005 | Chen |
| 2005/0282196 A1 | 12/2005 | Costa |
| 2005/0282293 A1 | 12/2005 | Cosmen et al. |
| 2005/0287611 A1 | 12/2005 | Nugent et al. |
| 2006/0000772 A1 | 1/2006 | Sano et al. |
| 2006/0008807 A1 | 1/2006 | O'Hara et al. |
| 2006/0008824 A1 | 1/2006 | Ronaghi et al. |
| 2006/0024678 A1 | 2/2006 | Buzby |
| 2006/0024711 A1 | 2/2006 | Lapid et al. |
| 2006/0024756 A1 | 2/2006 | Tibbe et al. |
| 2006/0046258 A1 | 3/2006 | Lapid et al. |
| 2006/0051265 A1 | 3/2006 | Mohamed et al. |
| 2006/0051775 A1 | 3/2006 | Bianchi et al. |
| 2006/0052945 A1 | 3/2006 | Rabinowitz et al. |
| 2006/0060767 A1 | 3/2006 | Wang et al. |
| 2006/0072805 A1 | 4/2006 | Tsipouras et al. |
| 2006/0073125 A1 | 4/2006 | Clarke et al. |
| 2006/0094109 A1 | 5/2006 | Trainer |
| 2006/0121452 A1 | 6/2006 | Dhallan |
| 2006/0121624 A1 | 6/2006 | Huang et al. |
| 2006/0128006 A1 | 6/2006 | Gerhardt et al. |
| 2006/0134599 A1 | 6/2006 | Toner et al. |
| 2006/0160105 A1 | 7/2006 | Dhallan |
| 2006/0160150 A1 | 7/2006 | Seilhamer et al. |
| 2006/0160243 A1 | 7/2006 | Tang et al. |
| 2006/0177832 A1 | 8/2006 | Brenner |
| 2006/0183886 A1 | 8/2006 | Ts'o et al. |
| 2006/0205057 A1 | 9/2006 | Wayner et al. |
| 2006/0223178 A1 | 10/2006 | Barber et al. |
| 2006/0228721 A1 | 10/2006 | Leamon et al. |
| 2006/0252054 A1 | 11/2006 | Lin et al. |
| 2006/0252061 A1 | 11/2006 | Zabeau et al. |
| 2006/0252068 A1 | 11/2006 | Lo et al. |
| 2006/0252071 A1 | 11/2006 | Lo et al. |
| 2006/0252087 A1 | 11/2006 | Tang et al. |
| 2007/0015171 A1 | 1/2007 | Bianchi et al. |
| 2007/0017633 A1 | 1/2007 | Tonkovich et al. |
| 2007/0026381 A1 | 2/2007 | Huang et al. |
| 2007/0026413 A1 | 2/2007 | Toner et al. |
| 2007/0026414 A1 | 2/2007 | Fuchs et al. |
| 2007/0026415 A1 | 2/2007 | Fuchs et al. |
| 2007/0026416 A1 | 2/2007 | Fuchs |
| 2007/0026417 A1 | 2/2007 | Fuchs et al. |
| 2007/0026418 A1 | 2/2007 | Fuchs et al. |
| 2007/0026419 A1 | 2/2007 | Fuchs et al. |
| 2007/0026469 A1 | 2/2007 | Fuchs et al. |
| 2007/0027636 A1 | 2/2007 | Rabinowitz |
| 2007/0037172 A1 | 2/2007 | Chiu et al. |
| 2007/0037173 A1 | 2/2007 | Allard et al. |
| 2007/0037273 A1 | 2/2007 | Shuler et al. |
| 2007/0037275 A1 | 2/2007 | Shuler et al. |
| 2007/0042238 A1 | 2/2007 | Kim et al. |
| 2007/0042339 A1 | 2/2007 | Toner et al. |
| 2007/0042360 A1 | 2/2007 | Afar et al. |
| 2007/0042368 A1 | 2/2007 | Zehentner-Wilkinson et al. |
| 2007/0048750 A1 | 3/2007 | Peck et al. |
| 2007/0054268 A1 | 3/2007 | Sutherland et al. |
| 2007/0054287 A1 | 3/2007 | Bloch |
| 2007/0059680 A1 | 3/2007 | Kapur et al. |
| 2007/0059683 A1 | 3/2007 | Barber et al. |
| 2007/0059710 A1 | 3/2007 | Luke et al. |

(56) References Cited

U.S. PATENT DOCUMENTS

| | | |
|---|---|---|
| 2007/0059716 A1 | 3/2007 | Balis et al. |
| 2007/0059718 A1 | 3/2007 | Toner et al. |
| 2007/0059719 A1 | 3/2007 | Grisham et al. |
| 2007/0059737 A1 | 3/2007 | Baker et al. |
| 2007/0059774 A1 | 3/2007 | Grisham et al. |
| 2007/0059781 A1 | 3/2007 | Kapur et al. |
| 2007/0059785 A1 | 3/2007 | Bac et al. |
| 2007/0065845 A1 | 3/2007 | Baker et al. |
| 2007/0065858 A1 | 3/2007 | Haley |
| 2007/0071762 A1 | 3/2007 | Ts'o et al. |
| 2007/0072228 A1 | 3/2007 | Brauch |
| 2007/0072290 A1 | 3/2007 | Hvichia |
| 2007/0077578 A1 | 4/2007 | Penning et al. |
| 2007/0092444 A1 | 4/2007 | Benos et al. |
| 2007/0092881 A1 | 4/2007 | Ohnishi et al. |
| 2007/0092917 A1 | 4/2007 | Guyon |
| 2007/0099207 A1 | 5/2007 | Fuchs et al. |
| 2007/0099219 A1 | 5/2007 | Teverovskiy et al. |
| 2007/0099289 A1 | 5/2007 | Irimia et al. |
| 2007/0105105 A1 | 5/2007 | Clelland et al. |
| 2007/0105133 A1 | 5/2007 | Clark et al. |
| 2007/0110773 A1 | 5/2007 | Asina et al. |
| 2007/0117158 A1 | 5/2007 | Coumans et al. |
| 2007/0122856 A1 | 5/2007 | Georges et al. |
| 2007/0122896 A1 | 5/2007 | Shuler et al. |
| 2007/0128655 A1 | 6/2007 | Obata |
| 2007/0131622 A1 | 6/2007 | Oakey et al. |
| 2007/0134658 A1 | 6/2007 | Bohmer et al. |
| 2007/0134713 A1 | 6/2007 | Cao |
| 2007/0135621 A1 | 6/2007 | Bourel et al. |
| 2007/0141587 A1 | 6/2007 | Baker et al. |
| 2007/0141588 A1 | 6/2007 | Baker et al. |
| 2007/0141717 A1 | 6/2007 | Carpenter et al. |
| 2007/0154928 A1 | 7/2007 | Mack et al. |
| 2007/0154960 A1 | 7/2007 | Connelly et al. |
| 2007/0160503 A1 | 7/2007 | Sethu et al. |
| 2007/0160974 A1 | 7/2007 | Sidhu et al. |
| 2007/0160984 A1 | 7/2007 | Huang et al. |
| 2007/0161064 A1 | 7/2007 | Kinch et al. |
| 2007/0166770 A1 | 7/2007 | Hsieh et al. |
| 2007/0170811 A1 | 7/2007 | Rubel |
| 2007/0172903 A1 | 7/2007 | Toner et al. |
| 2007/0178067 A1 | 8/2007 | Maier et al. |
| 2007/0178458 A1 | 8/2007 | O'Brien et al. |
| 2007/0178478 A1 | 8/2007 | Dhallan et al. |
| 2007/0178501 A1 | 8/2007 | Rabinowitz et al. |
| 2007/0187250 A1 | 8/2007 | Huang et al. |
| 2007/0196663 A1 | 8/2007 | Schwartz et al. |
| 2007/0196820 A1 | 8/2007 | Kapur et al. |
| 2007/0196840 A1 | 8/2007 | Roca et al. |
| 2007/0196869 A1 | 8/2007 | Perez et al. |
| 2007/0202106 A1 | 8/2007 | Palucka et al. |
| 2007/0202109 A1 | 8/2007 | Nakamura et al. |
| 2007/0202525 A1 | 8/2007 | Quake et al. |
| 2007/0202536 A1 | 8/2007 | Yamanishi et al. |
| 2007/0207351 A1 | 9/2007 | Christensen et al. |
| 2007/0207466 A1 | 9/2007 | Cantor et al. |
| 2007/0212689 A1 | 9/2007 | Bianchi et al. |
| 2007/0212698 A1 | 9/2007 | Bendele et al. |
| 2007/0212737 A1 | 9/2007 | Clarke et al. |
| 2007/0212738 A1 | 9/2007 | Haley et al. |
| 2007/0231851 A1 | 10/2007 | Toner et al. |
| 2007/0238105 A1 | 10/2007 | Barrett et al. |
| 2007/0259424 A1 | 11/2007 | Toner et al. |
| 2007/0264675 A1 | 11/2007 | Toner et al. |
| 2007/0275402 A1 | 11/2007 | Lo et al. |
| 2008/0020390 A1 | 1/2008 | Mitchell et al. |
| 2008/0023399 A1 | 1/2008 | Inglis et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton et al. |
| 2008/0071076 A1 | 3/2008 | Hahn et al. |
| 2008/0090239 A1 | 4/2008 | Shoemaker et al. |
| 2008/0096766 A1 | 4/2008 | Lee |
| 2008/0124721 A1 | 5/2008 | Fuchs |
| 2008/0138809 A1 | 6/2008 | Kapur et al. |
| 2008/0153090 A1 | 6/2008 | Lo et al. |
| 2008/0182261 A1 | 7/2008 | Bianchi |
| 2008/0096216 A1 | 8/2008 | Quake |
| 2008/0193927 A1 | 8/2008 | Mann et al. |
| 2008/0213775 A1 | 9/2008 | Brody et al. |
| 2008/0220422 A1 | 9/2008 | Shoemaker et al. |
| 2008/0299562 A1 | 12/2008 | Oeth et al. |
| 2008/0318235 A1 | 12/2008 | Handyside |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0170113 A1 | 7/2009 | Quake et al. |
| 2009/0170114 A1 | 7/2009 | Quake et al. |
| 2009/0215633 A1 | 8/2009 | Van Eijk et al. |
| 2009/0280492 A1 | 11/2009 | Stoughton et al. |
| 2009/0291443 A1 | 11/2009 | Stoughton et al. |
| 2009/0317798 A1 | 12/2009 | Heid et al. |
| 2010/0094562 A1 | 4/2010 | Shohat et al. |
| 2010/0112575 A1 | 5/2010 | Fan et al. |
| 2010/0112590 A1 | 5/2010 | Lo et al. |
| 2010/0124751 A1 | 5/2010 | Quake et al. |
| 2010/0124752 A1 | 5/2010 | Quake et al. |
| 2010/0136529 A1 | 6/2010 | Shoemaker et al. |
| 2010/0216151 A1 | 8/2010 | Lapid et al. |
| 2010/0216153 A1 | 8/2010 | Lapid et al. |
| 2010/0255492 A1 | 10/2010 | Quake et al. |
| 2010/0255493 A1 | 10/2010 | Quake et al. |
| 2010/0256013 A1 | 10/2010 | Quake et al. |
| 2010/0291571 A1 | 11/2010 | Stoughton et al. |
| 2010/0291572 A1 | 11/2010 | Stoughton et al. |
| 2010/0311064 A1 | 12/2010 | Oliphant et al. |
| 2011/0003293 A1 | 1/2011 | Stoughton et al. |
| 2011/0015096 A1 | 1/2011 | Chiu et al. |
| 2011/0105353 A1 | 5/2011 | Lo et al. |
| 2011/0117548 A1 | 5/2011 | Mitchell et al. |
| 2011/0171638 A1 | 7/2011 | Stoughton et al. |
| 2011/0312503 A1 | 12/2011 | Chuu et al. |
| 2012/0010085 A1 | 1/2012 | Rava et al. |
| 2012/0135872 A1 | 5/2012 | Chuu et al. |
| 2012/0171666 A1 | 7/2012 | Shoemaker et al. |
| 2012/0171667 A1 | 7/2012 | Shoemaker et al. |
| 2012/0183963 A1 | 7/2012 | Stoughton et al. |
| 2012/0208186 A1 | 8/2012 | Kapur et al. |
| 2013/0189688 A1 | 7/2013 | Shoemaker et al. |
| 2013/0189689 A1 | 7/2013 | Shoemaker et al. |
| 2013/0210644 A1 | 8/2013 | Stoughton et al. |
| 2013/0253369 A1 | 9/2013 | Rabinowitz et al. |
| 2013/0280709 A1 | 10/2013 | Stoughton et al. |
| 2013/0288242 A1 | 10/2013 | Stoughton et al. |
| 2013/0288903 A1 | 10/2013 | Kapur et al. |
| 2013/0295565 A1 | 11/2013 | Shoemaker et al. |
| 2013/0324418 A1 | 12/2013 | Fuchs et al. |
| 2014/0032128 A1 | 1/2014 | Rabinowitz et al. |
| 2014/0087385 A1 | 3/2014 | Rabinowitz et al. |
| 2015/0232936 A1 | 8/2015 | Shoemaker et al. |
| 2015/0344956 A1 | 12/2015 | Kapur et al. |
| 2016/0002737 A1 | 1/2016 | Fuchs et al. |

FOREIGN PATENT DOCUMENTS

| | | |
|---|---|---|
| EP | 0637996 B1 | 7/1997 |
| EP | 0405972 B1 | 5/1999 |
| EP | 1262776 A2 | 12/2002 |
| EP | 0994963 B1 | 5/2003 |
| EP | 0970365 B1 | 10/2003 |
| EP | 783694 B1 | 11/2003 |
| EP | 1262776 A3 | 1/2004 |
| EP | 1388013 B1 | 2/2004 |
| EP | 0920627 B1 | 5/2004 |
| EP | 1418003 A1 | 5/2004 |
| EP | 0739240 B1 | 6/2004 |
| EP | 1462800 A1 | 9/2004 |
| EP | 0919812 B1 | 10/2004 |
| EP | 1561507 A1 | 8/2005 |
| EP | 1409727 B1 | 11/2005 |
| EP | 1272668 B1 | 2/2007 |
| EP | 1754788 A2 | 2/2007 |

(56) References Cited

FOREIGN PATENT DOCUMENTS

| | | |
|---|---|---|
| EP | 1757694 A2 | 2/2007 |
| EP | 1409745 B1 | 4/2007 |
| EP | 1754788 A3 | 4/2007 |
| EP | 1770171 A1 | 4/2007 |
| EP | 1313882 B1 | 5/2007 |
| EP | 1803822 A1 | 7/2007 |
| EP | 951645 B1 | 8/2007 |
| EP | 1813681 A2 | 8/2007 |
| EP | 1832661 A1 | 9/2007 |
| EP | 1757694 A3 | 2/2008 |
| EP | 2161347 A2 | 3/2010 |
| EP | 2161347 A3 | 6/2010 |
| EP | 2366801 A1 | 9/2011 |
| EP | 2385143 A2 | 11/2011 |
| EP | 2423334 A2 | 2/2012 |
| EP | 2548972 A1 | 1/2013 |
| EP | 2589668 A1 | 5/2013 |
| EP | 1981995 B1 | 7/2013 |
| WO | WO 1990/06509 A1 | 6/1990 |
| WO | WO 1991/07660 A1 | 5/1991 |
| WO | WO 1991/016452 A1 | 10/1991 |
| WO | WO 1993/22053 A1 | 11/1993 |
| WO | WO 1994/29707 A1 | 12/1994 |
| WO | WO 1995/09245 A1 | 4/1995 |
| WO | WO 1997/46882 A1 | 12/1997 |
| WO | WO 1998/02528 A1 | 1/1998 |
| WO | WO 1998/10267 A1 | 3/1998 |
| WO | WO 99/22868 A1 | 5/1999 |
| WO | WO 1999/44064 A1 | 9/1999 |
| WO | WO 1999/061888 A2 | 12/1999 |
| WO | WO 00/06770 A1 | 2/2000 |
| WO | WO 00/40750 A1 | 7/2000 |
| WO | WO 2000/62931 A1 | 10/2000 |
| WO | WO 2001/35071 A2 | 5/2001 |
| WO | WO 2001/51668 A1 | 7/2001 |
| WO | WO 1999/061888 A3 | 12/2001 |
| WO | WO 2001/35071 A3 | 2/2002 |
| WO | WO 2002/012896 A1 | 2/2002 |
| WO | WO 2002/028523 A2 | 4/2002 |
| WO | WO 2002/030562 A1 | 4/2002 |
| WO | WO 2002/31506 A1 | 4/2002 |
| WO | WO 2002/44318 A1 | 6/2002 |
| WO | WO 2002/073204 A2 | 9/2002 |
| WO | WO 2003/003057 A2 | 1/2003 |
| WO | WO 03/020986 A1 | 3/2003 |
| WO | WO 2003/018757 A2 | 3/2003 |
| WO | WO 2003/019141 A2 | 3/2003 |
| WO | WO 2003/020974 A2 | 3/2003 |
| WO | WO 2003/023057 A2 | 3/2003 |
| WO | WO 2003/031938 A2 | 4/2003 |
| WO | WO 03/044217 A2 | 5/2003 |
| WO | WO 2003/035894 A2 | 5/2003 |
| WO | WO 2003/035895 A2 | 5/2003 |
| WO | WO 2003/044224 A1 | 5/2003 |
| WO | WO 2003/048295 A1 | 6/2003 |
| WO | WO 2003/069421 A2 | 8/2003 |
| WO | WO 2003/018757 A3 | 9/2003 |
| WO | WO 2003/020974 A3 | 9/2003 |
| WO | WO 03/044217 A3 | 10/2003 |
| WO | WO 2002/073204 A3 | 10/2003 |
| WO | WO 2003/031938 A3 | 11/2003 |
| WO | WO 2003/093795 A2 | 11/2003 |
| WO | WO 2003/023057 A3 | 12/2003 |
| WO | WO 2003/069421 A3 | 12/2003 |
| WO | WO 2003/035895 A3 | 1/2004 |
| WO | WO 2003/035894 A3 | 3/2004 |
| WO | WO 2004/025251 A2 | 3/2004 |
| WO | WO 2003/019141 A3 | 4/2004 |
| WO | WO 2004/029221 A2 | 4/2004 |
| WO | WO 2004/029221 A3 | 5/2004 |
| WO | WO 2004/037374 A2 | 5/2004 |
| WO | WO 2004/044236 A1 | 5/2004 |
| WO | WO 2004/056978 A1 | 7/2004 |
| WO | WO 2004/065629 A1 | 8/2004 |
| WO | WO 2004/076643 A2 | 9/2004 |
| WO | WO 2003/093795 A3 | 10/2004 |
| WO | WO 2004/037374 A3 | 10/2004 |
| WO | WO 2004/088310 A1 | 10/2004 |
| WO | WO 2004/025251 A3 | 11/2004 |
| WO | WO 2004/101762 A2 | 11/2004 |
| WO | WO 2004/113 877 A1 | 12/2004 |
| WO | WO 2004/101762 A3 | 2/2005 |
| WO | WO 2005/023091 A2 | 3/2005 |
| WO | WO 2005/028663 A2 | 3/2005 |
| WO | WO 2005/035725 A2 | 4/2005 |
| WO | WO 2005/042713 A2 | 5/2005 |
| WO | WO 2005/043121 A2 | 5/2005 |
| WO | WO 2005/047529 A1 | 5/2005 |
| WO | WO 2005/047532 A1 | 5/2005 |
| WO | WO 2005/023091 A3 | 6/2005 |
| WO | WO 2005/049168 A2 | 6/2005 |
| WO | WO 2005/058937 A2 | 6/2005 |
| WO | WO 2005/061075 A1 | 7/2005 |
| WO | WO 2005/049168 A3 | 9/2005 |
| WO | WO 2005/084374 A2 | 9/2005 |
| WO | WO 2005/084380 A2 | 9/2005 |
| WO | WO 2005/085476 A1 | 9/2005 |
| WO | WO 2005/085861 A2 | 9/2005 |
| WO | WO 2005/098046 A2 | 10/2005 |
| WO | WO 2005/108621 A1 | 11/2005 |
| WO | WO 2005/109238 A2 | 11/2005 |
| WO | WO 2005/028663 A3 | 12/2005 |
| WO | WO 2005/098046 A3 | 12/2005 |
| WO | WO 2005/116264 A2 | 12/2005 |
| WO | WO 2005/118852 A2 | 12/2005 |
| WO | WO 2005/121362 A2 | 12/2005 |
| WO | WO 2005/085861 A3 | 2/2006 |
| WO | WO 2006/010610 A2 | 2/2006 |
| WO | WO 2005/118852 A3 | 3/2006 |
| WO | WO 2006/023563 A2 | 3/2006 |
| WO | WO 2005/121362 A3 | 4/2006 |
| WO | WO 2006/041453 A1 | 4/2006 |
| WO | WO 2006/043181 A2 | 4/2006 |
| WO | WO 2005/109238 A3 | 6/2006 |
| WO | WO 2006/010610 A3 | 6/2006 |
| WO | WO 2006/043181 A3 | 6/2006 |
| WO | WO 2006/076567 A2 | 7/2006 |
| WO | WO 2006/078470 A2 | 7/2006 |
| WO | WO 2005/043121 A3 | 8/2006 |
| WO | WO 2006/076567 A3 | 9/2006 |
| WO | WO 2006/078470 A3 | 9/2006 |
| WO | WO 2006/097049 A1 | 9/2006 |
| WO | WO 2006/100366 A2 | 9/2006 |
| WO | WO 2005/042713 A3 | 11/2006 |
| WO | WO 2006/023563 A3 | 11/2006 |
| WO | WO 2006/120434 A1 | 11/2006 |
| WO | WO 2005/084380 A3 | 12/2006 |
| WO | WO 2005/116264 A3 | 2/2007 |
| WO | WO 2007/020081 A1 | 2/2007 |
| WO | WO 2004/076643 A3 | 3/2007 |
| WO | WO 2007/024264 A2 | 3/2007 |
| WO | WO 2007/028146 A2 | 3/2007 |
| WO | WO 2007/030949 A2 | 3/2007 |
| WO | WO 2007/033167 A2 | 3/2007 |
| WO | WO 2007/034221 A2 | 3/2007 |
| WO | WO 2007/035414 A2 | 3/2007 |
| WO | WO 2007/024264 A3 | 4/2007 |
| WO | WO 2007/036025 A1 | 4/2007 |
| WO | WO 2007/038264 A2 | 4/2007 |
| WO | WO 2007/041610 A2 | 4/2007 |
| WO | WO 2007/044091 A2 | 4/2007 |
| WO | WO 2007/044690 A2 | 4/2007 |
| WO | WO 2007/048076 A2 | 4/2007 |
| WO | WO 2007/030949 A3 | 5/2007 |
| WO | WO 2007/034221 A3 | 5/2007 |
| WO | WO 2007/050495 A2 | 5/2007 |
| WO | WO 2007/053142 A1 | 5/2007 |
| WO | WO 2007/053648 A2 | 5/2007 |
| WO | WO 2007/053785 A2 | 5/2007 |
| WO | WO 2007/059430 A2 | 5/2007 |
| WO | WO 2007/062222 A2 | 5/2007 |
| WO | WO 2005/058937 A3 | 6/2007 |
| WO | WO 2007/067734 A2 | 6/2007 |
| WO | WO 2007/048076 A3 | 7/2007 |

(56) References Cited

FOREIGN PATENT DOCUMENTS

| | | |
|---|---|---|
| WO | WO 2007/053648 A3 | 7/2007 |
| WO | WO 2007/075836 A2 | 7/2007 |
| WO | WO 2007/075879 A2 | 7/2007 |
| WO | WO 2007/076989 A1 | 7/2007 |
| WO | WO 2007/079229 A2 | 7/2007 |
| WO | WO 2007/079250 A2 | 7/2007 |
| WO | WO 2007/080583 A2 | 7/2007 |
| WO | WO 2007/082144 A2 | 7/2007 |
| WO | WO 2007/082154 A2 | 7/2007 |
| WO | WO 2007/082379 A2 | 7/2007 |
| WO | WO 2007/050495 A3 | 8/2007 |
| WO | WO 2007/075879 A3 | 8/2007 |
| WO | WO 2007/087612 A2 | 8/2007 |
| WO | WO 2007/089880 A2 | 8/2007 |
| WO | WO 2007/089911 A2 | 8/2007 |
| WO | WO 2007/090670 A1 | 8/2007 |
| WO | WO 2007/092473 A2 | 8/2007 |
| WO | WO 2007/092713 A2 | 8/2007 |
| WO | WO 2007/098484 A2 | 8/2007 |
| WO | WO 2006/100366 A3 | 9/2007 |
| WO | WO 2007/100684 A2 | 9/2007 |
| WO | WO 2007/100911 A2 | 9/2007 |
| WO | WO 2007/101609 A1 | 9/2007 |
| WO | WO 2007/033167 A3 | 10/2007 |
| WO | WO 2007/038264 A3 | 10/2007 |
| WO | WO 2007/044690 A3 | 10/2007 |
| WO | WO 2007/053785 A3 | 10/2007 |
| WO | WO 2007/059430 A3 | 10/2007 |
| WO | WO 2005/084374 A3 | 11/2007 |
| WO | WO 2007/035414 A3 | 11/2007 |
| WO | WO 2007/044091 A3 | 11/2007 |
| WO | WO 2007/089880 A3 | 11/2007 |
| WO | WO 2007/100911 A3 | 11/2007 |
| WO | WO 2007/126938 A2 | 11/2007 |
| WO | WO 2007/132166 A2 | 11/2007 |
| WO | WO 2007/132167 A2 | 11/2007 |
| WO | WO 2007/082379 A3 | 12/2007 |
| WO | WO 2007/098484 A3 | 12/2007 |
| WO | WO 2007/147018 A2 | 12/2007 |
| WO | WO 2007/147073 A2 | 12/2007 |
| WO | WO 2007/147074 A2 | 12/2007 |
| WO | WO 2007/147076 A2 | 12/2007 |
| WO | WO 2007/147079 A2 | 12/2007 |
| WO | WO 2007/062222 A3 | 1/2008 |
| WO | WO 2007/100684 A3 | 1/2008 |
| WO | WO 2007/075836 A3 | 2/2008 |
| WO | WO 2007/132166 A3 | 2/2008 |
| WO | WO 2008/017871 A1 | 2/2008 |
| WO | WO 2008/045158 A1 | 4/2008 |
| WO | WO 2007/089911 A3 | 5/2008 |
| WO | WO 2007/132167 A3 | 5/2008 |
| WO | WO 2007/028146 A3 | 6/2008 |
| WO | WO 2007/067734 A3 | 8/2008 |
| WO | WO 2008/111990 A1 | 9/2008 |
| WO | WO 2007/126938 A3 | 10/2008 |
| WO | WO 2007/082154 A3 | 11/2008 |
| WO | WO 2007/087612 A3 | 11/2008 |
| WO | WO 2007/092473 A3 | 11/2008 |
| WO | WO 2007/082144 A3 | 12/2008 |
| WO | WO 2007/092713 A3 | 12/2008 |
| WO | WO 2007/079229 A3 | 1/2009 |
| WO | WO 2009/013492 A1 | 1/2009 |
| WO | WO 2009/013496 A1 | 1/2009 |
| WO | WO 2007/080583 A3 | 2/2009 |
| WO | WO 2009/019455 A2 | 2/2009 |
| WO | WO 2007/079250 A3 | 3/2009 |
| WO | WO 2007/041610 A3 | 4/2009 |
| WO | WO 2009/019455 A3 | 4/2009 |
| WO | WO 2010/045617 A2 | 4/2010 |
| WO | WO 2011/094646 A1 | 8/2011 |
| WO | WO 2011/102998 A2 | 8/2011 |

OTHER PUBLICATIONS

Adinolfi, et al. Gene Amplification to Detect Fetal Nucleated Cells in Pregnant Women. The Lancet. Aug. 5, 1989:328-329.
Adinolfi, et al. Rapid detection of aneuploidies by microsatellite and the quantitative fluorescent polymerase chain reaction, Prenat. Diagn. 1997; 17(13):1299-311.
Adinolfi, M. On a Non-invasive Approach to Prenatel Diagnosis based on the detection of Fetal Nucleated Cells in Maternal Blood Samples. Prenatal Diagnosis. 1991;11:799-804.
Advisory action dated Mar. 4, 2015 for U.S. Appl. No. 12/689,548.
Advisory action dated Dec. 16, 2013 for U.S. Appl. No. 12/751,940.
Ahn, et al. A fully integrated micromachined magnetic particle separator. Journal of Microelectromechanical Systems. 1996; 5(3):151-158.
Allard, et al. Tumor cells circulate in the peripheral blood of all major carcinomas but not in healthy subjects or patients with nonmalignant diseases. Clin Cancer Res. Oct. 15, 2004;10(20):6897-904.
Allowed claims dated Dec. 9, 2010 for U.S. Appl. No. 11/701,686.
Amendment to the Claims dated Jun. 16, 2014 for U.S. Appl. No. 13/863,992.
Amendment to the Claims dated Dec. 5, 2013 for U.S. Appl. No. 12/751,940.
Amendments to the Claims Filed Mar. 29, 2013 with U.S. Patent Office for U.S. Appl. No. 12/751,940.
Amendments to the Claims. Filed Aug. 14, 2013 with U.S. Patent Office for U.S. Appl. No. 13/737,730.
Amendments to the Claims. Filed Jul. 11, 2013 with U.S. Patent Office for U.S. Appl. No. 13/831,342.
Amendments to the Claims. Filed Jul. 25, 2013 with U.S. Patent Office for U.S. Appl. No. 13/829,971.
Amendments to the Claims. Filed Mar. 15, 2013 with U.S. Patent Office for U.S. Appl. No. 13/835,926.
Amendments to the Claims. Filed Mar. 15, 2013 with U.S. Patent Office for U.S. Appl. No. 13/837,974.
Amendments to the Claims. Filed Nov. 7, 2013 with U.S. Patent Office for U.S. Appl. No. 13/863,992.
Andrews, et al. Enrichment of fetal nucleated cells from maternal blood: model test system using cord blood. Prenatal Diagnosis. 1995; 15:913-919.
Applicant's Amendment and Response dated Jun. 17, 2009 to Non-Final Office Action dated Jan. 28, 2009 re U.S. Appl. No. 11/701,686.
Applicant's Amendment and Response dated Jun. 24, 2010 to Office Action dated Jan. 27, 2010 re U.S. Appl. No. 11/701,686.
Applicant's Amendment and Response dated Nov. 13, 2009 to Office Action dated Sep. 11, 2009 re U.S. Appl. No. 11/701,686.
Applicant's response dated Jun. 10, 2011 to Office action dated Apr. 25, 2011 for U.S. Appl. No. 12/393,803.
Ariga, et al. Kinetics of fetal cellular and cell-free DNA in the maternal circulation during and after pregnancy: implications for noninvasive prenatal diagnosis. Transfusion, 2001; 41:1524-1530.
Arnould, et al. Agreement between chromogenic in situ hybridisation (CISH) and FISH in the determination of HER2 status in breast cancer, Br J Cancer, 2003; 88(10):1587-91, (Abstract only).
Babochkina, et al. Direct detection of fetal cells in maternal blood: a reappraisal using a combination of two different Y chromosome-specific FISH probes and a single X chromosome-specific probe. Arch Gynecol Obstet. Dec. 2005;273(3):166-9. (Abstract only).
Babochkina, T. I. Ph.D. Dissertation—Fetal cells in maternal circulation: Fetal cell separation and FISH analysis. University of Basel, Switzerland. Dec. 8, 2005, (123 pages).
Balko, et al. Gene expression patterns that predict sensitivity to epidermal growth factor receptor tyrosine kinase inhibitors in lung cancer cell lines and human lung tumors. BMC Genomics. Nov. 10, 2006;7:289 (14 pages).
Barrett, et al. Comparative genomic hybridization using oligonucleotide microarrays and total genomic DNA. Proc Natl Acad Sci U S A. 2004; 101(51):17765-70.
Basch, et al. Cell separation using positive immunoselective techniques. Journal of Immunological Methods. 1983;56:269-280.

(56) References Cited

OTHER PUBLICATIONS

Bauer, J. Advances in cell separation: recent developments in counterflow centrifugal elutriation and continuous flow cell separation. Journal of Chromatography, 1999;722:55-69.
Bloanod:CHI, et al. Fetal gender and aneuploidy detection using fetal cells in maternal analysis of NIFTY I data. Prenatal Diagnosis. 2002; 22:609-615.
Becker, et al. Fabrication of Microstructures With High Aspect Ratios and Great Structural Heights by Synchrotron Radiation Lithography, Galvanoforming, and Plastic Moulding (LIGA Process). Microelectronic Engineering, 1986;4:35-56.
Becker, et al. Planar quartz chips with submicron channels for two-dimensional capillary electrophoresis applications. J. Micromech Microeng. 1998;9:24-28.
Beebe et al. Functional Hydrogel Structures for Autonomous Flow Control Inside Microfluidic Channels. Nature. 2000; 404:588-590.
Bennett, et al. Toward the 1,000 dollars human genome. Pharmacogenomics. 2005; 6(4):373-82.
Berenson, et al. Cellular Immunoabsorption Using Monoclonal Antibodies. Transplantation. 1984;38:136-143.
Berenson, et al. Positive selection of viable cell populations using avidin-biotin.
Berg, H. C. Random Walks in Biology, Ch. 4. Princeton University Press. Princeton, NJ. 1993. pp. 48-64.
Berger, et al. Design of a microfabricated magnetic cell separator. Electrophoresis. Oct. 2001;22(18):3883-92.
Bianchi et al. Demonstration of fetal gene sequences in nucleated erythrocytes om maternal blood. American Journal of Human Genetics. 1989;45:A252.
Bianchi, et al. Isolation of fetal DNA from nucleated erythrocytes in maternal blood. Medical Sciences. 1990;87:3279-3283.
Bianchi, et al. Fetal nucleated erythrocytes (FNRBC) in maternal blood: erythroid-specific antibodies improve detection. The American Journal of Human Genetics. Oct. 1992. Supplemental to vol. 51, No. 4: 996.
Bianchi, et al. Isolation of Male Fetal DNA from Nucleated Erythrocytes (NRBC) in Maternal Blood. The American Pediatric Society and Society for Pediatric Research, (1989) Mar. 1989; 818:139A.
Bianchi, et al. Possible Effects of Gestational Age on the Detection of Fetal Nucleated Erythrocytes in Maternal Blood. Prenatal Diagnosis. 1991;11:523-528.
Bignell, et al. High-resolution analysis of DNA copy number using oligonucleotide microarrays. Genome Research. 2004; 14(2):287-295.
Binladen, et al. The Use of Coded PCR Primers Enables High-Throughput Sequencing of Multiple Homolog Amplification Products by 454 Parallel Sequencing. Feb. 2007, PLoS One. 2(2):e197, doi:10.1371/journal.pone.0000197.
Blake, et al. Assessment of multiplex fluorescent PCR for screening single cells for trisomy 21 and single gene defects. Mol. Hum. Reprod. 1999; 5(12):1166-75.
Bode, et al. Mutations in the tyrosine kinase domain of the EGFR gene are rare in synovial sarcoma. Mod Pathol. Apr. 2006;19(4):541-7.
Boehm, et al. Analysis of Defective Dystrophin Genes with cDNA Probes: Rearrangement Polymorphism, Detection of Deletions in Carrier Females, and Lower Than Expected Frequency of Carrier Mothers in Isolated Cases of Deletions. Pediatric Research, Apr. 1989: 139A-820.
Bohmer, et al. Differential Development of Fetal and Adult Haemoglobin Profiles in Colony Culture: Isolation of Fetal Nucleated Red Cells by Two-Colour Fluorescence Labelling. Br. J. Haematol. 1998; 103:351-60.
Bookout, et al. High-throughput real-time quantitative reverse transcription PCR. Curr. Prot. Mol. Biol. 2005; 15.8.1-15.8.21.
Braslavsky, et al. "Sequence information can be obtained from single DNA molecules," PNAS, Apr. 2003, vol. 100, No. 7, 3960-3964.
Brison, et al. General Method for Cloning Amplified DNA by Differential Screening with Genomic Probes. Molecular and Cellular Biology, 1982;2:578-587.
Brody, et al. Deformation and Flow of Red Blood Cells in a Synthetic Lattice: Evidence for an Active Cytoskeleton, Biophys. J. 68:2224-2232 (1995).
Brown, et al. Applicant-Initiated Interview Summary, with Office Action Summary, and Information Disclosure Statement by Applicant. Date Sep. 16, 2009.
Bustamante-Aragones, et al. Detection of a Paternally Inherited Fetal Mutation in Maternal Plasma by the Use of Automated Sequencing. Ann. N.Y. Acad. Sci. 1075: 108-117 (2006), pp. 108-117, XP-002652985.
Caggana, M. Microfabricated devices for sparse cell isolation. CNF Project #905-00. Cornell NanoScale Facility. 2003; pp. 38-39.
Caggana, M. Microfabricated devices for sparse cell isolation. CNF Project #905-00. Cornell NanoScale Facility. 2004-2005; pp. 32-33.
Calin, et al. A microRNA signature Associated with prognosis and progression in chronic lymphocytic leukemia. New England Journal of Medicine. 2005; 353:1793-1801.
Cappuzzo, et al. Epidermal growth factor receptor gene and protein and gefitinib sensitivity in non-small-cell lung cancer, J Natl Cancer Inst. May 4, 2005;97(9):643-55.
Cha, The utility of an erythroblast scoring system and gender-independent short tandem repeat (STR) analysis for the detection of aneuploid fetal cells in maternal blood. Prenat. Diagn. 2005; 25(7):586-91.
Chamberlain, et al. Deletion screening of the Duchenne muscular dystrophy locus via multiplex DNA amplification. Nucleic Acids Research. 1988;16:11141-11156.
Chan, et al. "DNA Mapping Using Microfluidic Stretching and Single-Molecule Detection of Fluorescent Site-Specific Tags," Genome Research, 2004, vol. 14, 1137-1146.
Chan, et al. Size distributions of maternal and fetal DNA in maternal plasma. Clin Chem. Jan. 2004;50(1):88-92.
Chang, et al. Assessment of Plasma DNA Levels, Allelic Imbalance, and CA 125 as Diagnostic Tests for Cancer. Nov. 20, 2002. J. Nat'l Cancer Inst. 94(22):1697-1703.
Chang, et al. Biomimetic technique for adhesion-based collection and separation of cells in a microfluidic channel. Lab Chip, 2005; 5:64-73.
Cheung, et al. Development and validation of a CGH microarray for clinical cytogenetic diagnosis. Genet Med. 2005; 7(6):422-32.
Chiu, et al. "Effects of Blood-Processing Protocols on Fetal and Total DNA Quantification in Maternal Plasma," Clinical Chemistiy, 2001, vol. 47, No. 9, 1607-1613.
Chiu, et al. Non-invasive prenatal assessment of trisomy 21 by multiplexed maternal plasma DNA sequencing: large scale validity study. BMJ, Jan. 11, 2011;342:c7401. doi: 10.1136/bmj.c7401.
Chiu, et al. Non-invasive prenatal diagnosis by single molecule counting technologies. Trends in Genetics, vol. 25, Issue 7, Jul. 2009, pp. 324-331.
Chiu, et al. Noninvasive prenatal diagnosis of fetal chromosomal aneuploidy by massively parallel genomic sequencing of DNA in maternal plasma. Proc Natl Acad Sci US A. Dec. 23, 2008;105(51):20458-63.
Chiu, et al. Patterned Deposition of Cells and Proteins Onto Surfaces by Using Three-Dimensional Microfluidic Systems. Proceedings of the National Academy of Sciences.
Choesmel, et al. Enrichment methods to detect bone marrow micrometastases in breast carcinoma patients: clinical relevance. Breast Cancer Res. 2004;6(5):R556-569.
Choolani, et al. Characterization of First Trimester Fetal Erythroblasts for Non-Invasive Prenatal Diagnosis. Mol. Hum. Reprod. 2003; 9:227-35.
Chou, et al. A Microfabricated Device for Sizing and Sorting DNA Molecules. Proceedings of the National Academy of Sciences of the United States of America. 1999; pp. 11-13.
Chou, et al. Sorting by diffusion: An asymmetric obstacle course for continuous molecular separation, PNAS. 1999; 96(24):13762-13765.

(56) References Cited

OTHER PUBLICATIONS

Christel, et al. High aspect ratio silicon microstructures for nucleic acid extraction. Solid-state sensor and actuator workshop, Hilton Head, SC. Jun. 8-11, 1998; 363-366.
Christensen, et al. Fetal Cells in Maternal Blood: A Comparison of Methods for Cell Isolation and Identification, Fetal Diagn, Ther. 2005; 20:106-12.
Chueh, et al. Prenatal Diagnosis Using Fetal Cells from the Maternal Circulation. West J. Med. 159:308-311 (1993).
Chueh, et al. Prenatal Diagnosis Using Fetal Cells in the Maternal Circulation. Seminars in Perinatology. 1990;14:471-482.
Chueh, et al. The search for fetal cells in the maternal circulation. J Perinat Med. 1991;19:411-420.
Cirigliano, et al. "Clinical application of multiplex quantitative fluorescent polymerase chain reaction (QF-PCR) for the rapid prenatal detection of common chromosome aneuploidies," Molecular Human Reproduction, 2001, vol. 7, No. 10, 1001-1006.
Claims mailed with RCE Response to Final Rejection dated Dec. 31, 2009 for U.S. Appl. No. 11/763,421, filed Jun. 14, 2007 (6 pages).
Claims. Filed Nov. 29, 2011 with U.S. Patent Office for U.S. Appl. No. 13/306,520.
Claims. Filed Nov. 29, 2011 with U.S. Patent Office for U.S. Appl. No. 13/306,640.
Claims. Filed Nov. 29, 2011 with U.S. Patent Office for U.S. Appl. No. 13/306,698.
Clayton, et al. Fetal Erythrocytes in the Maternal Circulation of Pregnant Women. Obstetrics and Gynecology. 1964;23:915-919.
Coble, et al. Characterization of New MiniSTR Loci to Aid Analysis of Degraded DNA. Jan. 2005. J. Forensic Sci. 50(1):42-53.
Collarini, et al. Comparison of methods for erythroblast selection: application to selecting fetal erythroblasts from maternal blood. Cytometry. 2001; 45:267-276.
Cotton, et al. Reactivity of cytosine and thymine in single-base-pair mismatches with hydroxylamine and osmium tetroxide and its application to the study of mutations. Proc Natl Acad Sci USA. Jun. 1988;85(12):4397-401.
Craig, et al. Identification of genetic variants using bar-coded multiplexed sequencing. Nat Methods. Oct. 2008; 5(10): 887-893. DOI:10.1038/nmeth.1251.
Cremer, et al. Detection of chromosome aberrations in human interphase nucleus by visualization of specific target DNAs with radioactive and non-radioactive in situ hybridization techniques: diagnosis of trisomy 18 with probe L1.84, Human Genetics. 1986;74:346-352.
Cremer, et al. Detection of chromosome aberrations in metaphase and interphase tumor cells by in situ hybridization using chromosome-specific libraiy probes. Human Genetics. 1988;80:235-246.
Cristofanilli, et al. Circulating tumor cells revisited. JAMA. 2010; 303(11):1092-1093.
Cristofanilli, et al. Circulating tumor cells, disease progression, and survival in metastatic breast cancer, N Engl J Med. Aug. 19, 2004;351(8):781-91.
Dahl, et al. Multigene Amplification and Massively Parallel Sequencing for Cancer Mutation Discovery. May 29, 2007, PNAS USA 104(22):9387-9392.
Das, et al. Dielectrophoretic segregation of different human cell types on microscope slides. Anal. Chem. 2005;77:2708-2719.
De Alba, et al. Prenatal diagnosis on fetal cells obtained from maternal peripheral blood: report of 66 cases. Prenat Diagn. Oct. 1999;19(10):934-40.
De Kretser, et al. The Separation of Cell Populations using Monoclonal Antibodies attached to Sepharose. Tissue Antigens. 1980;16:317-325.
De Luca, et al. Detection of circulating tumor cells in carcinoma patients by a novel epidermal growth factor receptor reverse transcription-PCR assay. Clin Cancer Res. Apr. 2000;6(4):1439-44.
Decision re: Institution of Inter Partes Review 37 C.F.R. § 42.108. Entered Oct. 25, 2013. For Case IPR2013-00277. U.S. Pat. No. 8,318,430.
Decision: Institution of Inter Partes Review 37 C.F.R. § 42.108. Dated . Entered Oct. 25, 2013. For Case IPR2013-00276. U.S. Pat. No. 8,318,430 B2.
Declaration of Atul J. Butte, M.D. Ph.D. in Support of Patent Owner's Response to Inter Partes Review of U.S. Pat. No. 8,316,430. US Patent Office. Dated Jan. 16, 2014.
Declaration of Cynthia Casson Morton. Dated May 29, 2013. U.S. Pat. No. 8,296,076.
Declaration of Cynthia Casson Morton. Dated May 10, 2013. In re: Chuu, et al., U.S. Pat. No. 8,318,430.
Declaration of Cynthia Casson Morton. Dated May 10, 2013. In re: Chuu, et al., U.S. Pat. No. 8,318,430, claims 1-18.
Declaration of Robert Nussbaum. Dated May 22, 2013. U.S. Pat. No. 8,296,076.
Declaration of Robert Nussbaum Dated May 8, 2013. In re Patent of: Chuu, et al. U.S. Pat. No. 8,318,430.
Declaration of Robert Nussbaum. Dated Apr. 16, 2013. In re Patent of: Fan, et al. U.S. Pat. No. 8,318,430, claims 1-18.
Delamarche, et al. Microfluidic Networks for Chemical Patterning of Substrates: Design and Application to Bioassays. Journal of the American Chemical Society. 1998; 120:500-508.
Delamarche, et al. Patterned Delivery of Immunoglobulins to Surfaces Using Microfluidic Networks. Science. 1997; 276:779-781.
Deng, et al. Enumeration and microfluidic chip separation of circulating fetal cells early in pregnancy from maternal blood. American Journal of Obstetrics & Gynecology. Dec. 2008 (vol. 199, Issue 6, p. S134).
Deposition of Dr. Cynthia Casson Morton. US Patent Office. Dated Dec. 10, 2013.
Deposition of Dr. Robert Nussbaum. US Patent Office. Dated Dec. 11, 2013.
Deshmukh, et al. Continuous Micromixer With Pulsatile Micropumps. Solid-State Sensor and Actuator Workshop, Hilton Head Island, South Carolina; Jun. 4-8, 2000:73-76.
Deutsch, et al. Detection of aneuploidies by paralogous sequence quantification. J Med Genet. Dec. 2004;41(12):908-15.
Devotek. "Separation of RNA & DNA by Gel Filtration Chromatography," Edvotek, 1987. 1-9.
Dhallan, et al. A non-invasive test for prenatal diagnosis based on fetal DNA present in maternal blood: a preliminary study. The Lancet, vol. 369, Issue 9560, Feb. 10, 2007, pp. 440-442.
Di Naro, et al. Prenatal diagnosis of beta-thalassaemia using fetal erythroblasts enriched from maternal blood by a novel gradient. Mol Hum Reprod. 2000; 6(6):571-4.
Diehl, et al. Digital quantification of mutant DNA in cancer patients. Curr Opin Oncol. Jan. 2007;19(1):36-42.
Dilella, et al. Screening for Phenylketonuria Mutations by DNA Amplification with the Polymerase Chain Reaction. The Lancet. Mar. 5, 1988:497-499.
Dohm, et al. Substantial biases in ultra-short read data sets from high-throughput DNA sequencing. Nucleic Acids Research. 2008. 36: e105 doi: 10.1093\nark\gkn425.
Doyle, et al. Self-Assembled Magnetic Matrices for DNA Separation Chips. Science 295:2237 (2002).
Dragovich, et al. Anti-EGFR-targeted therapy for esophageal and gastric cancers: concept. Journal of Oncology. 2009; vol. 2009, Article ID 804108.
Dressman, et al. "Transforming single DNA molecules into fluorescent magnetic particles for detection and enumeration of genetic variations." PNAS, Jul. 2003, vol. 100, No. 15, 8817-8822.
Drmanac, et al. DNA Sequence Determination by Hybridization: A Strategy for Efficient Large-Scale Sequencing. Science Jun. 11, 1993: vol. 260 No. 5114 pp. 1649-1652 DOI: 10.1126/science. 8503011. Jun. 11, 1993.
Eigen, et al. Sorting Single Molecules: Application to Diagnostics and Evolutionary Biotechnology. Proceedings of the National Academy of Sciences of the United States of America. 1994;91:5740-5747.
Emanuel, et al. Amplification of Specific Gene Products from Human Serum. GATA, 1993, vol. 10, No. 6, 144-146.
European office action dated May 22, 2015 for EP Application No. 07798579.4.

(56) References Cited

OTHER PUBLICATIONS

European office action dated Jun. 26, 2012 for EP Application No. 11159371.1.
European office action dated Jul. 17, 2013 for EP Application No. 11159371.1, 8 pages.
European office action dated Aug. 22, 2013 for EP Application No. 07798579.4.
European office action dated Oct. 8, 2012 for EP Application No. 11175845.
European office action dated Dec. 13, 2013 for EP Application No. 11159371.1.
European office action dated Dec. 16, 2013 for EP Application No. 12175907.
European office action dated Dec. 18, 2012 for EP Application No. 11159371.1.
European Search Opinion dated Jul. 31, 2009 for EP07763674.4.
European Search Report Office action dated Dec. 21, 2010 for EP07763674.4.
European search report and search opinion dated Jan. 2, 2013 for EP Application No. 12175907.0.
European search report and search opinion dated Mar. 16, 2012 for EP Application No. 11182181.
European search report and search opinion dated Apr. 9, 2013 for EP Application No. 12180149.2.
European search report and search opinion dated Nov. 17, 2011 forEP Application No. 11175845.
European search report and search opinion dated Nov. 9, 2009 for Application No. 7784442.1.
European search report and search opinion dated Dec. 21, 09 for Application No. 07798579.4.
European search report and search opinion dated Dec. 22, 2009 for Application No. 07784444.7.
European search report and search opinion dated Dec. 22, 09 for Application No. 07798580.2.
European Search Report dated Jul. 31, 2009 for EP07763674.4.
Applicant's Response with Allowed Claims dated Dec. 2, 2010 issued in U.S. Appl. No. 11/701,686.
Pending Claims filed with the USPTO on Apr. 26, 2010 for U.S. Appl. No. 11/701,686.
Extended European Search Report for U.S. Appl. No. 11/159,371 dated Aug. 10, 2011, 10 pages.
Falcidia, et al. Fetal Cells in maternal blood: a six-fold increase in women who have undergone amniocentesis and cany a fetus with Down syndrome: a multicenter study. Neuropediatrics. 2004; 35(6):321-324, (Abstract only).
Fan, et al. Detection of aneuploidy with digital polymerase chain reaction. Anal Chem. Oct. 1, 2007; 79(19):7576-9.
Fan, et al. Highly Parallel Genomic Assays. Aug. 2006. Nat. Rev. Genet. 7(8):632-44.
Fan, et al. Highly parallel SNP genotyping. Cold Spring Harb. Symp. Quant. Biol. 2003; 68:69-78.
Fan, et al. Noninvasive diagnosis of fetal aneuploidy by shotgun sequencing DNA from maternal blood. Proc Natl Acad Sci U S A. Oct. 21, 2008;105(42):16266-71.
Fan, et al. Single cell degenerate oligonucleotide primer-PCR and comparative genomic hybridization with modified control reference. Journal of Ahejian University—Science A. 2001; 2(3):318-321.
Fan, et al. Microfluidic digital PCR enables rapid prenatal diagnosis of fetal aneuploidy. Am J Obstet Gynecol. May 2009;200(5):543.e1-7.
Farber, et al. Demonstration of spontaneous XX/XY chimerism by DNA fingerprinting. Human Genetics. 1989;82:197-198.
Farooqui, et al. Microfabrication of Submicron Nozzles in Silicon Nitride. Journal of Microelectromechanical Systems. 1992; 1(2):86-88.
Feinberg, et al. A technique for radiolabeling DNA restriction endonuclease fragments to high specific activity. Anal Biochem, Jul. 1, 1983;132(1):6-13.

Fiedler, et al. Dielectrophoretic Sorting of Particles and Cells in a Microsystem.
Findlay, et al. Using MF-PCR to diagnose multiple defects from single cells: implications for PGD. Mol Cell Endocrinol, 2001; 183 Suppl 1:S5-12.
Fleischmann, et al. Whole-Genome Random Sequencing and Assembly of Haemophilus influenzae Rd. Science Jul. 28, 1995: vol. 269 No. 5223 pp. 496-512 DOI: 10.1126/science.7542800.
Freemantle, M. Downsizing Chemistry. Chemical analysis and synthesis on microchips promise a variety of potential benefits. Chemical & Engineering News. 1999; pp. 27-36.
Fu, et al. An integrated microfabricated cell sorter. Anal Chem. 2002;74:2451-2457.
Fu, et al. A Microfabricated Fluorescence-Activated Cell Sorter. Nature Biotechnology. 1999; 17:1109-1111.
Fuhr, et al. Biological Application of Microstructures. Topics in Current Chemistry. 1997; 194:83-116.
Fullwood, et al. Next Generation DNA sequencing of paired-end tags (PET) for transcriptome and genome analyses. Genome Research, 2009, 19:521-532.
Furdui, et al. Immunomagnetic T cell capture from blood for PCR analysis using microfluidic systems. Lab Chip, Dec. 2004;4(6):614-8.
Ganshirt-Ahlert, et al. Magnetic cell sorting and the transferrin receptor as potential means of prenatal diagnosis from maternal blood. Am J Obstet Gynecol. 1992;166:1350-1355.
Ganshirt-Ahlert, et al. Noninvasive prenatal diagnosis: Triple density gradient, magnetic activated cell sorting and FISH prove to be an efficient and reproducible method for detection of fetal aneuploidies from maternal blood. The American Journal of Human Genetics. Oct. 1992. Supplemental to vol. 51, No. 4: 182.
Gardella, et al. Second Petition for Inter Partes Review Under 35 U.S.C. §§ 311-319 and 37 C.F.R, § 42.100 Et Seq.(Claims 19-30), Dated May 10, 2013, for U.S. Pat. No. 8,318,430.
Gardella, G. First Petition for Inter Partes Review Under 35 U.S.C. §§ 311-319 and 37 C.F.R. § 42.100 Et Seq. (Claims 1-18). Dated May 10, 2013. U.S. Pat. No. 8,318,430.
Gardella, G. Petition for Inter Partes Review Under 35 U.S.C. §§ 311-319 and 37 C.F.R, § 42.100 Et Seq. Dated May 24, 2013, U.S. Pat. No. 8,296,076.
GenomeWeb. Immunicon inks biomarker assay, lab services deal with Merck Serona. Available at C:\Documents and Settings\fc3\Local Settings\Temporary Internet Files\OLK35E\141896-1.htm. Accessed on Sep. 11, 2007.
Ghia, et al. Ordering of human bone marrow B lymphocyte precursors by single-cell polymerase chain reaction analyses of the rearrangement status of the immunoglobulin.
Giddings, J. C. Chemistry 'Eddy' Diffusion in Chromatography. Nature. 1959;184:357-358.
Giddings, J. C. Field-Flow Fractionation: Analysis of Macromolecular, Colloidal, and Particulate Materials. Science. 1993;260:1456-1465.
Gonzalez, et al. Multiple displacement amplification as a pre-polymerase chain reaction (pre-PCR) to process difficult to amplify samples and low copy number sequences from natural environments. Environ Microbiol. 2005; 7(7):1024-8.
Graham. Efficiency comparison of two preparative mechanisms for magnetic separation of eiythrocytes from whole blood. J. Appl, Phys. 1981; 52:2578-2580.
Greaves, et al. Expression of the OKT Monoclonal Antibody Defined Antigenic Determinants in Malignancy. Int. J. Immunopharmac. 1981;3:283-299.
Guetta, et al. Analysis of fetal blood cells in the maternal circulation: challenges, ongoing efforts, and potential solutions. Stem Cells Dev. 2004;13(1):93-9.
Gunderson, et al. A genome-wide scalable SNP genotyping assay using microarray technology. Nat Genet. 2005; 37(5):549-54.
Hahn, et al. "Prenatal Diagnosis Using Fetal Cells and Cell-Free Fetal DNA in Maternal Blood: What is Currently Feasible?" Clinical Obstetrics and Gynecology, Sep. 2002, vol. 45, No. 3, 649-656.
Hahn, et al. Current applications of single-cell PCR. Cell. Mol. Life Sci. 2000; 57(1):96-105. Review.

(56) References Cited

OTHER PUBLICATIONS

Hahn, et al. Microsystem for isolation of fetal DNA from maternal plasma by preparative size separation. Clin Chem. Dec. 2009;55(12):2144-52. doi: 10.1373/clinchem.2009.127480. Epub Oct. 1, 2009.
Hall. Advanced Sequencing Technologies and their Wider Impact in Microbiology. 2007. J. Exp. Biol. 209:1518-1525.
Hamabe, et al. Molecular study of the Prader-Willi syndrome: deletion, RFLP, and phenotype analyses of 50 patients. Am J Med Genet. Oct. 1, 1991;41(1):54-63.
Han, et al. Separation of Long DNA Molecules in a Microfabricated Entropic Trap Array. Science. 2000;288:1026-1029.
Hardenbol, et al. Highly multiplexed molecular inversion probe genotyping: over 10,000 targeted SNPs genotyped in a single tube assay. Genome Res. 2005;15(2):269-75.
Hardenbol, et al. Multiplexed genotyping with sequence-tagged molecular inversion probes. Nat. Biotechnol. 2003; 21(6):673-8.
Harris, et al. Single-molecule DNA sequencing of a viral genome. Science. Apr. 4, 2008;320(5872):106-9.
Hartmann, et al. Gene expression profiling of single cells on large-scale oligonucleotide arrays. Nucleic Acids Research, 2006; 34(21): e143, (11 pages).
Herzenberg, et al. Fetal cells in the blood of pregnant women: Detection and enrichment by fluorescence-activated cell sorting. Proc. Natl. Acad. Sci. 1979;76:1453-1455.
Holt, et al. The new paradigm of flow cell sequencing. DOI: 10.1101/gr.073262.107 Genome Res. 2008. 18: 839-846.
Holzgreve, et al. Fetal Cells in the Maternal Circulation. Journal of Reproductive Medicine. 1992;37:410-418.
Hong, et al. A nanoliter-scale nucleic acid processor with parallel architecture. Nat. Biotechnol. 2004; 22(4):435-9.
Hong, et al. Molecular biology on a microfluidic chip. Journal of Physics: Condensed Matter, 2006, vol. 18, S691-S701.
Hosono, et al. Unbiased whole-genome amplification directly from clinical samples. Genome Res. May 2003;13(5):954-64.
Hromadnikova, et al. "Quantitative analysis of DNA levels in maternal plasma in normal and Down syndrome pregnancies." Bio Med Central, May 2002, 1-5.
Huang, et al. A DNA prism for high-speed continuous fractionation of large DNA molecules. Nature Biotechnology, 2002;20:1048-1051.
Huang, et al. Continuous Particle Separation Through Deterministic Lateral Displacement. Science 304:987-90 (2004).
Huang, et al. Electric Manipulation of Bioparticles and Macromolecules on Microfabricated Electrodes. Analytical Chemistiy. 2001; pp. 1549-1559.
Huang, et al. Role of Molecular Size in Ratchet Fractionation. 2002; 89(17):178301-1-178301-4.
Huh, et al. Gravity-driven microhydrodynamics-based cell sorter (microHYCS) for rapid, inexpensive, and efficient cell separation and size-profiling. 2nd Annual International IEEE-EMBS Special Topic Conference on Microtechnology in Medicine and Biology. Madison, Wisconsin USA; May 2-4, 2002:466-469.
Hviid T. In-Cell PCT method for specific genotyping of genomic DNA from one individual in a mixture of cells from two individuals: a model study with specific relevance to prenatal diagnosis based on fetal cells in maternal blood. Molecular Diagnostics and Genetics. 2002; 48:2115-2123.
Hviid, T. In-cell polymerase chain reaction: strategy and diagnostic applications. Methods Mol Biol. 2006;336:45-58.
International preliminary report on patentability dated Oct. 29, 2008 for PCT/US2007/003209.
International Preliminary Report on Patentability dated Dec. 16, 2008 for PCT Application No. US2007/071248.
International search report and written opinion dated Feb. 25, 2008 for PCT Application No. US2007/71248.
International search report and written opinion dated Jan. 25, 2008 for PCT Application No. US2007/71250.
International search report and written opinion dated Nov. 15, 2007 for PCT Application No. US2007/71149.
International search report and written opinion dated Feb. 25, 2008 for PCT Application No. US07/71148.
International search report and written opinion dated Mar. 16, 2010 for PCT Application No. US2009/57136.
International Search Report and Written Opinion dated Sep. 18, 2008 for PCT/US2007/003209, received Sep. 22, 2008.
International search report dated Jan. 16, 2008 for PCT Application No. US2007/71247.
Ishikawa, et al. Allelic dosage analysis with genotyping microarrays. Biochem Biophys Res Commun, Aug. 12, 2005;333(4):1309-14.
Iverson, et al. Detection and Isolation of Fetal Cells From Maternal Blood Using the Fluorescence-Activated Cell Sorter (FACS). Prenatal Diagnosis 1981;1:61-73.
Jama, et al. Quantification of cell-free DNA levels in maternal plasma by STR analysis. Mar. 24-28, 2010. ACMG Annual Clinical Genetics Meeting Poster 398. Available at http://acmg.omnibooksonline.com/2010/data/papers/398.pdf. Accessed Apr. 5, 2013.
Jan, et al. Fetal Erythrocytes Detected and Separated from Maternal Blood by Electronic Fluorescent Cell Sorter. Texas Rep Biol Med. 1973;31:575.
Jeon, et al. Generation of Solution and surface Gradients Using Microfluidic Systems. Langmuir. 2000, pp. 8311-8316.
Jiang, et al. Genome amplification of single sperm using multiple displacement amplification. Nucleic Acids Res. 2005; 33(10):e91. (9 pages).
Jiang, et al. Old can be new again: HAPPY whole genome sequencing, mapping and assembly. Int J Biol Sci. 2009;5(4):298-303, Epub Apr. 15, 2009.
Joint Claim Construction and Prehearing Statement. Case: 12-cv-05501-SI; Dated May 3, 2013.
Kamholz, et al. Quantitative Analysis of Molecular Interaction in a Microfluidic Channel: the T-Sensor, Analytical Chemistry. 1999; pp. 5340-5347.
Kan, et al. Concentration of Fetal Red Blood Cells From a Mixture of Maternal and Fetal Blood by Anti-i Serum—An Aid to Prenatal Diagnosis of Hemoglobinopathies. Blood. 1974; 43:411-415.
Kartalov et al.: "Microfluidic device reads up to four consecutive base pairs in DNA sequencing-by-synthesis.", Nucleic Acids Research, 2004, vol. 32, No. 9, 2004, pp. 2873-2879, XP-002652987.
Kasakov, et al. Extracellular DNA in the blood of pregnant women. Tsitologiia. 1995;37(3):232-6. (English translation only).
Kazakov, et al. Extracellular DNA in the blood of pregnant women Tsitologiia. 1995; 37(3): 232-6.
Kenis, et al. Microfabrication Inside Capillaries Using Multiphase Laminar Flow Patterning. Science. 1999; 285:83-85.
Kim, et al. Polymer microstructures formed by moulding in capillaries. Nature. 1995;376:581-584.
Kimura, et al. Deletional mutant EGFR detected in circulating tumor-derived DNA from lung cancer patients treated with gefitinib. American Association for Cancer Research 96th Annual Meeting, Apr. 16-20, 2005, Abstract 479.
Kimura, et al. The DYRK1A gene, encoded in chromosome 21 Down syndrome critical region, bridges between (β-amyloid production and tan phosphorylation in Alzheimer disease. Human Molecular Genetics, Nov. 29, 2008, vol. 16, No. 1, 15-23.
Klein, C. A. Single cell amplification methods for the study of cancer and cellular ageing. Mech. Ageing Dev. 2005; 126(1):147-51.
Klein, et al. Comparative genomic hybridization, loss of heterozygosity, and DNA sequence analysis of single cells. Proc Natl Acad Sci US A. 1999; 96(8):4494-9.
Kobayashi, et al. EGFR mutation and resistance of non-small-cell lung cancer to gefitinib. N Engl J Med. Feb. 24, 2005;352(8):786-92.
Kogan, et al. An Improved Method for Prenatal Diagnosis of Genetic Diseases by Analysis of Amplified DNA Sequences, Application to Hemophilia A. The New England Journal of Medicine. 1987;317:985-990.
Koide, et al. Fragmentation of Cell-Free Fetal DNA in Plasma and Urine of Pregnant Women. Jul. 2005, Prenat. Diagn, 25(7):604-7.
Korenberg, et al. Down syndrome phenotypes: the consequences of chromosomal imbalance. PNAS 1994;91:4997-5001.

(56) References Cited

OTHER PUBLICATIONS

Krabchi, et al. Quantification of all fetal nucleated cells in maternal blood between the 18th and 22nd weeks of pregnancy using molecular cytogenic techniques. Clin. Genet. 2001; 60:145-150.
Krivacic, et al. A rare-cell detector for cancer. PNAS. 2004; 101:10501-10504.
Kulozik, et al. Fetal Cell in the Maternal Circulation: Detection by Direct AFP-Immunoflourescence. Human Genetics. 1982;62:221-224.
Kurg, et al. Arrayed primer extension: solid-phase four-color DNA resequencing and mutation detection technology. Genet Test. 2000;4(1):1-7.
Lander, et al. Initial sequencing and analysis of the human genome. Nature 409, 860-921 (Feb. 15, 2001) I DOI: 10.1038/35057062; Received Dec. 7, 2000; Accepted Jan. 9, 2001.
Leon, et al. Free DNA in the semm of cancer patients and the effect of therapy. Cancer Res. Mar. 1977;37(3):646-50.
Leutwyler, K. Mapping Chromosome 21. Available at http://www.scientificamerican.com/article.cfm?id=mapping-chromosome-21. Accessed Feb. 3, 2010.
Levett, et al. A large-scale evaluation of amnio-PCR for the rapid prenatal diagnosis of fetal trisomy. Ultrasound Obstet Gynecol. 2001; 17(2):115-8.
Li, et al. Transport, Manipulation, and Reaction of Biological Cells On-Chip Using Electrokinetic Effects. Analytical Chemistry., 1997; pp. 1564-1568.
Li, et al. Amplification and analysis ofDNA sequences in single human sperm and diploid cells. Nature. 1988;335:414-417.
Li, et al. Mapping short DNA sequencing reads and calling variants using mapping quality scores. Genome Research. Genome Res. Nov. 2008;18(11):1851-8.
Li, et al. Size separation of circulatory DNA in maternal plasma permits ready detection of fetal DNA polymorphisms. Clin Chem. Jun. 2004;50(6):1002-11.
Li, et al. Mapping short DNA sequencing reads and calling variants using mapping quality scores. Genome Res. Nov. 2008;18(11):1851-8. doi: 10.1101/gr.078212.108. Epub Aug. 19, 2008.
Lighter, et al. Delineation of individual human chromosomes in metaphase and interphase cells by in situ suppression hybridization using recombinant DNA libraries. Hum Genet. 1988; 80(3):224-234.
Lieberfarb, et al.Genome-wide loss of heterozygosity analysis from laser capture microdissected prostate cancer using single nucleotide polymorphic allele (SNP) arrays and a novel bioinformatics platform dChipSNP, Cancer Res.Aug. 15, 2003;63(16):4781-5.
Liu, et al. Development and validation of a T7 based linear amplification for genomic DNA. BMC Genomics.2003; 4(1):19.(11 pages).
Liu, et al. Feasibility Study of Using Fetal DNA in Maternal Plasma for Non-invasive Prenatal Diagnosis.2007.ActaObstet.Gynecol. Scand.86(5):535-41.
Lo, et al. Prenatal diagnosis of fetal RhD status by molecular analysis of maternal plasma. N Engl J Med 1998; 339:1734-1738 Dec. 10, 1998 DOI: 10.1056/NEJM199812103392402.
Lo, et al. Presence of fetal DNA in maternal plasma and serum. The Lancet, Aug. 16, 1997, vol. 350, 485-487.
Lo, et al. Quantitative Analysis of Fetal NA in Maternal Plasma and Serum: Implications for Noninvasive Prenatal Diagnosis. Am J. Hum. Genet., 1998, vol. 62, 768-775.
Lo, et al. Rapid Clearance of Fetal DNA from Maternal Plasma. Jan. 1999. Am. J. Hum. Genet. 64(1):218-24.
Lo, et al. Detection of fetal RhD sequence from peripheral blood of sensitized RhD-negative pregnant women, British Journal of Haematology, 1994, vol. 87, 658-660.
Lo, et al. Detection of single-copy fetal DNA sequence from maternal blood. The Lancet, Jun. 16, 1990, vol. 335, 1463-1464.
Lo, et al. Digital PCR for the molecular detection of fetal chromosomal aneuploidy. PNAS.Aug. 7, 2007; 104(32):13116-13121.
Lo, et al. Fetal DNA in Maternal Plasma.Ann N.Y.Acad.Sci, Apr. 2000, vol. 906, 141-147.
Lo, et al. Increased Fetal DNA Concentrations in the Plasma of Pregnant Women Carrying Fetuses with Trisomy 21, Oct. 1999, Clin.Chem. 45(10):1747-51.
Lo, et al. Plasma placental RNA allelic ratio permits noninvasive prenatal chromosomal aneuploidy detection.Nat Med.Feb. 2007;13(2):218-23.
Lo, et al. Prenatal diagnosis: progress through plasma nucleic acids. Nature. Jan. 2007, vol. 8, 71-76.
Lo, et al. Prenatal sex determination by DNA amplification from material peripheral blood. The Lancet. Dec. 9, 1989:1363-1365.
Lo, Y. M. Noninvasive prenatal detection of fetal chromosomal aneuploidies by maternal plasma nucleic acid analysis: a review of the current state of the art. BJOG, 2009, vol. 116, 152-157.
Loken, et al. Flow Cytometric Analysis of Human Bone Marrow: I. Normal Erythroid Development. Blood. 1987;69:255-263.
Lun, et al. Microfluidics Digital PCR Reveals a Higher than Expected Fraction of Fetal DNA in Maternal Plasma. Clinical Chemistiy, 2008, vol. 54, No. 10, 1664-1672.
Mahr, et al. Fluorescence in situ hybridization of fetal nucleated red blood cells. The American Journal of Human Genetics. Oct. 1992, Supplemental to vol. 51, No. 4: 1621.
Maloney et al. "Microchimerism of maternal origin persists into adult life," J. Clin. Invest. 104:41-47 (1999).
Marcus, et al. Microfluidic Single-Cell mRNA Isolation and Analysis. American Chemical Society, Mar. 2006; 76:3084-3089.
Marcus, et al. Parallel Picoliter RT-PCR Assays Using Microfluidics. Analytical Chemistry, Feb. 1, 2006, vol. 78, No. 3, 956-958.
Margulies, et al. Genome sequencing in microfabricated high-density picolitre reactors. Nature. 2005; 437:376-80.
Marks, et al. Epidermal growth factor receptor (EGFR) expression in prostatic adenocarcinoma after hormonal therapy: a fluorescence in situ hybridization and.
Martin, et al. "A method for using serum or plasma as a source of NDA for HLA typing," Human Immunology, 1992; 33:108-113.
Martin, New technologies for large-genome sequencing. Genome, 1989, vol. 31, No. 2: pp. 1073-1080 DOI: 10.1139/g89-184.
Mavrou, et al. Identification of nucleated red blood cells in maternal circulation: A second step in screening for fetal aneuploidies and pregnancy complications. Prenat Diagn. 2007; 247:150-153.
McCabe, et al. DNA microextraction from dried blood spots on filter paper blotters: potential applications to newborn screening. Hum Genet. 1987;75:213-216.
McCarley, et al. Patterning of surface-capture architectures in polymer-based microanalytical devices. In Kutter, et al. Eds. Royal Society of Chemistry Special Publication. 2005; 130-132. (Abstract only).
Mehrishi, et al. Electrophoresis of cells and the biological relevance of surface charge. Electrophoresis.2002;23:1984-1994.
Melville, et al. Direct magnetic separation of red cells from whole blood. Nature. 1975; 255:706.
Meng, et al.: "Design and Synthesis of a Photocleavable Fluorescent Nucleotide 3'-0-Allyl-dGTPPC-Bodipy-FL-510 as a Reversible Terminator for DNA Sequencing by Synthesis", J. Org. Chem. 2006, 71, pp. 3248-3252, XP-002652986.
Metzker, et al. Sequencing technologies—the next generation. Nature Reviews Genetics 11, 31-46 (Jan. 2010) I DOI:10.1038/mg2626.
Mirzabekov, et al. DNA sequencing by hybridization—a mega sequencing method and a diagnostic tool? Trends in Biotechnology, vol. 12, Issue 1, Jan. 1994, pp. 27-32.
Mohamed, et al. A Micromachined Sparse Cell Isolation Device: Application in Prenatal Diagnostics. Nanotech 2006 vol. 2; 641-644, (Abstract only).
Mohamed, et al. Biochip for separating fetal cells from maternal circulation. J Chromatogr A. Aug. 31, 2007;1162(2):187-92.
Mohamed, et al. Development of a rare cell fractionation device: application for cancer detection. IEEE Trans Nanobioscience. 2004; 3(4): 251-6.
Moore, et al. Lymphocyte fractionation using immunomagnetic colloid and a dipole magnet flow cell sorter, J Biochem Biophys Methods. 1998;37:11-33.
Moorhead, et al. Optimal genotype determination in highly multiplexed SNP data. Eur. J. Hum. Genet. 2006;14(2):207-15, (published online Nov. 23, 2005).

(56) References Cited

OTHER PUBLICATIONS

Mueller, et al. Isolation of fetal trophoblast cells from peripheral blood of pregnant women. The Lancet. 1990;336:197-200.
Muller, et al. Moderately repeated DNA sequences specific for the short arm of the human Y chromosome are present in XX makes and reduced in copy number in an XY female. 1986;14:1325-1340.
Mullis, et al. Specific Enzymatic Amplification of DNA In Vitro: The Polymerase Chain Reaction, Cold Spring Harbor Symposia on Quantitative Biolgy 1986;51:263-273.
Murakami, et al. A novel single cell PCR assay: detection of human T lymphotropic virus type I DNA in lymphocytes of patients with adult T cell leukemia. Leukemia. Oct. 1998;12(10):1645-50.
Murthy, et al. Assessment of multiple displacement amplification for polymorphism discovery and haplotype determination at a highly polymorphic locus, MC1R. Hum. Mutat. 2005; 26(2):145-52.
Myers, et al. Detection of single base substitutions by ribonuclease cleavage at mismatches in RNA:DNA duplexes. Science. Dec. 13, 1985;230(4731):1242-6.
Nagrath, et al. Isolation of rare circulating tumour cells in cancer patients by microchip technology. Nature. 2007; 450: 1235-1241 (with Supplemental pp. 1-10).
Nannya, et al. A robust algorithm for copy No. detection using high-density oligonucleotide single nucleotide polymorphism genotyping arrays. Cancer Res. Jul. 15, 2005;65(14):6071-9.
Nelson, et al. Genotyping Fetal DNA by Non-invasive Means: Extraction From Maternal Plasma. Vox Sang. 2001;80:112-116.
Newcombe, R. G. Two-sided confidence intervals for the single proportion: comparison of seven methods. Statistics in Medicine. 1998; 17:857-872.
Ng, et al. "The Concentration of Circulating Corticotropin-releasing Hormone mRNA in Maternal Plasma Is Increased in Preeclampsia," Clinical Chemistiy, 2003, vol. 49, No. 5, 727-731.
Notice of Allowance and Issue Fee Due Dec. 9, 2010 issued in U.S. Appl. No. 11/701,686.
Notice of allowance dated Jan. 22, 2016 for U.S. Appl. No. 13/837,974.
Notice of allowance dated Jan. 26, 2015 for U.S. Appl. No. 13/835,926.
Notice of allowance dated Jun. 21, 2012 for U.S. Appl. No. 12/815,647.
Notice of allowance dated Oct. 5, 2012 for U.S. Appl. No. 11/763,421.
Notice of allowance dated Oct. 27, 2015 for U.S. Appl. No. 13/829,971.
Notice of allowance dated Dec. 23, 2011 for U.S. Appl. No. 12/230,628.
Notice of allowance dated Dec. 29, 2011 for U.S. Appl. No. 11/763,245.
Notice of allowance dated Jul. 12, 2011 with allowed claims for U.S. Appl. No. 12/393,803.
Oakey et al. Laminar Flow-Based Separations at the Microscale. Biotechnology Progress. 2002; pp. 1439-1442.
Office action (Ex parte Quayle) dated May 13, 2011 for U.S. Appl. No. 11/763,421.
Office Action dated Jan. 12, 2009 for U.S. Appl. No. 11/763,133.
Office action dated Jan. 26, 2015 for CA Application No. 2655272.
Office Action dated Jan. 27, 2010 for U.S. Appl. No. 11/701,686.
Office action dated Jan. 28, 2009 for U.S. Appl. No. 11/701,686.
Office action dated Jan. 28, 2014 for U.S. Appl. No. 13/835,926.
Office action dated Jan. 30, 2012 for Application No. CN 200780030309.3.
Office action dated Jan. 30, 2014 for U.S. Appl. No. 13/837,974.
Office action dated Feb. 4, 2010 for U.S. Appl. No. 11/067,102.
Office action dated Feb. 5, 2014 for U.S. Appl. No. 12/689,517.
Office action dated Feb. 15, 2011 for U.S. Appl. No. 11/763,426.
Office action dated Feb. 23, 2015 for U.S. Appl. No. 12/689,517.
Office action dated Mar. 3, 2009 for EP Application No. EP07763674.4.
Office action dated Mar. 4, 2009 for U.S. Appl. No. 11/228,454.
Office action dated Mar. 7, 2012 for U.S. Appl. No. 12/816,043.
Office action dated Mar. 7, 2013 for European Application No. 11182181.
Office action dated Mar. 11, 2010 for U.S. Appl. No. 11/763,245.
Office action dated Mar. 11, 2015 for U.S. Appl. No. 13/737,730.
Office action dated Mar. 15, 2016 for U.S. Appl. No. 12/751,940.
Office action dated Mar. 20, 2013 for U.S. Appl. No. 12/815,674.
Office action dated Mar. 20, 2014 for U.S. Appl. No. 12/816,043.
Office action dated Mar. 21, 2014 for U.S. Appl. No. 12/815,674.
Office action dated Mar. 29, 2011 for U.S. Appl. No. 11/763,245.
Office action dated Mar. 31, 2016 for U.S. Appl. No. 13/863,992.
Office action dated Apr. 4, 2008 for U.S. Appl. No. 11/067,102.
Office action dated Apr. 4, 2012 for EP Application No. 07784444.7.
Office action dated Apr. 4, 2013 for U.S. Appl. No. 12/689,517.
Office action dated Apr. 5, 2012 for U.S. Appl. No. 12/751,931.
Office action dated Apr. 7, 2015 for U.S. Appl. No. 13/829,971.
Office action dated Apr. 9, 2013 for U.S. Appl. No. 13/306,520.
Office action dated Apr. 12, 2012 for U.S. Appl. No. 12/815,647.
Office action dated Apr. 13, 2009 for U.S. Appl. No. 11/067,102.
Office action dated Apr. 23, 2015 for U.S. Appl. No. 12/751,940.
Office action dated Apr. 24, 2012 for EP Application No. 07784442.1.
Office action dated Apr. 25, 2011 for U.S. Appl. No. 12/393,803 with pending claims.
Office action dated Apr. 28, 2014 for U.S. Appl. No. 12/689,548.
Office action dated May 4, 2009 for U.S. Appl. No. 11/763,431.
Office action dated May 6, 2011 for U.S. Appl. No. 11/763,133.
Office action dated May 8, 2015 for U.S. Appl. No. 12/816,043.
Office action dated May 11, 2015 for U.S. Appl. No. 13/863,992.
Office action dated May 12, 2011 for U.S. Appl. No. 12/230,628.
Office action dated May 18, 2011 for U.S. Appl. No. 12/413,467.
Office action dated May 26, 2011 for U.S. Appl. No. 11/762,750.
Office action dated May 31, 2013 for U.S. Appl. No. 13/835,926.
Office action dated Jun. 3, 2013 for U.S. Appl. No. 13/306,640.
Office action dated Jun. 3, 2013 for U.S. Appl. No. 13/837,974.
Office action dated Jun. 4, 2012 for U.S. Appl. No. 11/762,747.
Office action dated Jun. 5, 2012 for U.S. Appl. No. 12/393,833.
Office action dated Jun. 5, 2013 for U.S. Appl. No. 12/751,940.
Office action dated Jun. 10, 2015 for U.S. Appl. No. 13/830,871.
Office action dated Jun. 14, 2010 for U.S. Appl. No. 11/763,426.
Office action dated Jun. 15, 2007 for U.S. Appl. No. 11/067,102.
Office action dated Jun. 18, 2012 for U.S. Appl. No. 12/751,908.
Office action dated Jun. 18, 2012 for U.S. Appl. No. 12/751,940.
Office action dated Jun. 22, 2012 for Application No. AU 2007260676.
Office action dated Jul. 2, 2010 for EP Application No. 07784442.1.
Office action dated Jul. 9, 2012 for U.S. Appl. No. 11/762,750.
Office action dated Jul. 10, 2009 for U.S. Appl. No. 11/763,421.
Office action dated Jul. 10, 2012 for U.S. Appl. No. 13/433,232.
Office action dated Jul. 16, 2015 for U.S. Appl. No. 13/837,974.
Office action dated Jul. 21, 2015 for U.S. Appl. No. 12/689,548.
Office action dated Jul. 26, 2011 for U.S. Appl. No. 11/763,245.
Office action dated Jul. 29, 2014 for U.S. Appl. No. 13/835,926.
Office action dated Aug. 1, 2008 for U.S. Appl. No. 11/067,102.
Office action dated Aug. 1, 2012 for U.S. Appl. No. 12/815,674.
Office action dated Aug. 1, 2014 for U.S. Appl. No. 12/816,043.
Office action dated Aug. 2, 2010 for EP Application No. 07784444.7.
Office action dated Aug. 7, 2013 for U.S. Appl. No. 13/863,992.
Office action dated Aug. 16, 2016 for U.S. Appl. No. 13/863,992.
Office action dated Aug. 19, 2015 for U.S. Appl. No. 12/689,517.
Office action dated Aug. 27, 2010 for U.S. Appl. No. 11/762,747.
Office action dated Aug. 29, 2014 for U.S. Appl. No. 13/837,974.
Office Action dated Sep. 8, 2010 for U.S. Appl. No. 11/701,686.
Office action dated Sep. 10, 2010 for U.S. Appl. No. 11/762,750.
Office Action dated Sep. 11, 2009 for U.S. Appl. No. 11/701,686.
Office action dated Sep. 14, 2012 for U.S. Appl. No. 12/393,833.
Office action dated Sep. 17, 2010 for U.S. Appl. No. 11/067,102.
Office action dated Sep. 17, 2014 for U.S. Appl. No. 13/863,992.
Office action dated Sep. 18, 2015 for U.S. Appl. No. 12/816,043.
Office action dated Sep. 22, 2011 for U.S. Appl. No. 12/815,647.
Office action dated Sep. 23, 2009 for EP Application No. EP07763674.4 with pending claims.
Office action dated Sep. 23, 2009 for EP Application No. EP07763674.4.

(56) References Cited

OTHER PUBLICATIONS

Office action dated Sep. 27, 2010 for U.S. Appl. No. 12/413,485.
Office action dated Sep. 27, 2013 for U.S. Appl. No. 12/816,043.
Office action dated Oct. 24, 2011 for U.S. Appl. No. 11/762,747.
Office action dated Oct. 25, 2012 for U.S. Appl. No. 12/816,043.
Office action dated Oct. 29, 2010 for U.S. Appl. No. 12/230,628.
Office action dated Nov. 3, 2009 for U.S. Appl. No. 11/763,133.
Office action dated Nov. 7, 2014 for U.S. Appl. No. 13/831,342.
Office action dated Nov. 24, 2014 for U.S. Appl. No. 12/689,548.
Office action dated Dec. 1, 2009 for U.S. Appl. No. 11/763,426.
Office action dated Dec. 2, 2008 for U.S. Appl. No. 11/762,747.
Office action dated Dec. 3, 2008 for U.S. Appl. No. 11/763,426.
Office action dated Dec. 10, 2013 for CA Application No. 2655272.
Office action dated Dec. 10, 2014 for U.S. Appl. No. 12/751,940.
Office action dated Dec. 10, 2015 for U.S. Appl. No. 13/830,871.
Office action dated Dec. 12, 2014 for U.S. Appl. No. 13/738,268.
Office action dated Dec. 13, 2013 for U.S. Appl. No. 13/306,698.
Office action dated Dec. 16, 2013 for U.S. Appl. No. 13/863,992.
Office action dated Dec. 31, 2009 for U.S. Appl. No. 11/763,421.
Office action dated Dec. 31, 2009 for U.S. Appl. No. 11/762,750.
Office action dated Dec. 31, 2011 for U.S. Appl. No. 11/763,421.
Olson, et al. A Common Language for Physical Mapping of the Human Genome. "A common language for physical mapping of the human genome." Science 245.4925 (1989): 1434-1435. Sep. 29, 1989.
Olson, et al. An In Situ Flow Cytometer for the Optical Analysis of Individual Particles in Seawater. Available at http://www.whoi.edu/science/B/Olsonlab/insitn2001.htm. Accessed Apr. 24, 2006.
Oosterwijk, et al. Prenatal diagnosis of trisomy 13 on fetal cells obtained from maternal blood after minor enrichment. Prenat Diagn, 1998;18(10):1082-5.
Ottesen, et al. Microfluidic Digital PCR Enables Multigene Analysis of Individual Environmental Bacteria. Science. Dec. 1, 2006; 314(5804):1464-1467. (Abstract only).
Owen, et al. High gradient magnetic separation of erythrocytes. Biophys. J. 1978; 22:171-178.
Paez, et al. Genome coverage and sequence fidelity of phi29 polymerase-based multiple strand displacement whole genome amplification. Nucleic Acids Res. May 18, 2004;32(9):e71.
Pallavicini, et al. Analysis of fetal cells sorted from maternal blood using fluorescence in situ hybridization. The American Journal of Human Genetics. Oct. 1992. Supplemental to vol. 51, No. 4: 1031.
Parano, et al. Fetal Nucleated red blood cell counts in peripheral blood of mothers Down Syndrome fetus. Neuropediatrics. 2001; 32(3):147-149, (Abstract only).
Parano, et al. Noninvasive Prenatal Diagnosis of Chromosomal Aneuploidies by and Analysis of Fetal Cells from Maternal Blood. Am. J. Med. Genet. 101:262-7 (2001).
Paterlini-Brechot, et al. Circulating tumor cells (CTC) detection: Clinical impact and future directions. Cancer Letter, 2007, (In press, 25 pages.) Available at www.sciencedirect.com.
Pathak, et al. Circulating Cell-Free DNA in Plasma/Serum of Lung Cancer Patients as a Potential Screening and Prognostic Tool, Oct. 2006, Clin. Chem.52(10): 1833-42.
Paul, et al. Single-molecule dilution and multiple displacement amplification for molecular haplotyping. Biotechniques. 2005; 38(4):553-4, 556, 558-9.
Pawlik, et al. Prodrug Bioactivation and Oncolysis of Diffuse Liver Metastases by a Herpes Simplex Virus 1 Mutant that Expresses the CYP2B1 Transgene. Cancer, 2002;95:1171-81.
Peixoto, et al. Quantification of multiple gene expression in individual cells. Genome Res. Oct. 2004;14(10A):1938-47.
Pending Claims and Preliminary Amendment filed Nov. 19, 2010 for U.S. Appl. No. 11/763,133.
Pending claims and preliminary amendment filed Dec. 10, 2010 for U.S. Appl. No. 11/763,245.
Pending claims dated Jun. 10, 2016 for U.S. Appl. No. 13/830,871.
Pending claims dated Sep. 24, 2014 for U.S. Appl. No. 13/738,268.
Pending claims filed with the USPTO on Apr. 26, 2010 for U.S. Appl. No. 11/067,102.

Peng, et al. Real-time detection of gene expression in cancer cells using molecular beacon imaging: new strategies for cancer research. Cancer Res. 2005; 65(5):1909-17.
Pertl, et al. "Fetal DNA in Maternal Plasma: Emerging Clinical Applications," Obstetrics and Gynecology, Sep. 2001, vol. 98, No. 3, 483-490.
Pertl, et al. Detection of Male and Female DNA in Maternal Plasma by Multiplex Fluorescent Polymerase Chain Reaction Amplification of Short Tandem Repeats. Jan. 2000. Hum. Genet. 106(1):45-9.
Petersen, et al. The Promise of Miniaturized Clinical Diagnostic Systems. IVD Technol. 4:43-49 (1998).
Pfaffl, et al. Relative expression software tool (REST) for group-wise comparison and statistical analysis of relative expression results in real-time PCR. Nucleic Acids Res. May 1, 2002;30(9):e36.
Pinkel, et al. Cytogenetic Analysis Using Quantitative, High-sensitivity, Fluorescence Hybridization, Genetics. 1986;83:2934-2938.
Pinkel, et al. Fluorescence in situ Hybridization with Human Chromosome-specific Libraries: Detection of Trisomy 21 and Translocations of Chromosome 4. Genetics.1988;85:9138-9142.
Pinkel, et al. Detection of structural chromosome aberrations in metaphase in metaphase spreads and interphase nuclei by in situ hybridization high complexity probes which stain entire human chromosomes. The American Journal of Human Genetics. Sep. 1988. Supplemental to vol. 43, No. 3: 0471.
Pinzani, et al. Isolation by size of epithelial tumor cells in peripheral blood of patients with breast cancer: correlation with real-time reverse transcriptase-polymerase chain reaction results and feasibility of molecular analysis by laser microdissection. Hum Pathol. 2006; 37(6):711-8.
Pohl et al. Principle and applications of digital PCR. Expert Rev Mol Diagn. Jan. 2004;4(1):41-7.
Poon, et al. "Circulating fetal DNA in maternal plasma," Clinical Chimica Acta, 2001, vol. 313, 151-155.
Potti, et al. Genomic signatures to guide the use of chemotherapeutics. Nat Med. 2006; 12(11):1294-1300.
Preliminary Amendments to the Claims. Filed Jul. 11, 2013 with U.S. Patent Office for U.S. Appl. No. 13/738,268.
Preliminary Amendments to the Claims. Filed Jul. 3, 2013 with U.S. Patent Office for U.S. Appl. No. 13/830,871.
Price, et al. Prenatal Diagnosis with Fetal Cells Isolated from Maternal Blood by Multiparameter Flow Cytometry. Am. J. Obstet. Gynecol. 1991; 165:1731-7.
Prieto, et al. Isolation of fetal nucleated red blood cells from maternal blood in normal and aneuploid pregnancies. Clin Chem Lab Med. Jul. 2002;40(7):667-72.
Product literature for GEM, a system for blood testing: GEM Premier 3000. Available at http://www.ilus.com/premier_gem3000_iqm.asp. Accessed Apr. 24, 2006.
Pruitt, et al. RefSeq and LocusLink: NCBI gene-centered resources. Nucl. Acids Res. (2001) vol. 29 No. 1: 137-140. DOI: 10.1093/nar/29.1.137.
Purwosunu, et al. Clinical potential for noninvasive prenatal diagnosis through detection of fetal cells in maternal blood. Taiwan J Obstet Gynecol. Mar. 2006;45(1):10- 20.
Raeburn, P. Fetal Cells Isolated In Women's Blood. Associated Press (Jul. 28, 1989) [electronic version].
Rahil, et al. Rapid detection of common autosomal aneuploidies by quantitative fluorescent PCR on uncultured amniocytes, European Journal of Human Genetics, 2002, vol. 10, 462-466.
REPLI-g® Mini and Midi Kits pamphlet from Qiagen (Oct. 2005).
Request for Continued Examination by applicant with claim set dated Mar. 26, 2010 in Response to Final Office Action dated Nov. 3, 2009 for U.S. Appl. No. 11/763,133.
Request for Continued Examination by applicant with claim set dated Mar. 26, 2010 in Response to Final Office Action dated Dec. 1, 2009 for U.S. Appl. No. 11/763,426.
Response dated Nov. 24, 2010 to Office action dated Jun. 14, 2010 with Pending Claims for U.S. Appl. No. 11/763,426.
Response filed Dec. 26, 2012 with claims for U.S. Appl. No. 12/393,833.
Rickman, et al. Prenatal diagnosis by array-CGH. European Journal of Medical Genetics. 2005; 48:232-240.

(56) References Cited

OTHER PUBLICATIONS

Rolle, et al. Increase in number of circulating disseminated epithelia cells after surgery for nonsmall cell lung cancer monitored by MAINTRAC is a predictor for relapse: a preliminary report. World Journal of Surgical Oncology. 2005; 9 pages.
Rosato, M. Verinata Health, Inc. 's Preliminary Patent Owner Response Pursuant to 37 C.F.R. §42.107(a). Dated Jul. 29, 2013. For Case IPR2013-00276. U.S. Pat. No. 8,318,430.
Ruan, et al. Identification of clinically significant tumor antigens by selecting phage antibody library on tumor cells in situ using laser capture microdissection. Molecular & Cellular Proteomics. 2006; 5(12): 2364-73.
Sakhnini, et al. Magnetic behavior of human erythrocytes at different hemoglobin states. Eur Biophys J. Oct. 2001;30(6):467-70.
Saleeba, et al. Chemical cleavage of mismatch to detect mutations. Methods Enzymol. 1993;217:286-95.
Samura, et al. Diagnosis of trisomy 21 in fetal nucleated erythrocytes from maternal blood by use of short tandem repeat sequences. Clin. Chem, 2001; 47(9)4622-6.
Samura, et al. Female fetal cells in maternal blood: use of DNA polymorphisms to prove origin. Hum. Genet. 2000;107(1):28-32.
Sato, et al. Individual and Mass Operation of Biological Cells Using Micromechanical Silicon Devices. Sensors and Actuators. 1990;A21-A23:948-953.
Schaefer, et al. The Clinical Relevance of Nucleated Red Blood Cells counts. Sysmex Journal International. 2000; 10(2):59-63.
Schroder, et al. Fetal Lymphocytes in the Maternal Blood. The Journal of Hematolog:Blood. 1972;39:153-162.
Sehnert, et al. Optimal Detection of Fetal Chromosomal Abnormalities by Massively Parallel DNA Sequencing of Cell-Free Fetal DNA from Maternal Blood. Clin Chem. Apr. 25, 2011. [Epub ahead of print].
Sethu, et al. Continuous Flow Microfluidic Device for Rapid Erythrocyte Lysis. Anal. Chem. 76:6247-6253 (2004).
Shen, et al. High-throughput SNP genotyping on universal bead arrays. Mutat. Res. 2005; 573:70-82.
Shendure, et al. Accurate multiplex polony sequencing ofan evolved bacterial genome. Science. 2005;309:1728-32.
Shendure, et al. Next-generation DNA sequencing. Nature. 2008; 26(10):1135-1145.
Sherlock, et al. Assessment of diagnostic quantitative fluorescent multiplex polymerase chain reaction assays performed on single cells. Ann. Hum. Genet. 1998; 62:9-23.
Sitar, et al. The Use of Non-Physiological Conditions to Isolate Fetal Cells from Maternal Blood. Exp. Cell. Res. 2005; 302:153-61.
Sohda, et al. The Proportion of Fetal Nucleated Red Blood Cells in Maternal Blood: Estimation by FACS Analysis. Prenat. Diagn, 1997; 17:743-52.
Solexa Genome Analysis System. 2006; 1-2.
Sparkes, et al. "New Molecular Techniques for the Prenatal Detection of Chromosomal Aneuploidy," JOGC, Jul. 2008, No. 210, 617-621.
Stipp, D. IG Labs Licenses New Technology for Fetal Testing. The Wall Street Journal. Aug. 10, 1990:B5.
Stoecklein, et al. SCOMP is superior to degenerated oligonucleotide primed- polymerase chain reaction for global amplification of minute amounts of DNA from microdissected archival tissue samples. Am J Pathol. 2002; 161(1):43-51.
Stoughton, et al. Data-adaptive algorithms for calling alleles in repeat polymorphisms. Electrophoresis. 1997;18(1):1-5.
Su, et al. Human Urine Contains Small, 150 to 250 Nucleotide-Sized, Soluble DNA Derived from the Circulation and may be Useful in the Detection of Colorectal Cancer. May 2005. J. Mol. Diagn. 6(2):101-7.
Sun, et al. Whole-genome amplification: relative efficiencies of the current methods. Leg Med. 2005; 7(5):279-86.
Supplemental Amendment and Transmittal of Terminal Disclaimer dated Oct. 18, 2011 for U.S. Appl. No. 12/230,628.
Swarup, et al. Circulating (cell free) nucleic acids—A promising, non-invasive tool for early detection of several human diseases. 2007 FEBS Letters 581:795-799.
Sykes, et al. Quantitation of targets for PCR by use ofl imiting dilution. Biotechniques. Sep. 1992;13(3):444-9.
Tanaka, et al. "Genome-wide expression profiling of mid-gestation placenta and embryo using a 15,000 mouse developmental cDNA microarray," PNAS, Aug. 2000, vol. 97, No. 16, 9127-9132.
Tettelin, et al. The nucleotide sequence of *Saccharomyces cerevisiae* chromosome VII. Nature. May 29, 1997;387(6632 Suppl):81-4.
Thomas, et al. Specific Binding and Release of Cells from Beads Using Cleavable Tettrametric Antibody Complexes. Journal of Immunological Methods 1989;120:221-231.
Thomas, et al. Sensitive Mutation Detection in Heterogeneous Cancer Specimens by Massively Parallel Picoliter Reactor Sequencing, Jul. 2006, Nature Medicine. 12(7):852-855.
Tibbe, et al. Statistical considerations for enumeration of circulating tumor cells. Cytometry A. Mar. 2007;71(3):154-62.
Toner, et al. Blood-on-a-Chip. Annu. Rev. Biomed. Eng. 7:77-103, C1-C3 (2005).
Trask, et al. Detection of DNA Sequences and Nuclei in Suspension by In Situ Hybridization and Dual Beam Flow Cytometiy. Science. 1985;230:1401-1403.
Troeger, et al. Approximately half of the erythroblasts in maternal blood are of fetal origin. Mol Hum Reprod. 1999; 5(12):1162-5.
Tufan, et al., Analysis of Cell-Free Fetal DNA from Maternal Plasma and Serum Using a Conventional Multiplex PCR: Factors Influencing Success. 2005, Turk. J. Med. Sci. 35:85-92.
Uitto, et al. Probing the fetal genome: progress in non-invasive prenatal diagnosis. Trends Mol Med. Aug. 2003;9(8):339-43.
Van Raamsdonk, et al. Optimizing the detection of nascent transcripts by RNA fluorescence in situ hybridization, Nucl. Acids. Res. 2001; 29(8):e42.
Venter, et al. The Sequence of the Human Genome. Science Feb. 16, 2001; vol. 291 No. 5507 pp. 1304-1351 DOI: 10.1126/science.1058040.
Verinata Health. Complaint for Patent Infringement. Case: 12-cv-05501-SI; Dated Oct. 25, 2012.
Verinata Health. Plaintiffs' Opposition to Defendants' Motion to Dismiss Plaintiffs' Claims for Patent Infringement Against Laboratory Corporation of America and Claims for Enhanced Damages Against All Defendants. Case: 12-CV-05501-SI; Dated Jan. 25, 2013.
Verinata Health: Joint Claim Construction and Prehearing Statement. Case: 12-cv-05501-SI; Dated May 3, 2013.
Voelkerding, et al. Digital fetal aneuploidy diagnosis by next-generation sequencing. Clin Chem. Mar. 2010;56(3):336-8.
Vogelstein, et al. "Digital PCR." Proc Natl. Acad Sci. USA, Aug. 1999, vol. 96., 9236-9241.
Voldberg, et al. Epidermal growth factor receptor (EGFR) and EGFR mutations, function and possible role in clinical trials. Ann Oncol. Dec. 1997;8(12):1197-206.
Volkmuth, et al. DNA electrophoresis in microlithographic arrays. Nature. 1992; 358:600-602.
Volkmuth, et al. Observation of Electrophoresis of Single DNA Molecules in Nanofabricated Arrays. Presentation at joint annual meeting of Biophysical Society and the American Society for Biochemistiy and Molecular Biology, Feb. 9-13, 1992.
Von Eggeling, et al. Determination of the origin of single nucleated cells in maternal circulation by means of random PCR and a set of length polymorphisms. Hum Genet. Feb. 1997;99(2):266-70.
Vona, et al. Enrichment, immunomorphological, and genetic characterization of fetal cells circulating in maternal blood. Am J Pathol. Jan. 2002;160(1):51-8.
Voss, et al. Efficient low redundancy large-scale DNA sequencing at EMBL. Journal of Biotechnology, vol. 41, Issues 2-3, Jul. 31, 1995, pp. 121-129.
Voullaire, et al. Detection of aneuploidy in single cells using comparative genomic hybridization, Prenat Diagn. 1999; 19(9):846-51.
Vrettou, et al. Real-time PCR for single-cell genotyping in sickle cell and thalassemia syndromes as a rapid, accurate, reliable, and

(56) References Cited

OTHER PUBLICATIONS widely applicable protocol for preimplantation genetic diagnosis. Human Mutation, 2004; 23(5):513-21.
Wachtel, et al. Fetal Cells in the Maternal Circulation: Isolation by Multiparameter Flow Cytometry and Confirmation by Polymerase Chain Reaction. Human Reproduction. 1991;6:1466-1469.
Wang, et al. Allele quantification using molecular inversion probes (MIP). Nucleic Acids Research. 2005; 33(21); e183 (14 pages).
Wapner, et al. First-trimester screening for trisomies 21 and 18. N. Engl. J. Med. 2003; 349:1405-1413.
Warren, et al. Transcription factor profiling in individual hematopoietic progenitors by digital RT-PCR. PNAS. Nov. 21, 2006; 103(47):17807-17812.
Washizu, et al. Handling Biological Cells Utilizing a Fluid Integrated Circuit. IEEE Industry Applications Society Annual Meeting Presentations. Oct. 2-7, 1988;: 1735-40.
Washizu, et al. Handling Biological Cells Utilizing a Fluid Integrated Circuit. IEEE Transactions ofIndustry Applications. 1990; 26: 352-8.
Weigl, et al. Microfluidic Diffusion-Based Separation and Detection. Science. 1999; pp. 346-347.
Wheeler, et al. The complete genome of an individual by massively parallel DNA sequencing. Nature 452, 872-876 (Apr. 17, 2008) I DOI:10.1038/nature06884; Received Dec. 3, 2007; Accepted Mar. 4, 2008.
White, et al. Digital PCR provides sensitive and absolute calibration for high throughput sequencing, BMC Genomics. Mar. 19, 2009;10:116.
Williams, et al. Comparison of cell separation methods to enrich the proportion of fetal cells in material blood samples. The American Journal of Human Genetics. Oct. 1992. Supplemental to vol. 51, No. 4: 1049.
Wright, et al. The use of cell-free fetal nucleic acids in maternal blood for non-invasive prenatal diagnosis. Hum Reprod Update. Jan.-Feb. 2009;15(1):139-51.
Xiong, et al. "A simple, rapid, high-fidelity and cost-effective PCR-based two-step DNA synthesis method for long gene sequences," Nucleic Acids Research, Apr. 19.
Yang, et al. Prenatal diagnosis of trisomy 21 with fetal cells i maternal blood using comparative genomic hybridization. Fetal DiagnTher. 2006; 21:125-133.
Yang, et al. Rapid Prenatal Diagnosis of Trisomy 21 by Real-time Quantitative Polymerase Chain Reaction with Amplification of Small Tandem Repeats and S1O0B in Chromosome 21. Yonsei Medical Journal, 2005, vol. 46, No. 2, 193-197.
Yu, et al. Objective Aneuploidy Detection for Fetal and Neonatal Screening Using Comparative Genomic Hybridization (CGH), Cytometry. 1997; 28(3): 191-197, (Absbract).
Zavala, et al. Genomic GC content prediction in prokaryotes from a sample of genes. Gene. Sep. 12, 2005;357(2):137-43.
Zhang, et al. Whole genome amplification from a single cell: implications for genetic analysis. Proc Natl Acad Sci US A. Jul. 1, 1992;89(13):5847-51.
Zhao, et al. An integrated view of copy number and allelic alterations in the cancer genome using single nucleotide polymorphism arrays. Cancer Res. May 1, 2004;64(9):3060-71.
Zhen, et al. Poly-FISH: a technique of repeated hybridizations that improves cytogenetic analysis of fetal cells in maternal blood. Prenat Diagn. 1998; 18(11):1181-5.
Zheng, et al. Fetal cell identifiers: results of microscope slide-based immunocytochemical studies as a function of gestational age and abnormality. Am J Obstet Gynecol. May 1999;180(5):1234-9.
Zhu, et al. Single molecule profiling of alternative pre-mRNA splicing. Science. Aug. 8, 2003;301(5634):836-8.
Zimmerman et al. QIAGEN News. 2003. e12. Available via uri: <b2b.qiagen.com/literature/qiagennews/weeklyarticle/apr03/e12/default.aspx>.
Zimmerman, et al. Novel real-time quantitative PCR test for trisomy 21. Jan. 1, 2002. Clinical Chemistry, American Association for Clinical Chemistry. 48:(2) 362-363.
Zimmermann, Bernhard. "Molecular Diagnosis in Prenatal Medicine," Ph.D. Thesis, 2004.

Microposts and cells

Antibody coated posts

Typical allele strengths at different loci.
First row – maternal sample.
Second row – mixed sample containing maternal and fetal DNA.
Third row – mixed sample assuming fetal trisomy at Loci 1 and 2.
Excess signal from the extra chromosome copy is indicated in dashed red.

Concept of rank ordering of allele strengths.
Assuming a bi-allelic maternal sample, a third allele significantly above the noise level can be identified as paternal.

Histogram of paternal allele strength, normalized to average of maternal alleles.

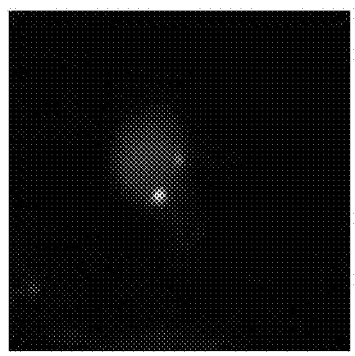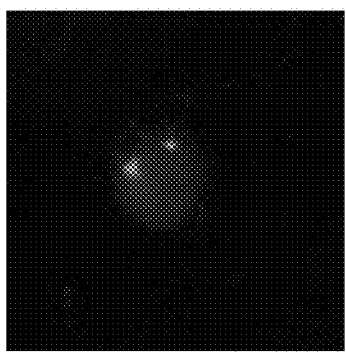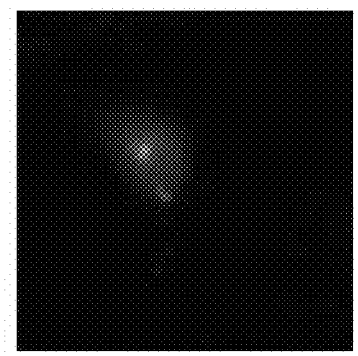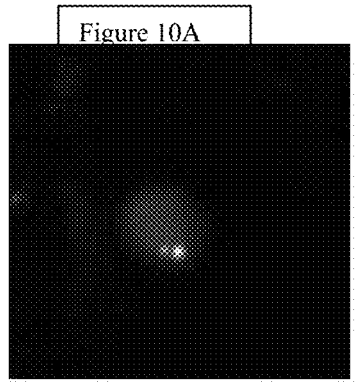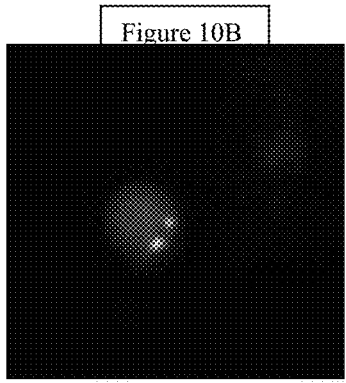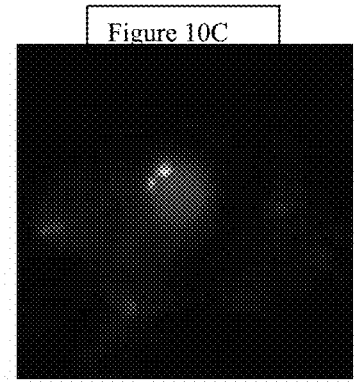
Figure 10A-F (Blue= nucleus, Red = X chromosome, Green = Y chromosome)

chip inlet array outlet

FETAL ANEUPLOIDY DETECTION BY SEQUENCING

CROSS-REFERENCE

This application is a continuation U.S. Patent application of Ser. No. 13/794,503, filed on Mar. 11, 2013, which is a continuation application of U.S. patent application Ser. No. 12/751,940, filed on Mar. 31, 2010, now abandoned, which is a continuation application of U.S. patent application Ser. No. 11/763,133, filed Jun. 14, 2007, now abandoned, which claims the benefit of U.S. Provisional Application No. 60/804,816, filed Jun. 14, 2006 and U.S. Provisional Application No. 60/820,778, filed Jul. 28, 2006, which are incorporated herein by reference in their entireties.

BACKGROUND OF THE INVENTION

Analysis of specific cells can give insight into a variety of diseases. These analyses can provide non-invasive tests for detection, diagnosis and prognosis of diseases, thereby eliminating the risk of invasive diagnosis. For instance, social developments have resulted in an increased number of prenatal tests. However, the available methods today, amniocentesis and chorionic villus sampling (CVS) are potentially harmful to the mother and to the fetus. The rate of miscarriage for pregnant women undergoing amniocentesis is increased by 0.5-1%, and that figure is slightly higher for CVS. Because of the inherent risks posed by amniocentesis and CVS, these procedures are offered primarily to older women, i.e., those over 35 years of age, who have a statistically greater probability of bearing children with congenital defects. As a result, a pregnant woman at the age of 35 has to balance an average risk of 0.5-1% to induce an abortion by amniocentesis against an age related probability for trisomy 21 of less than 0.3%.

Some non-invasive methods have already been developed to diagnose specific congenital defects. For example, maternal serum alpha-fetoprotein, and levels of unconjugated estriol and human chorionic gonadotropin can be used to identify a proportion of fetuses with Down's syndrome, however, these tests are not one hundred percent accurate. Similarly, ultrasonography is used to determine congenital defects involving neural tube defects and limb abnormalities, but is useful only after fifteen weeks' gestation.

The methods of the present invention allow for the detection of fetal cells and fetal abnormalities when fetal cells are mixed with a population of maternal cells, even when the maternal cells dominate the mixture.

SUMMARY OF THE INVENTION

The presence of fetal cells within the blood of pregnant women offers the opportunity to develop a prenatal diagnostic that replaces amniocentesis and thereby eliminates the risk of today's invasive diagnosis. However, fetal cells represent a small number of cells against the background of a large number of maternal cells in the blood which make the analysis time consuming and prone to error. Current technologies and protocols for highly parallel SNP detection with DNA microarray readout result in inaccurate calls when there are too few starting DNA copies or when a particular allele represents a small fraction in the population of input DNA molecules.

The present invention relates to methods for detecting a fetal abnormality by determining the ratio of the abundance of one or more maternal alleles to the abundance of one or more paternal alleles in the genomic DNA of a sample. The genomic region includes a single nucleotide polymorphism (SNP), which can preferably be an informative SNP. The SNP can be detected by methods that include using a DNA microarray, bead microarray, or high throughput sequencing. In some embodiments, determining the ratio involves detecting an abundance of a nucleotide base at a SNP position. In other embodiments, determining the ratio also comprises calculating error rate based amplification. Prior to determining the abundance of allele(s), the sample can be enriched for fetal cells.

The method of detection is provided by highly parallel SNP detection that can be used to determine the ratios of abundance of maternal and paternal alleles at a plurality of genomic regions present in the sample. In some embodiments, the ratios of abundance are determined in at least 100 genomic regions, which can comprise a single locus, different loci, a single chromosome, or different chromosomes. In some embodiments, a first genomic region (SNP) analyzed is in a genomic region suspected of being trisomic or is trisomic and a second genomic region (SNP) analyzed is in a non-trisomic region or a region suspected of being non-trisomic. The ratio of alleles in the first genomic region can then be compared to the ratio of alleles in the second genomic region, and in some embodiments, the comparison is made by determining the difference in the means of the ratios in the first and second genomic regions. An increase in paternal abundance can be indicative of paternal trisomy, while an increase in maternal abundance can be indicative of maternal trisomy. Alternatively, an increase in paternal abundance or maternal abundance of one or more alleles is indicative of partial trisomy. The first and second genomic regions can be on the same or different chromosomes.

In an embodiment, the invention provides for a method for detecting a fetal abnormality comprising comparing an abundance of one or more maternal alleles in a first genomic region in a maternal blood sample, where said genomic region is suspected of trisomy with an abundance of one or more maternal alleles in a second genomic region in said blood sample wherein said second genomic region is non-trisomic. Up to 20 ml of blood can be used to detect the fetal abnormality. The first genomic region that is suspected of trisomy and the second genomic region that is a non-trisomic region can each be present on chromosomes 13, 18, 21 and on the X chromosome.

In some embodiments, a ratio of the abundance of the maternal alleles in the first genomic region to the abundance of the maternal alleles in the second genomic region can be determined and compared to a second ratio obtained for a control sample. The control sample can comprise a diluted portion of the maternal sample, which can be diluted by a factor of at least 1,000.

In some embodiments, detecting the fetal abnormality further involves estimating the number of fetal cells present in the maternal sample. This can be performed by, e.g., ranking the alleles detected according to their abundance. The ranking can then be used to determine an abundance of one or more paternal alleles. In some embodiments, data models can be fitted for optimal detection of aneuploidy. The methods herein can be used to identify monoploidy, triploidy, tetraploidy, pentaploidy and other multiples of the normal haploid state. For example, the data models can be used to determine estimates for the fraction of fetal cells present in a sample and for detecting a fetal abnormality or condition.

In some embodiments, the abundance of one or more paternal alleles can be compared to the abundance of the maternal alleles at one or more genetic regions. In other embodiments, one or more ratios of the abundance of the paternal allele(s) to the abundance of the maternal allele(s) at one or more genetic regions can be compared with an estimate fraction of fetal cells. A statistical analysis can be performed on the one or more ratios of the abundance of paternal alleles to the abundance of the maternal alleles to determine the presence of fetal DNA in the sample with a level of confidence that exceeds 90%.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A-10F illustrate isolated fetal cells confirmed by the reliable presence of male Y chromosome.

DETAILED DESCRIPTION OF THE INVENTION

The methods herein are used for detecting the presence and condition of fetal cells in a mixed sample wherein the fetal cells are at a concentration of less than 90, 80, 70, 60, 50, 40, 30, 20, 10, 5 or 1% of all cells in the sample at a concentration less than 1:2, 1:4, 1:10, 1:50, 1:100, 1:1000, 1:10,000, 1:100,000, 1,000,000, 1:10,000,000 or 1:100,000,000 of all cells in the sample.

Figure 1:
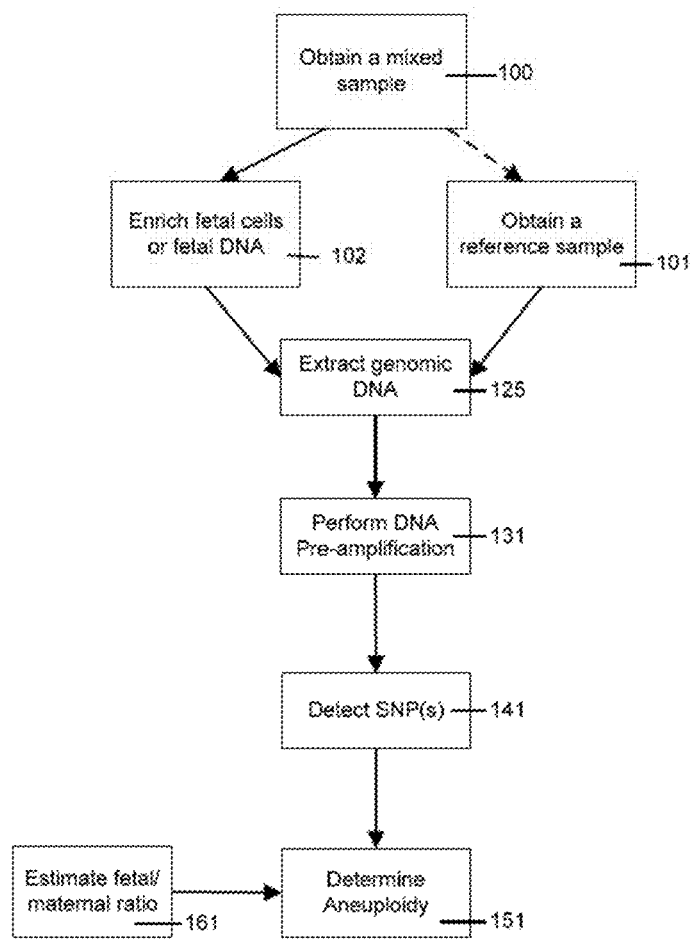
FIG. 1 illustrates an overview of the process of the invention.
Figure 2A:
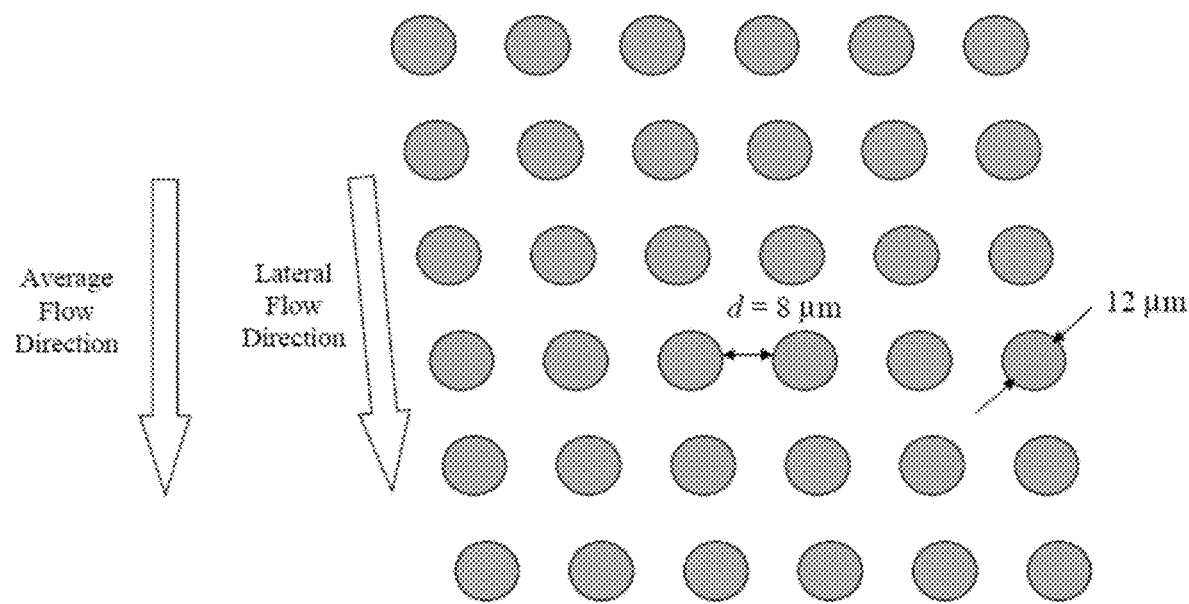
FIGS. 2A-2D illustrates one embodiment of a size-based separation module.
Figure 2B:
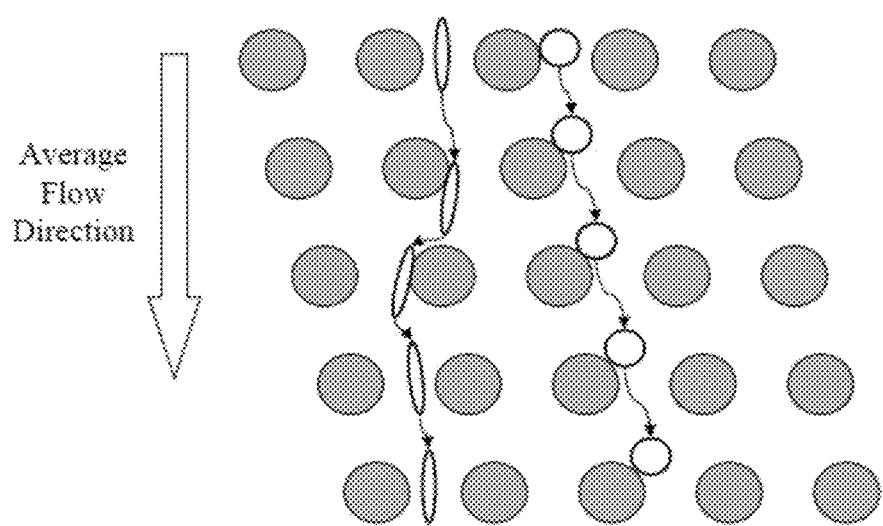
Figure 2C:
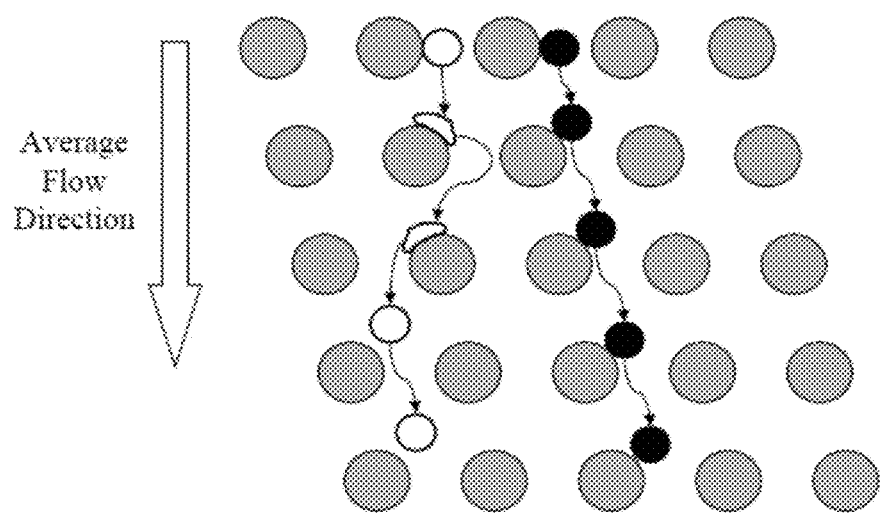
Figure 2D:
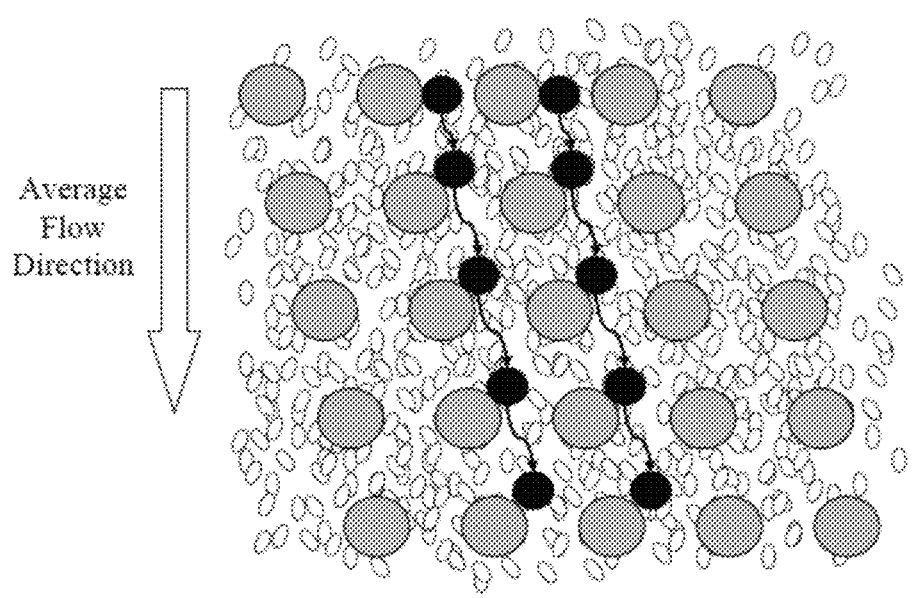

FIG. 1 illustrates an overview of the methods and systems herein.

In step 100, a sample to be analyzed for rare cells (e.g. fetal cells) is obtained from an animal. Such animal can be suspected of being pregnant, pregnant, or one that has been pregnant. Such sample can be analyzed by the systems and methods herein to determine a condition in the animal or fetus of the animal. In some embodiments, the methods herein are used to detect the presence of a fetus, sex of a fetus, or condition of the fetus. The animal from whom the sample is obtained can be, for example, a human or a domesticated animal such as a cow, chicken, pig, horse, rabbit, dog, cat, or goat. Samples derived from an animal or human include, e.g., whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid.

To obtain a blood sample, any technique known in the art may be used, e.g. a syringe or other vacuum suction device. A blood sample can be optionally pre-treated or processed prior to enrichment. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a cross-linking reagent.

When a blood sample is obtained, a preservative such an anti-coagulation agent and/or a stabilizer is often added to the sample prior to enrichment. This allows for extended time for analysis/detection. Thus, a sample, such as a blood sample, can be enriched and/or analyzed under any of the methods and systems herein within 1 week, 6 days, 5 days, 4 days, 3 days, 2 days, 1 day, 12 his, 6 hrs, 3 hrs, 2 hrs, or 1 hr from the time the sample is obtained.

A blood sample can be combined with an agent that selectively lyses one or more cells or components in a blood sample. For example, fetal cells can be selectively lysed releasing their nuclei when a blood sample including fetal cells is combined with deionized water. Such selective lysis allows for the subsequent enrichment of fetal nuclei using, e.g., size or affinity based separation. In another example, platelets and/or enucleated red blood cells are selectively lysed to generate a sample enriched in nucleated cells, such as fetal nucleated red blood cells (fnRBC) and material red nucleated blood cells (mnRBC). The fnRBCs can subsequently be separated from the mnRBCs using, e.g., antigen-i affinity or differences in hemoglobin When obtaining a sample from an animal (e.g., blood sample), the amount can vary depending upon animal size, its gestation period, and the condition being screened. Up to 50, 40, 30, 20, 10, 9, 8, 7, 6, 5, 4, 3, 2, or 1 mL of a sample is obtained. The volume of sample obtained can be 1-50, 2-40, 3-30, or 4-20 mL. Alternatively, more than 5, 10, 15, 20, 25, 30, 35, 40, 45, 50, 55, 60, 65, 70, 75, 80, 85, 90, 95 or 100 mL of a sample is obtained.

To detect fetal abnormality, a blood sample can be obtained from a pregnant animal or human within 36, 24, 22, 20, 18, 16, 14, 12, 10, 8, 6 or 4 weeks of gestation.

In step 101, a reference or control sample is obtained by any means known in the art. A reference sample is any sample that consists essentially of, or only of, non-fetal cells or non-fetal DNA. A reference sample is preferably a maternal only cell or DNA sample. In some embodiment, a reference sample is a maternal only blood sample. When obtaining a reference sample such as a maternal blood sample from a pregnant female, or one suspected of being pregnant or the sample can be diluted enough to ensure that <<1 fetal cell is expected in the sample. Dilution can be by a factor of about 10 to 1000 fold, or by a factor of greater than 5, 10, 50, 100, 200, 500 to 1000 fold. Alternatively, white blood cells can be obtained from the same organism from whom the mixed sample is obtained. In some cases, the reference sample is obtained by deleting a portion of the mixed sample.

In step 102, when the sample to be tested or analyzed is a mixed sample (e.g. maternal blood sample), it is enriched for rare cells or rare DNA (e.g. fetal cells, fetal DNA or fetal nuclei) using one or more methods known in the art or disclosed herein. Such enrichment increases the ratio of fetal cells to non-fetal cells, the concentration of fetal DNA to non-fetal DNA, and/or the concentration of fetal cells in volume per total volume of the mixed sample.

In some embodiments, enrichment occurs by selective lysis as described above. For example, enucleated cells may be selectively lysed prior to subsequent enrichment steps or fetal nucleated cells may be selectively lysed prior to separation of the fetal nuclei from other cells and components in the sample.

In some embodiments, enrichment of fetal cells or fetal nuclei occurs using one or more size-based separation modules. Size-based separation modules include filtration modules, sieves, matrixes, etc., including those disclosed in International Publication Nos. WO 2004/113877, WO 2004/0144651, and US Application Publication No. 2004/011956.

In some embodiments, a size-based separation module includes one or more arrays of obstacles that form a network of gaps. The obstacles are configured to direct particles (e.g. cells or nuclei) as they flow through the array/network of gaps into different directions or outlets based on the particle's hydrodynamic size. For example, as a blood sample flows through an array of obstacles, nucleated cells or cells having a hydrodynamic size larger than a predetermined size, e.g., 8 microns, are directed to a first outlet located on the opposite side of the army of obstacles from the fluid flow inlet, while the enucleated cells or cells having a hydrodynamic size smaller than a predetermined size, e.g., 8 microns, are directed to a second outlet also located on the opposite side of the array of obstacles from the fluid flow inlet.

An army can be configured to separate cells smaller than a predetermined size from those larger than a predetermined size by adjusting the size of the gaps, obstacles, and offset in the period between each successive row of obstacles. For example, in some embodiments, obstacles and/or gaps between obstacles can be up to 10, 20, 50, 70, 100, 120, 150, 170, or 200 microns in length or about 2, 4, 6, 8 or 10 microns in length. In some embodiments, an army for size-based separation includes more than 100, 500, 1,000, 5,000, 10,000, 50,000 or 100,000 obstacles that are arranged into more than 10, 20, 50, 100, 200, 500, or 1000 rows. Preferably, obstacles in a first row of obstacles are offset from a previous (upstream) row of obstacles by up to 50% the period of the previous row of obstacles. In some embodiments, obstacles in a first row of obstacles are offset from a previous row of obstacles by up to 45, 40, 35, 30, 25, 20, 15 or 10% the period of the previous row of obstacles. Furthermore, the distance between a first row of obstacles and a second row of obstacles can be up to 10, 20, 50, 70, 100, 120, 150, 170 or 200 microns. A particular offset can be continuous (repeating for multiple rows) or non-continuous. In some embodiments, a separation module includes multiple discrete arrays of obstacles fluidly coupled such that they are in series with one another. Each army of obstacles has a continuous offset. But each subsequent (downstream) array of obstacles has an offset that is different from the previous (upstream) offset. Preferably, each subsequent array of obstacles has a smaller offset that the previous array of obstacles. This allows for a refinement in the separation process as cells migrate through the array of obstacles. Thus, a plurality of arrays can be fluidly coupled in series or in parallel, (e.g., more than 2, 4, 6, 8, 10, 20, 30, 40, 50). Fluidly coupling separation modules (e.g., arrays) in parallel allows for high-throughput analysis of the sample, such that at least 1, 2, 5, 10, 20, 50, 100, 200, or 500 mL per hour flows through the enrichment modules or at least 1, 5, 10, or 50 million cells per hour are sorted or flow through the device.

FIGS. 2A-2D illustrates an example of a size-based separation module. Obstacles (which may be of any shape)

are coupled to a flat substrate to form an array of gaps. A transparent cover or lid may be used to cover the array. The obstacles form a two-dimensional array with each successive row shifted horizontally with respect to the previous row of obstacles, where the array of obstacles directs component having a hydrodynamic size smaller than a predetermined size in a first direction and component having a hydrodynamic size larger that a predetermined size in a second direction. The flow of sample into the array of obstacles can be aligned at a small angle (flow angle) with respect to a line-of-sight of the array. Optionally, the army is coupled to an infusion pump to perfuse the sample through the obstacles. The flow conditions of the size-based separation module described herein are such that cells are sorted by the array with minimal damage. This allows for downstream analysis of intact cells and intact nuclei to be more efficient and reliable.

In one embodiment, a size-based separation module comprises an array of obstacles configured to direct fetal cells larger than a predetermined size to migrate along a line-of-sight within the array towards a first outlet or bypass channel leading to a first outlet, while directing cells and analytes smaller than a predetermined size through the array of obstacles in a different direction towards a second outlet.

A variety of enrichment protocols may be utilized although, in most embodiments, gentle handling of the cells is needed to reduce any mechanical damage to the cells or their DNA. This gentle handling also preserves the small number of fetal cells in the sample. Integrity of the nucleic acid being evaluated is an important feature to permit the distinction between the genomic material from the fetal cells and other cells in the sample. In particular, the enrichment and separation of the fetal cells using the arrays of obstacles produces gentle treatment which minimizes cellular damage and maximizes nucleic acid integrity permitting exceptional levels of separation and the ability to subsequently utilize various formats to very accurately analyze the genome of the cells which are present in the sample in extremely low numbers.

In some embodiments, enrichment of fetal cells occurs using one or more capture modules that selectively inhibit the mobility of one or more cells of interest. Preferable a capture module is fluidly coupled downstream to a size-based separation module. Capture modules can include a substrate having multiple obstacles that restrict the movement of cells or analytes greater than a predetermined size. Examples of capture modules that inhibit the migration of cells based on size are disclosed in U.S. Pat. Nos. 5,837,115 and 6,692,952.

In some embodiments, a capture module includes a two dimensional array of obstacles that selectively filters or captures cells or analytes having a hydrodynamic size greater than a particular gap size, e.g., predetermined size. Arrays of obstacles adapted for separation by capture can include obstacles having one or more shapes and can be arranged in a uniform or non-uniform order. In some embodiments, a two-dimensional array of obstacles is staggered such that each subsequent row of obstacles is offset from the previous row of obstacles to increase the number of interactions between the analytes being sorted (separated) and the obstacles.

Another example of a capture module is an affinity-based separation module. An affinity-based separation module captures analytes or cells of interest based on their affinity to a structure or particle as opposed to their size. One example of an affinity-based separation module is an array of obstacles that are adapted for complete sample flow through, but for the fact that the obstacles am covered with binding moieties that selectively bind one or more analytes (e.g., cell population) of interest (e.g., red blood cells, fetal cells, or nucleated cells) or analytes not-of-interest (e.g., white blood cells). Binding moieties can include e.g., proteins (e.g., ligands/receptors), nucleic acids having complementary counterparts in retained analytes, antibodies, etc. In some embodiments, an affinity-based separation module comprises a two-dimensional array of obstacles covered with one or more antibodies selected from the group consisting of: anti-CD71, anti-CD235a, anti-CD36, anti-carbohydrates, anti-selectin, anti-CD45, anti-GPA, and anti-antigen-i.

Figure 3A:
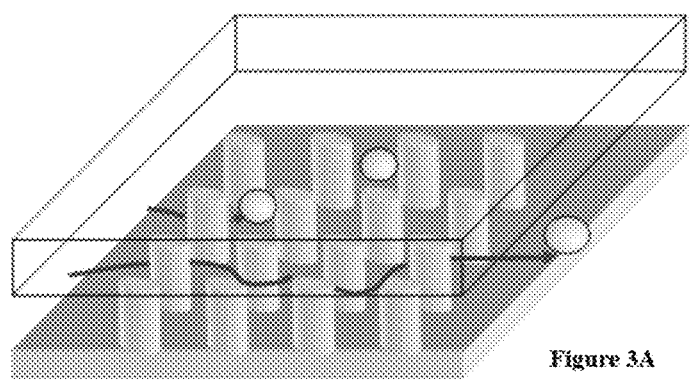
FIGS. 3A-3C illustrates one embodiment of an affinity separation module.
Figure 3B:
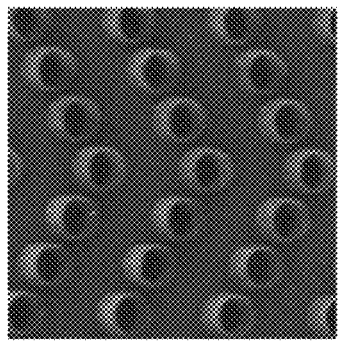
Figure 3C:
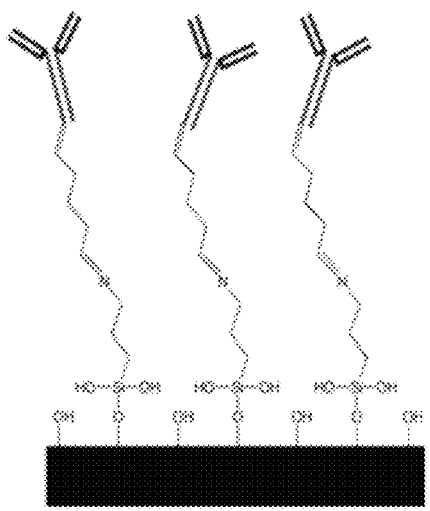

FIG. 3A illustrates a path of a first analyte through an army of posts wherein an analyte that does not specifically bind to a post continues to migrate through the array, while an analyte that does bind a post is captured by the array. FIG. 3B is a picture of antibody coated posts. FIG. 3C illustrates coupling of antibodies to a substrate (e.g., obstacles, side walls, etc.) as contemplated by the present invention. Examples of such affinity-based separation modules are described in International Publication No. WO 2004/029221.

In some embodiments, a capture module utilizes a magnetic field to separate and/or enrich one or more analytes (cells) that has a magnetic property or magnetic potential. For example, red blood cells which are slightly diamagnetic (repelled by magnetic field) in physiological conditions can be made paramagnetic (attracted by magnetic field) by deoxygenation of the hemoglobin into methemoglobin. This magnetic property can be achieved through physical or chemical treatment of the red blood cells. Thus, a sample containing one or more red blood cells and one or more non-red blood cells can be enriched for the red blood cells by first inducing a magnetic property and then separating the above red blood cells from other analytes using a magnetic field (uniform or non-uniform). For example, a maternal blood sample can flow first through a size-based separation module to remove enucleated cells and cellular components (e.g., analytes having a hydrodynamic size less than 6 μm) based on size. Subsequently, the enriched nucleated cells (e.g., analytes having a hydrodynamic size greater than 6 μm) white blood cells and nucleated red blood cells are treated with a reagent, such as $CO_2$, $N_2$ or $NaNO_2$, that changes the magnetic property of the red blood cells' hemoglobin. The treated sample then flows through a magnetic field (e.g., a column coupled to an external magnet), such that the paramagnetic analytes (e.g., red blood cells) will be captured by the magnetic field while the white blood cells and any other non-red blood cells will flow through the device to result in a sample enriched in nucleated red blood cells (including fnRBC's). Additional examples of magnetic separation modules are described in U.S. application Ser. No. 11/323,971, filed Dec. 29, 2005 entitled "Devices and Methods for Magnetic Enrichment of Cells and Other Particles" and U.S. application Ser. No. 11/227,904, filed Sep. 15, 2005, entitled "Devices and Methods for Enrichment and Alteration of Cells and Other Particles".

Subsequent enrichment steps can be used to separate the rare cells (e.g. fnRBC's) from the non-rare maternal nucleated red blood cells (non-RBC's). In some embodiments, a sample enriched by size-based separation followed by affinity/magnetic separation is further enriched for rare cells using fluorescence activated cell sorting (FACS) or selective lysis of a subset of the cells (e.g. fetal cells). In some embodiments, fetal cells are selectively bound to an anti-antigen 1 binding moiety (e.g. an antibody) to separate them from the mnRBC's. In some embodiments, fetal cells or fetal DNA is distinguished from non-fetal cells or non-fetal DNA by forcing the rare cells (fetal cells) to become apoptotic, thus condensing their nuclei and optionally ejecting their nuclei. Rare cells such as fetal cells can be forced into apoptosis using various means including subjecting the cells to hyperbaric pressure (e.g. 4% $CO_2$). The condensed nuclei can be detected and/or isolated for further analysis using any technique known in the art including DNA gel electrophoresis, in situ labeling of DNA nicks (terminal deoxynucleotidyl transferase (TdT))-mediated dUTP in situ nick labeling (also known as TUNEL) (Gavrieli, Y., et al. J. Cell Biol 119:493-501 (1992)) and ligation of DNA strand breaks having one or two-base 3' overhangs (Taq polymerase-based in situ ligation). (Didenko V., et al. J. Cell Biol. 135:1369-76 (1996)).

In some embodiments, when the analyte desired to be separated (e.g., red blood cells or white blood cells) is not ferromagnetic or does not have a magnetic property, a magnetic particle (e.g., a bead) or compound (e.g., $Fe^{3+}$) can be coupled to the analyte to give it a magnetic property. In some embodiments, a bead coupled to an antibody that selectively binds to an analyte of interest can be decorated with an antibody elected from the group of anti CD71 or CD75. In some embodiments a magnetic compound, such as $Fe^{3+}$, can be coupled to an antibody such as those described above. The magnetic particles or magnetic antibodies herein may be coupled to any one or more of the devices described herein prior to contact with a sample or may be mixed with the sample prior to delivery of the sample to the device(s).

The magnetic field used to separate analytes/cells in any of the embodiments herein can uniform or non-uniform as well as external or internal to the device(s) herein. An external magnetic field is one whose source is outside a device herein (e.g., container, channel, obstacles). An internal magnetic field is one whose source is within a device contemplated herein. An example of an internal magnetic field is one where magnetic particles may be attached to obstacles present in the device (or manipulated to create obstacles) to increase surface area for analytes to interact with to increase the likelihood of binding. Analytes captured by a magnetic field can be released by demagnetizing the magnetic regions retaining the magnetic particles. For selective release of analytes from regions, the demagnetization can be limited to selected obstacles or regions. For example, the magnetic field can be designed to be electromagnetic, enabling turn-on and turn-off of the magnetic fields for each individual region or obstacle at will.

Figure 4:
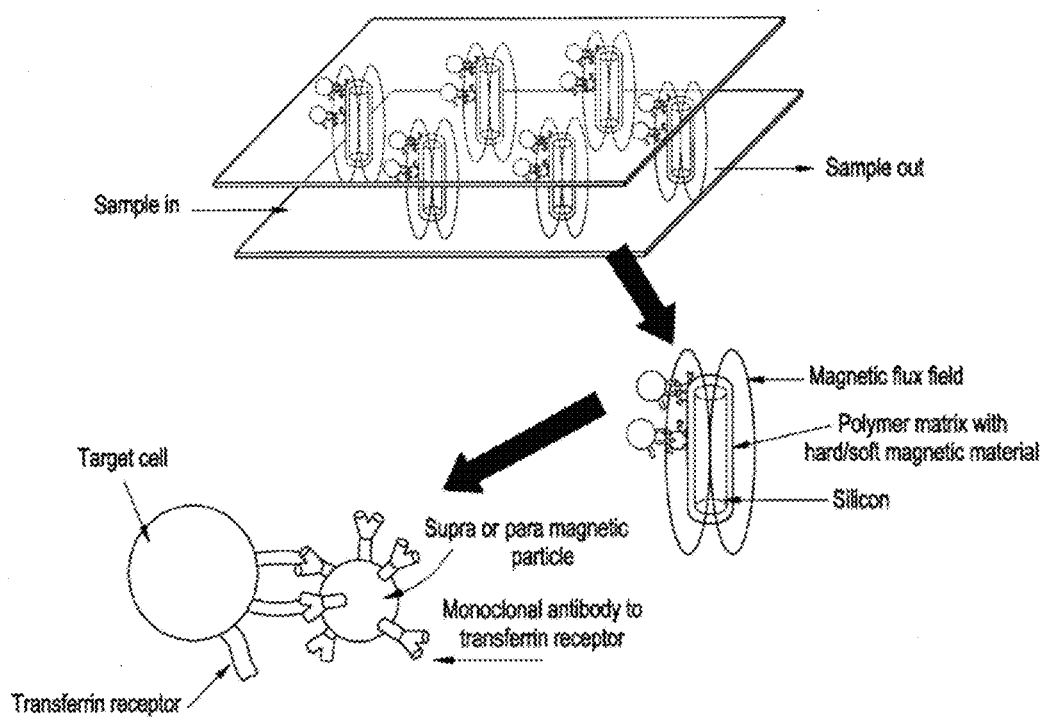
FIG. 4 illustrates one embodiment of a magnetic separation module.

FIG. 4 illustrates an embodiment of a device configured for capture and isolation of cells expressing the transferrin receptor from a complex mixture. Monoclonal antibodies to CD71 receptor are readily available off-the-shelf and can be covalently coupled to magnetic materials, such as, but not limited to any conventional ferroparticles including ferrous doped polystyrene and ferroparticles or ferro-colloids (e.g., from Miltenyi or Dynal). The anti CD71 bound to magnetic particles is flowed into the device. The antibody coated particles are drawn to the obstacles (e.g., posts), floor, and walls and are retained by the strength of the magnetic field interaction between the particles and the magnetic field. The particles between the obstacles, and those loosely retained with the sphere of influence of the local magnetic fields away from the obstacles, are removed by a rinse.

One or more of the enrichment modules herein (e.g., size-based separation module(s) and capture module(s)) may be fluidly coupled in series or in parallel with one another. For example a first outlet from a separation module can be fluidly coupled to a capture module. In some embodiments, the separation module and capture module are integrated such that a plurality of obstacles acts both to deflect certain analytes according to size and direct them in a path different than the direction of analyte(s) of interest, and also as a capture module to capture, retain, or bind certain analytes based on size, affinity, magnetism or other physical property.

In any of the embodiments herein, the enrichment steps performed have a specificity and/or sensitivity ≥50, 60, 70, 80, 90, 95, 96, 97, 98, 99, 99.1, 99.2, 99.3, 99.4, 99.5, 99.6, 99.7, 99.8, 99.9 or 99.95% The retention rate of the enrichment module(s) herein is such that ≥50, 60, 70, 80, 90, 91, 92, 93, 94, 95, 96, 97, 98, 99, or 99.9% of the analytes or cells of interest (e.g., nucleated cells or nucleated red blood cells or nucleated from red blood cells) are retained. Simultaneously, the enrichment modules are configured to remove ≥50, 60, 70, 80, 85, 90, 91, 92, 93, 94, 95, 96, 97, 98, 99, or 99.9% of all unwanted analytes (e.g., red blood-platelet enriched cells) from a sample.

Any or all of the enrichment steps can occur with minimal dilution of the sample. For example, in some embodiments the analytes of interest are retained in an enriched solution that is less than 50, 40, 30, 20, 10, 9.0, 8.0, 7.0, 6.0, 5.0, 4.5, 4.0, 3.5, 3.0, 2.5, 2.0, 1.5, 1.0, or 0.5 fold diluted from the original sample. In some embodiments, any or all of the enrichment steps increase the concentration of the analyte of interest (e.g. fetal cell), for example, by transferring them from the fluid sample to an enriched fluid sample (sometimes in a new fluid medium, such as a buffer). The new concentration of the analyte of interest may be at least 2, 4, 6, 8, 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 50,000,000, 100,000,000, 200,000,000, 500,000,000, 1,000,000,000, 2,000,000,000, or 5,000,000,000 fold more concentrated than in the original sample. For example, a 10 times concentration increase of a first cell type out of a blood sample means that the ratio of first cell type/all cells in a sample is 10 times greater after the sample was applied to the apparatus herein. Such concentration can take a fluid sample (e.g., a blood sample) of greater than 10, 15, 20, 50, or 100 mL total volume comprising rare components of interest, and it can concentrate such rare component of interest into a concentrated solution of less than 0.5, 1, 2, 3, 5, or 10 ml. total volume.

The final concentration of rare cells in relation to non-rare cells after enrichment can be about 1/10,000-1/10, or 1/1,000-1/100. In some embodiments, the concentration of fetal cells to maternal cells may be up to 1/1,000, 1/100, or 1/10 or as low as 1/100, 1/1000 or 1/10,000.

Thus, detection and analysis of the fetal cells can occur even if the non-fetal (e.g. maternal) cells are >50%, 60%, 70%, 80%, 90%, 95%, or 99% of all cells in a sample. In some embodiments, fetal cells are at a concentration of less than 1:2, 1:4, 1:10, 1:50, 1:100, 1:1000, 1:10,000, 1:100,000, 1,000,000, 1:10,000,000 or 1:100,000,000 of all cells in a mixed sample to be analyzed or at a concentration of less than $1\times10^{-3}$, $1\times10^{-4}$, $1\times10^{-5}$, $1\times10^{-6}$, or $1\times10^{-6}$ cells/µL of the mixed sample. Over all, the number of fetal cells in a mixed sample, (e.g. enriched sample) has up to 1, 2, 3, 4, 5, 6, 7, 8, 9, 10, 15, 20, 30, 40, 50, 100 total fetal cells.

Figure 17:
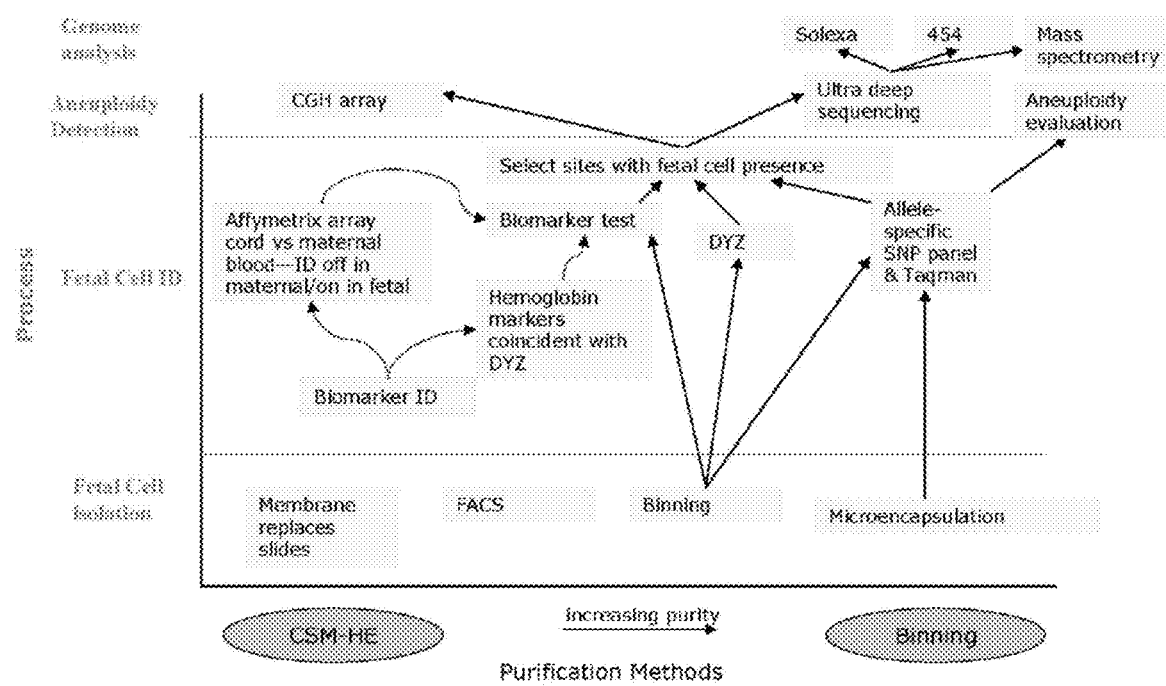
FIG. 17 illustrates methods of fetal diagnostic assays. Fetal cells are isolated by CSM-HE enrichment of target cells from blood. The designation of the fetal cells may be confirmed using techniques comprising FISH staining (using slides or membranes and optionally an automated detector), FACS, and/or binning. Binning may comprise distribution of enriched cells across wells in a plate (such as a 96 or 384 well plate), microencapsulation of cells in droplets that are separated in an emulsion, or by introduction of cells into microarrays of nanofluidic bins. Fetal cells are then identified using methods that may comprise the use of biomarkers (such as fetal (gamma) hemoglobin), allele-specific SNP panels that could detect fetal genome DNA, detection of differentially expressed maternal and fetal transcripts (such as Affymetrix chips), or primers and probes directed to fetal specific loci (such as the multi-repeat DYZ locus on the Y-chromosome). Binning sites that contain fetal cells am then be analyzed for aneuploidy and/or other genetic defects using a technique such as CGH army detection, ultra deep sequencing (such as Solexa, 454, or mass spectrometry), STR analysis, or SNP detection.
Figure 18:
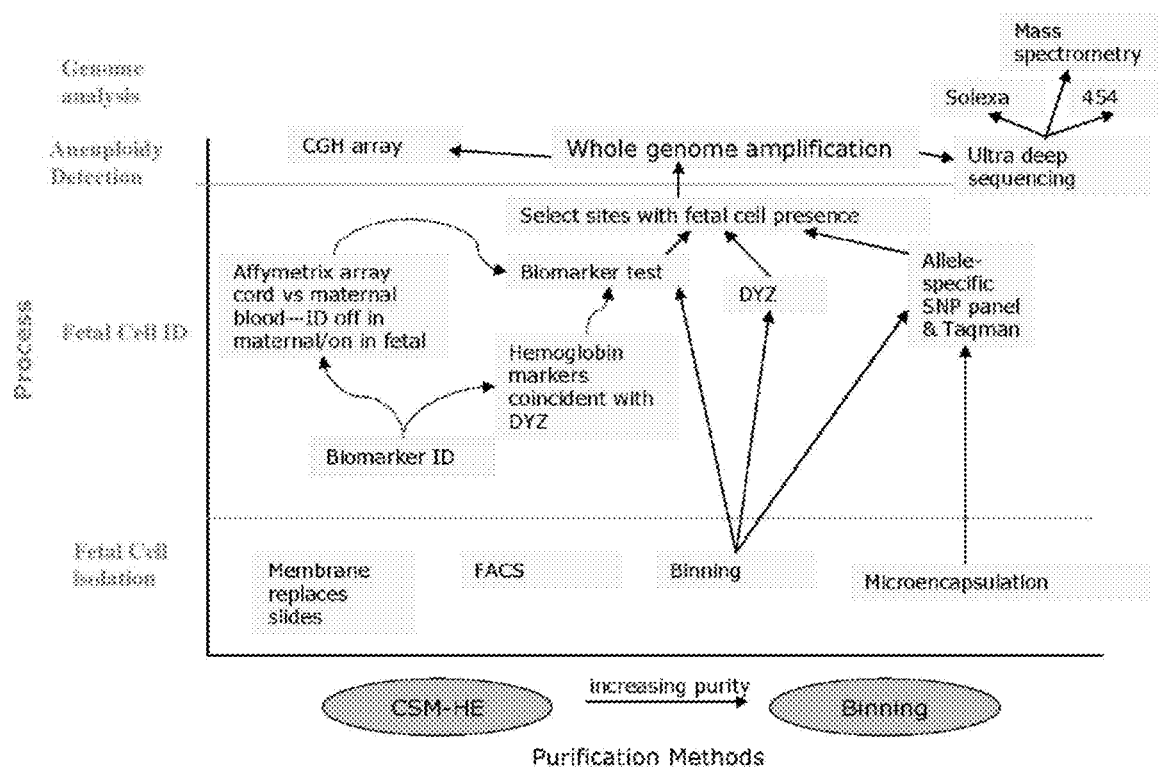
FIG. 18 illustrates methods of fetal diagnostic assays, further comprising the step of whole genome amplification prior to analysis of aneuploidy and/or other genetic defects.

Enriched target cells (e.g., fnRBC) can be "binned" prior to analysis of the enriched cells (FIGS. 17 and 18). Binning is any process which results in the reduction of complexity and/or total cell number of the enriched cell output. Binning may be performed by any method known in the art or described herein. One method of binning the enriched cells is by serial dilution. Such dilution may be carried out using any appropriate platform (e.g., PCR wells, microtiter plates). Other methods include nanofluidic systems which separate samples into droplets (e.g., BioTrove, Raindance, Fluidigm). Such nanofluidic systems may result in the presence of a single cell present in a nanodroplet.

Binning may be preceded by positive selection for target cells including, but not limited to affinity binding (e.g. using anti-CD71 antibodies). Alternately, negative selection of non-target cells may precede binning. For example, output from the size-based separation module may be passed through a magnetic hemoglobin enrichment module (MHEM) which selectively removes WBCs from the enriched sample.

For example, the possible cellular content of output from enriched maternal blood which has been passed through a size-based separation module (with or without further enrichment by passing the enriched sample through a MHEM) may consist of: 1) approximately 20 fnRBC; 2) 1,500 mnRBC; 3) 4,000-40,000 WBC; 4) $15 \times 10^6$ RBC. If this sample is separated into 100 bins (PCR wells or other acceptable binning platform), each bin would be expected to contain: 1) 80 negative bins and 20 bins positive for one fnRBC; 2) 150 mnRBC; 3) 400-4,000 WBC; 4) $15 \times 10^4$ RBC. If separated into 10,000 bins, each bin would be expected to contain: 1) 9,980 negative bins and 20 bins positive for one fnRBC; 2) 8,500 negative bins and 1,500 bins positive for one mnRBC; 3)<1-4 WBC; 4) $15 \times 10^2$ RBC. One of skill in the art will recognize that the number of bins may be increased depending on experimental design and/or the platform used for binning. The reduced complexity of the binned cell populations may facilitate further genetic and cellular analysis of the target cells.

Analysis may be performed on individual bins to confirm the presence of target cells (e.g. fnRBC) in the individual bin. Such analysis may consist of any method known in the art, including, but not limited to, FISH, PCR, STR detection, SNP analysis, biomarker detection, and sequence analysis (FIGS. 17 and 18).

Fetal Biomarkers

In some embodiments fetal biomarkers may be used to detect and/or isolate fetal cells, after enrichment or after detection of fetal abnormality or lack thereof. For example, this may be performed by distinguishing between fetal and maternal nRBCs based on relative expression of a gene (e.g., DYS1, DYZ, CD-71, ε- and ζ-globin) that is differentially expressed during fetal development. In preferred embodiments, biomarker genes are differentially expressed in the first and/or second trimester. "Differentially expressed," as applied to nucleotide sequences or polypeptide sequences in a cell or cell nuclei, refers to differences in over/underexpression of that sequence when compared to the level of expression of the same sequence in another sample, a control or a reference sample. In some embodiments, expression differences can be temporal and/or cell-specific. For example, for cell-specific expression of biomarkers, differential expression of one or more biomarkers in the cell(s) of interest can be higher or lower relative to background cell populations. Detection of such difference in expression of the biomarker may indicate the presence of a rare cell (e.g., fnRBC) versus other cells in a mixed sample (e.g., background cell populations). In other embodiments, a ratio of two or more such biomarkers that are differentially expressed can be measured and used to detect rare cells.

In one embodiment, fetal biomarkers comprise differentially expressed hemoglobins. Erythroblasts (nRBCs) are very abundant in the early fetal circulation, virtually absent in normal adult blood and by having a short finite lifespan, there is no risk of obtaining fnRBC which may persist from a previous pregnancy. Furthermore, unlike trophoblast cells, fetal erythroblasts are not prone to mosaic characteristics.

Yolk sac erythroblasts synthesize ε-, ζ-, γ- and α-globins, these combine to form the embryonic hemoglobins. Between six and eight weeks, the primary site of erythropoiesis shifts from the yolk sac to the liver, the three embryonic hemoglobins are replaced by fetal hemoglobin (HbF) as the predominant oxygen transport system, and ε- and ζ-globin production gives way to γ-, α- and β-globin production within definitive erythrocytes (Peschle et al., 1985). HbF remains the principal hemoglobin until birth, when the second globin switch occurs and β-globin production accelerates.

Hemoglobin (Hb) is a heterodimer composed of two identical α globin chains and two copies of a second globin. Due to differential gene expression during fetal development, the composition of the second chain changes from ε globin during early embryonic development (1 to 4 weeks of gestation) to γ globin during fetal development (6 to 8 weeks of gestation) to β globin in neonates and adults as illustrated in (Table 1).

TABLE 1

Relative expression of ε, γ and β in maternal and fetal RBCs.

|  |  | ε | γ | B |
|---|---|---|---|---|
| 1st trimester | Fetal | ++ | ++ | − |
|  | Maternal | − | +/− | ++ |
| 2nd trimester | Fetal | − | ++ | +/− |
|  | Maternal | − | +/− | ++ |

In the late-first trimester, the earliest time that fetal cells may be sampled by CVS, fnRBCs contain, in addition to α globin, primarily ε and γ globin. In the early to mid second trimester, when amniocentesis is typically performed, fnRBCs contain primarily γ globin with some adult β globin. Maternal cells contain almost exclusively α and β globin, with traces of γ detectable in some samples. Therefore, by measuring the relative expression of the ε, γ and β genes in RBCs purified from maternal blood samples, the presence of fetal cells in the sample can be determined. Furthermore, positive controls can be utilized to assess failure of the FISH analysis itself.

In various embodiments, fetal cells are distinguished from maternal cells based on the differential expression of hemoglobins β, γ or ε. Expression levels or RNA levels can be determined in the cytoplasm or in the nucleus of cells. Thus in some embodiments, the methods herein involve determining levels of messenger RNA (mRNA), ribosomal RNA (rRNA), or nuclear RNA (nRNA).

In some embodiments, identification of fnRBCs can be achieved by measuring the levels of at least two hemoglobins in the cytoplasm or nucleus of a cell. In various embodiments, identification and assay is from 1, 2, 3, 4, 5, 6, 7, 8, 9, 10, 15 or 20 fetal nuclei. Furthermore, total nuclei arrayed on one or more slides can number from about 100, 200, 300, 400, 500, 700, 800, 5000, 10,000, 100,000, 1,000,000, 2,000,000 to about 3,000,000. In some embodiments, a ratio for γ/β or ε/β is used to determine the presence of fetal cells, where a number less than one indicates that a fnRBC(s) is not present. In some embodiments, the relative expression of γ/β or ε/β provides a fnRBC index ("FNI"), as measured by γ ore relative to β. In some embodiments, a FNI for γ/β greater than 5, 10, 15, 20, 25, 30, 35, 40, 45, 90, 180, 360, 720, 975, 1020, 1024, 1250 to about 1250, indicate that a fnRBC(s) is present. In yet other embodiments, a FNI for γ/β of less than about 1 indicates that a fnRBC(s) is not present. Preferably, the above FNI is determined from a sample obtained during a first trimester. However, similar ratios can be used during second trimester and third trimester.

In some embodiments, the expression levels am determined by measuring nuclear RNA transcripts including, nascent or unprocessed transcripts. In another embodiment, expression levels are determined by measuring mRNA, including ribosomal RNA. There are many methods known in the art for imaging (e.g., measuring) nucleic acids or RNA including, but not limited to, using expression arrays from Affymetrix, Inc. or Illumina, Inc.

RT-PCR primers can be designed by targeting the globin variable regions, selecting the amplicon size, and adjusting the primers annealing temperature to achieve equal PCR amplification efficiency. Thus TaqMan probes can be designed for each of the amplicons with well-separated fluorescent dyes, Alexa Fluor®-355 for ε, Alexa Fluor®-488 for γ, and Alexa Fluor-555 for β. The specificity of these primers can be first verified using ε, γ, and β cDNA as templates. The primer sets that give the best specificity can be selected for further assay development. As an alternative, the primers can be selected from two exons spanning an intron sequence to amplify only the mRNA to eliminate the genomic DNA contamination.

The primers selected can be tested first in a duplex format to verify their specificity, limit of detection, and amplification efficiency using target cDNA templates. The best combinations of primers can be further tested in a triplex format for its amplification efficiency, detection dynamic range, and limit of detection.

Various commercially available reagents are available for RT-PCR, such as One-step RT-PCR reagents, including Qiagen One-Step RT-PCR Kit and Applied Biosystems TaqMan One-Step RT-PCR Master Mix Reagents kit. Such reagents can be used to establish the expression ratio of ε, γ and β using purified RNA from enriched samples. Forward primers can be labeled for each of the targets, using Alexa fluor-355 for ε, Alexa fluor-488 for γ, and Alexa fluor-555 for β. Enriched cells can be deposited by cytospinning onto glass slides. Additionally, cytospinning the enriched cells can be performed after in situ RT-PCR. Thereafter, the presence of the fluorescent-labeled amplicons can be visualized by fluorescence microscopy. The reverse transcription time and PCR cycles can be optimized to maximize the amplicon signal:background ratio to have maximal separation of fetal over maternal signature. Preferably, signal:background ratio is greater than 5, 10, 50 or 100 and the overall cell loss during the process is less than 50, 10 or 5%.

Fetal Cell Analysis

In step 125, DNA is extracted and purified from cells/nuclei of the enriched product (mixed sample enriched) and reference sample. Methods for extracting DNA are known to those skilled in the art.

In step 131, the DNA is optionally pre-amplified to increase the overall quantity of DNA for subsequent analysis. Pre-amplification of DNA can be conducted using any amplification method known in the art, including for example, amplification via multiple displacement amplification (MDA) (Gonzalez J M, et al. Cold Spring Hath Symp Quant Biol; 68:69-78 (2003), Murthy et al. Hum Mutat 26(2):145-52 (2005) and Paulland et al., Biotechniques; 38(4):553-4, 556, 558-9 (2005)), and linear amplification methods such as in vitro transcription (Liu, et al., BMC Genomics; 4(1)19 (2003)).

Other methods for pre-amplification include PCR methods including quantitative PCR, quantitative fluorescent PCR (QF-PCR), multiplex fluorescent PCR (MF-PCR), real time PCR (RT-PCR), single cell PCR, PCR-RFLP/RT-PCR-RFLP, hot start PCR and Nested PCR. For example, the PCR products can be directly sequenced bi-directionally by dye-terminator sequencing. PCR can be performed in a 384-well plate in a volume of 15 ul containing 5 ng genomic DNA, 2 mM MgCl2, 0.75 ul DMSO, 1 M Betaine, 0.2 mM dNTPs, 20 pmol primers, 0.2 ul AmpliTaq Gold® (Applied Biosystems), IX buffer (supplied with AmpliTaq Gold). Thermal cycling conditions are as follows: 95° C. for 10 minutes; 95° C. for 30 seconds, 60° C. for 30 seconds, 72° C. for 1 minute for 30 cycles; and 72° C. for 10 minutes. PCR products can be purified with Ampure® Magnetic Beads (Agencourt) and can be optionally separated by capillary electrophoresis on an AB13730 DNA Analyzer (Applied Biosystems).

Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR) and nucleic acid based sequence amplification (NABSA). Other amplification methods that may be used in step 131 include those described in, U.S. Pat. Nos. 5,242,794, 5,494,810, 4,988,617 and 6,582,938, each of which is incorporated herein by reference.

The pre-amplification step increases the amount of enriched fetal DNA thus allowing analysis to be performed even if up to 1 ng, 500 ng, 200 ng 100 ng, 50 ng, 40 ng, 30 ng, 20 ng, 10 ng, 5 ng, 1 ng, 500 pg, 200 pg, 100 pg, 50 pg, 40 pg, 30 pg, 20 pg, 10 pg, 5 pg, or 1 pg of fetal or total DNA was obtained from the mixed sample, or between 1-5 μg, 5-10 μg, 10-50 μg of fetal or total DNA was obtained from the mixed sample.

In step 141, SNP(s) are detected from DNA of both mixed and reference samples using any method known in the art. Detection can involve detecting an abundance of a nucleotide base at a SNP position. Detection can be accomplished using a DNA microarray, bead microarray, or high throughput sequencing. In some instances SNPs are detected using highly parallel SNP detection methods such as those described in Fan J B, et al. Cold Spring Hat Symp Quant Biol; 68:69-78 (2003); Moorhead M, et al. Eur. J. Hum Genet 14:207-215 (2005); Wang Y, et. al. Nucleic Acids Res; 33(21):e183 (2005). Highly parallel SNP detection provides information about genotype and gene copy numbers at a large number of loci scattered across the genome in one procedure. In some cases, highly parallel SNP detection involves performing SNP specific ligation-extension reactions, followed by amplification of the products. The readout of the SNP types can be done using DNA microarrays (Gunderson et al. Nat. Genety 37(5):549-54 (2005), bead arrays (Shen, et al., Mutat. Res; 573 (1-2):70-82 (2005), or by sequencing, such as high throughput sequencing (e.g. Margulies et al. Nature, 437 (7057):376-80 (2005)) of individual amplicons.

In some embodiments, cDNAs, which are reverse transcribed from mRNAs obtained from fetal or maternal cells, are analyzed for the presence of SNPS using the methods disclosed within. The type and abundance of the cDNAs can be used to determine whether a cell is a fetal cell (such as by the presence of Y chromosome specific transcripts) or whether the fetal cell has a genetic abnormality (such as anueploidy, abundance of alternative transcripts or problems with DNA methylation or imprinting).

In one embodiment, fetal or maternal cells or nuclei are enriched using one or more methods disclosed herein. Preferably, fetal cells are enriched by flowing the sample through an array of obstacles that selectively directs particles or cells of different hydrodynamic sizes into different outlets such that fetal cells and cells larger than fetal cells are directed into a first outlet and one or more cells or particles smaller than the rare cells are directed into a second outlet.

Total RNA or poly-A mRNA is then obtained from enriched cell(s) (fetal or maternal cells) using purification techniques known in the art. Generally, about 1 µg-2 µg of total RNA is sufficient. Next, a first-strand complementary DNA (cDNA) is synthesized using reverse transcriptase and a single T7-oligo(dT) primer. Next, a second-strand cDNA is synthesized using DNA ligase, DNA polymerase, and RNase enzyme. Next, the double stranded cDNA (ds-cDNA) is purified.

In another embodiment, total RNA is extracted from enriched cells (fetal cells or maternal cells). Next a, two one-quarter scale Message Amp II reactions (Ambion, Austin, Tex.) are performed for each RNA extraction using 200 ng of total RNA. MessageAmp is a procedure based on antisense RNA (aRNA) amplification, and involves a series of enzymatic reactions resulting in linear amplification of exceedingly small amounts of RNA for use in army analysis. Unlike exponential RNA amplification methods, such as NASBA and RT-PCR, aRNA amplification maintains representation of the starting mRNA population. The procedure begins with total or poly(A) RNA that is reverse transcribed using a primer containing both oligo(dT) and a T7 RNA polymerase promoter sequence. After first-strand synthesis, the reaction is treated with RNase H to cleave the mRNA into small fragments. These small RNA fragments serve as primers during a second-strand synthesis reaction that produces a double-stranded cDNA template.

Any DNA microarray that is capable of detecting one or more SNPs can be used with the methods herein. DNA microarrays comprise a plurality of genetic probes immobilized at discrete sites (i.e., defined locations or assigned positions) on a substrate surface. A DNA microarray preferably monitors at least 5, 10, 20, 50, 100, 200, 500, 1,000, 2,000, 5,000, 10,000, 20,000, 50,000, 100,000, 200,000 or 500,000 different SNPs. Such SNPs can be located in one or more target chromosomes or over the entire genome. Methods for manufacturing DNA microarrays for detecting SNPs are known in the art. Microarrays that can be used in the systems herein include those commercially available from Affymetrix (Santa Clara, Calif.), Illumina (San Diego, Calif.), Spectral Genomics, Inc. (Houston, Tex.), and Vysis Corporation (Downers Grove, Ill.). Methods for detecting SNPs using microarrays are further described in U.S. Pat. Nos. 6,300,063, 5,837,832, 6,969,589, 6,040,138, and 6,858,412.

In one embodiment, SNPs are detected using molecular inversion probes (MIPs). MIPs are nearly circularized probes having a first end of the probe complementary to a region immediately upstream of the SNP to be detected, and a second end of the probe complementary to a region immediately downstream of the SNP. To use MIPs both ends are allowed to hybridize to genomic regions surrounding the SNP and an enzymatic reaction fills the gap at the SNP position in an allele specific manner. The fully circular probe now can be separated by a simple exonuclease reaction which leaves a primer sequence coupled to a label unique to the allele. The primer is subsequently used to amplify the label which is then hybridized to an array for detection.

Figure 5:
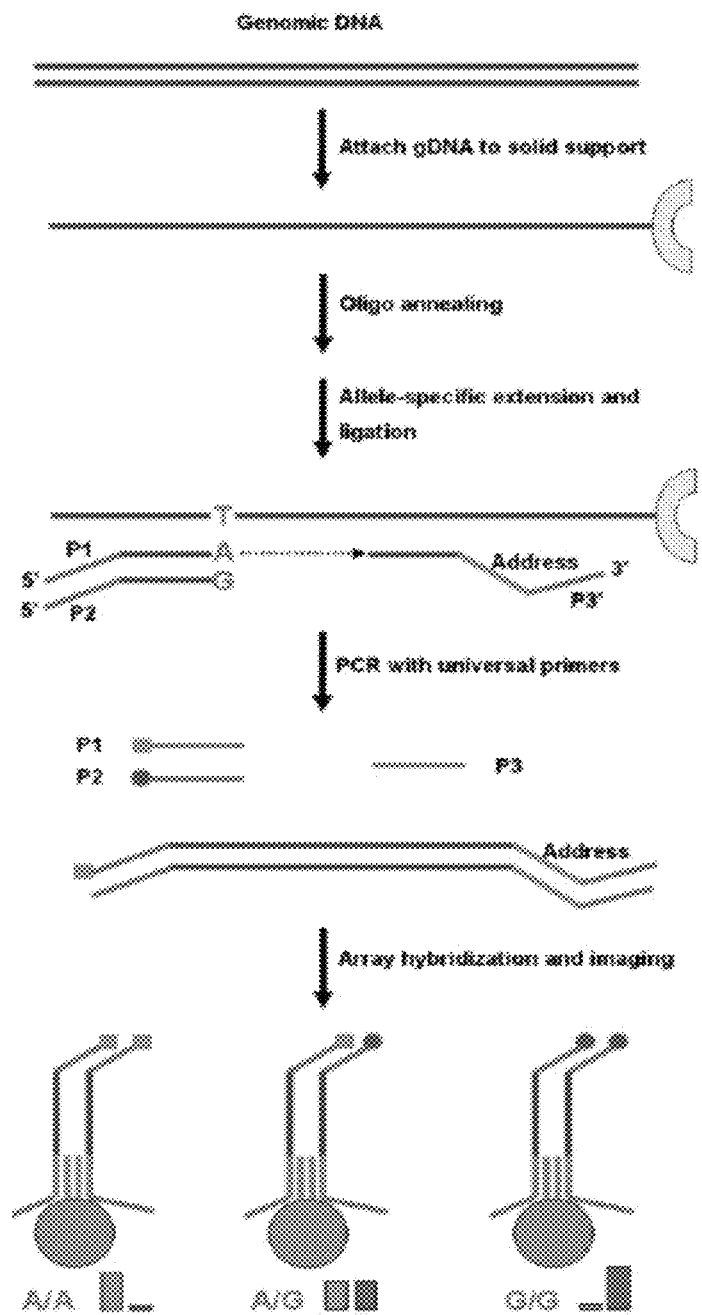
FIG. 5 illustrates an overview for a typical parallel SNP genotyping assay.

FIG. 5 illustrates one embodiment of an allele specific extension and ligation reaction. Genomic DNA fragments are first annealed to a solid support. Subsequently, probes designed to be unique for each allele (P1 and P2) are annealed to the target DNA. After a washing step, allele-specific primer extension is conducted to extend the probes if such probes have 3' ends that are complementary to their cognate SNP in the genomic DNA template. The extension is followed by ligation of the extended templates to their corresponding locus-specific probes (P3) to create PCR templates. Requiring the joining of two fragments (P1 and P3 or P2 and P3) to create a PCR template provides an additional level of genomic specificity, because any residual incorrectly hybridized allele-specific or locus-specific probes are unlikely to be adjacent and thus should not be able to ligate. Next, fluorescently labeled primers, each with a different dye, are added for PCR amplification, thus providing a means for detection and quantification of each SNP by providing data points. In addition, each SNP is assigned a different address sequence (P3) which is contained within the locus-specific probe. Each address sequence is complementary to a unique capture sequence that can be contained by one of several bead types present in an array. Furthermore, the use of universal PCR primers to associate a fluorescent dye with each SNP allele provides a cost-saving element, because only three primers, two labeled and one unlabeled, are needed regardless of the number of SNPs to be assayed.

If the addresses are captured by beads, multiple SNPs can be amplified in the same or in different reactions using bead amplification. When more than one DNA polymorphism is used in the same amplification reaction, primers are chosen to be multiplexable (fairly uniform melting temperature, absence of cross-priming on the human genome, and absence of primer-primer interaction based on sequence analysis) with other pairs of primers. Furthermore, primers and loci may be chosen so that the amplicon lengths from a given locus do not overlap with those from another locus. Multiple dyes and multi-color fluorescence readout may be used to increase the multiplexing capacity.

In some embodiments, highly parallel SNP detection is performed by arrayed primer extension (APEX). In order to perform APEX, a gene locus is chosen where one wishes to analyze SNPs or mutations, for example, loci for abnormal ploidy disorders (e.g. chromosome X, 13, 18, and 21). Oligonucleotides (e.g., about 20-, 25-, 30-, 40-, 50-mers) are designed to be complementary to the gene up to, but not including the base where the mutation or SNP exists. In one example, the oligonucleotides are modified with an amine group at the 5' end to facilitate covalent binding to activated glass slides, in this case epoxy silanized surfaces. The locus in question is PCR amplified and the DNA enzymatically sheared to facilitate hybridization to the oligos. The PCR reactions contain dTTP and dUTP at about a 5 to 1 ratio, and the incorporation of the dUTP allows the amplified DNA to be enzymatically cut with uracil N-glycosylase (UNG). The optimal size of the sheared DNA is about 100 base pairs. The sheared DNA is then hybridized to the bound oligos and a primer extension reaction carried out using a thermostable DNA polymerase such as Thermo Sequenase (Amersham Pharmacia Biotech) or AmpliTaq FS (Roche Molecular Systems). The primer extension reaction contains four dideoxynucleotides (ddNTPs) corresponding to A, G, C & T, with each ddNTP containing a distinct fluor molecule. In the above example, ddNTPs can be conjugated to either fluorescein, Cy3™, Texas Red or Cy5™. Depending on which base is next in the sequence (wild type, mutant or SNP), the primer extension reaction will incorporate one nucleotide with one and only one of the four dyes. Thus, by applying a simple four laser scan one can tell which base is next in the sequence as each of the above dyes are easily spectrally separable. A large number of different oligos, (e.g., 5-, 10-, 15-, 20-, 30-, 40-, 50-, 60-, 70-, 80-, 90-, 100-thousand probes) may be attached to a slide for this type of analysis with the requirement that very little cross hybridization occurs among all the sequences. It may be helpful to increase the length of the oligos (e.g., 50-, 60-, 70-, 80-mers) so that the initial hybridization can be done at higher stringency resulting in less background from non-homologous hybridization. In the APEX method, the signal to noise ratio is about 40 to 1, a level which is more than sufficient for unambiguously identifying SNPs and mutations. To design such large arrays for SNP analysis, a computational screen can be conducted to favor a subset of sequences with similar GC content and thermodynamic properties, and eliminate sequences with possible secondary structure or sequence similarity to other tags. Shoemaker et al. Nature Genetics 14:450-456 (1996); Giaever et al. Nature Genetics 21:278-283 (1999); Winzeler et al. Science 285:901-906 (1999). For example, in high density tag array 64,000 probes, each probe occupying an area of 30×30 μm, are used for parallel genotyping of human SNPs.

In some cases, it may be desirable to introduce a novel restriction site in the region of the mutation to create cleavage-based detection. Gasparini, et al., *Mol. Cell Probes* 6:1 (1992). Amplification is subsequently performed using Taq ligase and the like. Barony, Proc. Natl. Acad. Sci. USA 88:189 (1991). In such cases, ligation will occur only if there is a perfect match at the 3'-terminus of the 5' sequence, making it possible to detect the presence of a known mutation at a specific site by looking for the presence or absence of amplification.

Alternatively, detection of single strand conformation polymorphism (SSCP) may be used to detect differences in electrophoretic mobility between mutant and wild type nucleic acids (e.g., SNP). Orita, et al., Proc. Natl. Acad. Sci. USA: 86: 2766 (1989); Cotton, Mutat. Res. 285: 125-144 (1993); and Hayashi, Genet. Anal. Tech. Appl. 9: 73-79 (1992). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. The subject method utilizes heteroduplex analysis to separate double-stranded heteroduplex molecules on the basis of changes in electrophoretic mobility. Keen, et al., Trends Genet. 7: 5 (1991).

Other methods for detecting SNPs include methods in which protection from cleavage agents is used to detect mismatched bases in DNA/DNA or RNA/DNA heteroduplexes. Myers, et al., Science 230: 1242 (1985). In general, the art technique of "mismatch cleavage" starts by providing, heteroduplexes of formed by hybridizing (labeled) RNA or DNA containing the control sequence with potentially mutant RNA or DNA obtained from a tissue sample. The double-stranded duplexes are treated with an agent that cleaves single stranded regions of the duplex such as those that exist due to "base pair mismatches" between the control and sample strands. For instance, RNA/DNA duplexes can be treated with RNase and DNA/DNA hybrids treated with SI nuclease to enzymatically digesting the mismatched regions.

Furthermore, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. Cotton, et al., Proc. Natl. Acad. Sci. USA 85:4397 (1988); and Saleeba, et al., Methods Enzymol. 2 17: 286-295 (1992). The control DNA or RNA can be labeled for detection.

SNPs can also be detected and quantified using by sequencing methods including the classic Sanger sequencing method as well as high throughput sequencing, which may be capable of generating at least 1,000, 5,000, 10,000, 20,000, 30,000, 40,000, 50,000, 100,000 or 500,000 sequence reads per hour, with at least 50, 60, 70, 80, 90, 100, 120 or 150 bases per read.

High throughput sequencing can involve sequencing-by-synthesis, sequencing-by-ligation, and ultra deep sequencing.

Sequence-by-synthesis can be initiated using sequencing primers complementary to the sequencing element on the nucleic acid tags. The method involves detecting the identity of each nucleotide immediately after (substantially real-time) or upon (real-time) the incorporation of a labeled nucleotide or nucleotide analog into a growing strand of a complementary nucleic acid sequence in a polymerase reaction. After the successful incorporation of a label nucleotide, a signal is measured and then nulled by methods known in the art. Examples of sequence-by-synthesis methods are described in U.S. Application Publication Nos. 2003/0044781, 2006/0024711, 2006/0024678 and 2005/0100932. Examples of labels that can be used to label nucleotide or nucleotide analogs for sequencing-by-synthesis include, but are not limited to, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, and electrochemical detection moieties. Sequencing-by-synthesis can generate at least 1,000, at least 5,000, at least 10,000, at least 20,000, 30,000, at least 40,000, at least 50,000, at least 100,000 or at least 500,000 reads per hour. Such reads can have at least 50, at least 60, at least 70, at least 80, at least 90, at least 100, at least 120 or at least 150 bases per read.

Another sequencing method involves hybridizing the amplified regions to a primer complementary to the sequence element in an LST. This hybridization complex is incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) are added sequentially. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process is repeated until the entire sequence is determined.

Yet another sequencing method involves a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structure such that the identity of one of its positions is correlated with the identity of the fluorophore attached to that nonamer. To the extent that the ligase discriminates for complementarily at that queried position, the fluorescent signal allows the inference of the identity of the base. After performing the ligation and four-color imaging, the anchor primer: nonamer complexes are stripped and a new cycle begins. Methods to image sequence information after performing ligation are known in the art.

In some cases, high throughput sequencing involves the use of ultra-deep sequencing, such as described in Marguiles et al., Nature 437 (7057): 376-80 (2005). Briefly, the amplicons are diluted and mixed with beads such that each bead captures a single molecule of the amplified material. The DNA molecule on each bead is then amplified to generate millions of copies of the sequence which all remain bound to the bead. Such amplification can occur by PCR. Each bead can be placed in a separate well, which can be a (optionally addressable) picolitre-sized well. In some embodiments, each bead is captured within a droplet of a PCR-reaction-mixture-in-oil-emulsion and PCR amplification occurs within each droplet. The amplification on the bead results in each bead carrying at least one million, at least 5 million, or at least 10 million copies of the original amplicon coupled to it. Finally, the beads are placed into a highly parallel sequencing by synthesis machine which generates over 400,000 reads (~100 bp per read) in a single 4 hour run.

Other methods for ultra-deep sequencing that can be used are described in Hong, S. et al. Nat. Biotechnol. 22(4):435-9 (2004); Bennett, B. et al. Pharmacogenomics 6(4):373-82 (2005); Shendure, P. et al. Science 309 (5741):1728-32 (2005).

The microarray or sequencing methods described herein provide a readout, which can be visualized via apparatus and methods known in the art. For example, for a given marker or at a given tag probe position, the fluorescence intensity of each of the fluorophores utilized (e.g., tagged sequencing or PCR primers) provides a signal which is detected by apparatus or automated systems/machines known in the art. The fluorophore markers can be utilized either in an array-based or sequencing-based analysis.

In step 151, SNP data is used to determine aneuploidy by, e.g., determining the ratio of material allele(s) to paternal allele(s) (or vice versa); or determining ratio of maternal allele(s) in a region suspected of aneuploidy versus in a control region.

Aneuploidy means the condition of having less than or more than the normal diploid number of chromosomes. In other words, it is any deviation from euploidy. Aneuploidy includes conditions such as monosomy (the presence of only one chromosome of a pair in a cell's nucleus), trisomy (having three chromosomes of a particular type in a cell's nucleus), tetrasomy (having four chromosomes of a particular type in a cell's nucleus), pentasomy (having five chromosomes of a particular type in a cell's nucleus), triploidy (having three of every chromosome in a cell's nucleus), and tetraploidy (having four of every chromosome in a cell's nucleus). Birth of a live triploid is extraordinarily rare and such individuals are quite abnormal, however triploidy occurs in about 2-3% of all human pregnancies and appears to be a factor in about 15% of all miscarriages. Tetraploidy occurs in approximately 8% of all miscarriages. (www.e-medicine.com/med/topic3241.htm).

In one embodiment, kits are provided which include a separation device, optionally a capture device and the reagents and devices used for the analysis of the genomic sequences. For example, the kit may include the separation arrays and DNA microarrays for detecting one or more SNPs. Any of the devices mentioned for the DNA determination may be combined with the separation devices. The combination of the array separation devices with DNA analysis devices provides gentle handling and accurate analysis.

A simple intuitive understanding of the effect of trisomy is that it increase the abundances of fetal alleles at loci within the affected region. Trisomies are predominately from maternal non-dysjunction events, so typically both maternal alleles, and a single paternal allele, are increased, and the ratio of maternal allele abundance to paternal allele abundance is higher in the trisomic region. These signatures may be masked by differences in DNA amplification and hybridization efficiency from locus to locus, and from allele to allele.

In one embodiment, trisomies are determined by comparing abundance (e.g. intensities) of maternal and paternal alleles in a genomic region. Within a locus, the PCR differences are smaller than between loci, because the same primers are responsible for all the different allele amplicons at that locus. Therefore, the allele ratios may be more stable than the overall allele abundances. This can be exploited by identifying loci where the paternal allele is distinct form the maternal allele and taking the ratio of the paternal allele strength to the average of the maternal allele strengths. These allele ratios then can be averaged over the hypothesized aneuploidy region and compared to the average over a control region. The distributions of these ratio values in the hypothesized aneuploidy region and in the control region can be compared to create an estimate of statistical significance for the observed difference in means. A simple example of this procedure would use Student's t-test.

Thus, the present invention contemplates detection of fetal abnormality by determining a ratio of abundance of maternal allele(s) and abundance of paternal allele(s) (or vice versa) in one or more genomic regions of interest. (Preferably the paternal allele differs from one or both the maternal alleles). The genomic region can be derived from a mixed sample comprising fetal and maternal cells. The sample can be obtained from a pregnant animal and can be, e.g., a blood sample. In some cases, the genomic region includes a SNP and/or an informative SNP. In some cases at least 10, 20, 50, 100, 200 or 500 SNPs are analyzed per sample. The SNPs analyzed can be in a single locus, different loci, single chromosome, or different chromosomes. In some cases, a first genomic region (SNP) analyzed is in a genomic region suspected of being trisomic or is trisomic and a second genomic region (SNP) analyzed is in a control region that is non-trisomic or a region suspected of being non-trisomic. The ratio of alleles (e.g., maternal/paternal) in a first genomic region or first plurality of genomic regions (trisomic) (hereinafter test regions) is then compared with a ratio of alleles (e.g., maternal/paternal) in the second genomic region or second plurality of genomic regions (hereinafter control regions). The control region(s) and test region(s) can be on the same or different chromosomes. In some instances, comparison is made by determining the difference in means of the ratios in the first regions and second regions. Detection of an increase of paternal abundance in the test region(s) is indicative of paternal trisomy, while detection of an increase of maternal abundance in the first region(s) is indicative of maternal trisomy.

Furthermore, calculation of error rate based on amplification can be performed prior to making a call if a fetus has a specific condition (e.g., trisomy) or not.

Alternatively, the maternal allele strengths over the suspected aneuploidy region(s) can be compared to those in the control region(s), all without forming ratios to paternal alleles. In this approach, errors in the measurement of the paternal allele abundances are not calculated. However, differences in amplification efficiency between primer pairs are calculated. These measurements can be larger than differences between alleles in the same locus. In this approach there also may be a residual bias between the efficiencies averaged over certain chromosomes. Therefore it may be useful to also perform the same detection process in a reference sample (e.g. maternal only cell sample) and then take the ratio of ratios. In other words, the ratio obtained for the mixed sample of the abundance in test genomic region(s) and control genomic region(s) divided by the same ratio obtained from the reference sample. The ratios obtained for the mixed and reference samples reflect allele strength over suspected aneuploidy region over allele strength over control region, and the ratio of ratios presents an estimate that is normalized to the reference (maternal) sample. Such ratio of ratios is therefore free of chromosome bias, but may include errors in the measurements of the reference sample, as that sample is used as the control or normalizer.

In some cases, the methods herein contemplate detecting fetal abnormality by comparing an abundance of one or more maternal allele(s) in a first genomic region or regions (test region(s)) with one or more maternal alleles in a second genomic region or regions (control region(s)) in a mixed sample (e.g., maternal blood sample from pregnant animal). This ratio can then be compared to a similar ratio measured in a control sample (e.g., maternal-cell only sample). The control sample can be a diluted subset of the mixed sample, wherein the dilution is by a factor of at least 10, 100, 1000, or 10,000. In some cases, such methods further involve estimating the number of fetal cells in the mixed sample. This can be performed by, e.g., ranking the alleles detected according to their abundance. The ranking can be used to determine abundance of one or more paternal alleles. Ranking is described in more detail herein.

Aneuploidy can be determined by modeling SNP data. One example of a model for SNP data in the context of fetal diagnosis is given in Equations 1-3 below.

A normal (diploid) fetus result in data $x_k$ at locus k and is represented by:

$$x_k = A_k[(1-f)(m_{k1}+m_{k2})+f((m_{k1} \text{ or } m_{k2})+p_k)]+\text{residual} \quad (1)$$

A trisomy caused by maternal non-dysjunction is represented by $$x_k = A_k[(1-f)(m_{k1}+m_{k2})+f(m_{k1}+m_{k2}+p_k)]+\text{residual} \quad (2)$$

and a paternally inherited trisomy is represented by $$x_k = A_k[(1-f)(m_{k1}+m_{k2})+f((m_{k1} \text{ or } m_{k2})+p_{k1}+p_{k2})]+\text{residual} \quad (3)$$

In Equations 1-3, $A_k$ denotes a scale factor which subsumes the efficiencies of amplification, hybridization, and readout common to the alleles at locus k. In this model amplification differences between different primer pairs are fitted and do not appear in the residuals. Alternatively, a single A parameter could be used and the residuals would reflect these differences. Further, f represents the fraction of fetal cells in the mixture, $m_{k1}$ and $m_{k2}$ denote the maternal alleles at locus k, and $p_k$ denotes the paternal allele at locus k. The allele symbols actually represent unit data contributions that can be arithmetically summed; e.g., $m_{k1}$ might be a detection of the 'C' genotype represented by unit contribution to the 'C' bin at that locus.

Figure 6:
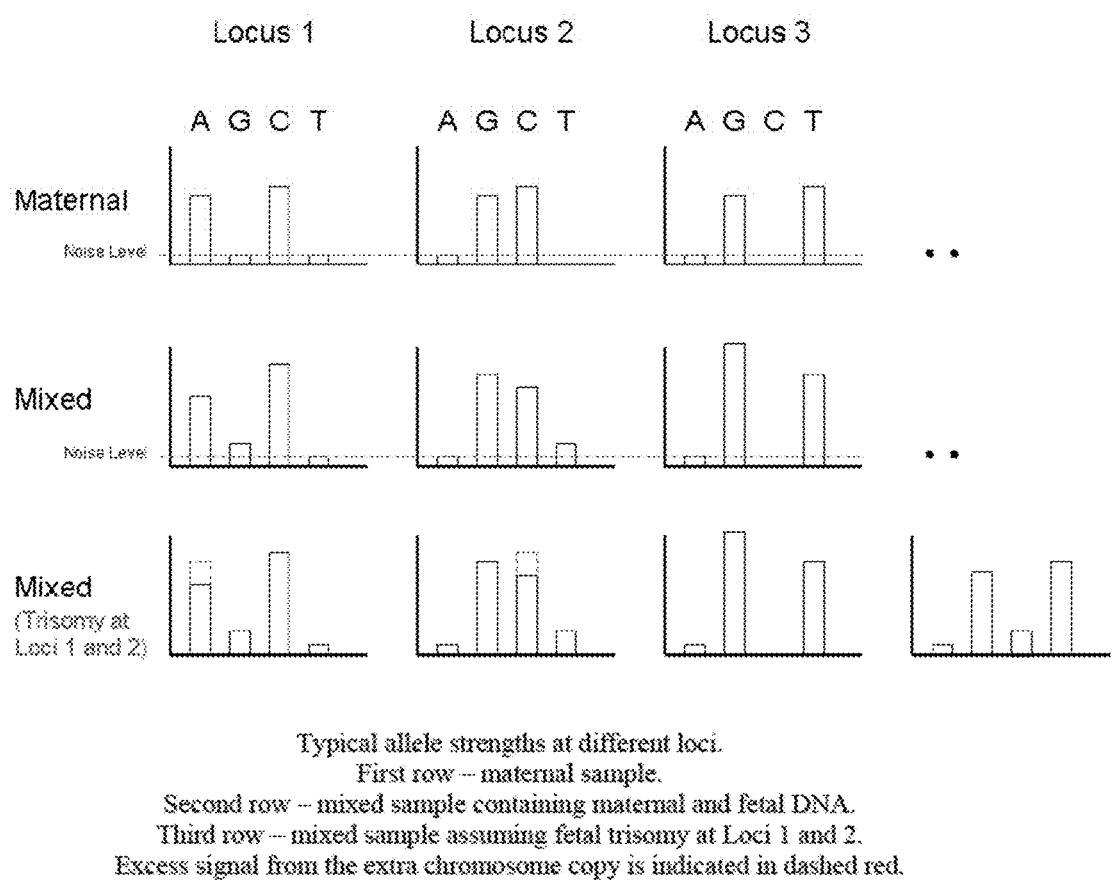
FIG. 6 illustrates the types of SNP calls that result depicting allele strengths at different loci.

FIG. 6 illustrates the SNP calls that result under this data model. At Locus 1, the fetal genotype was GC. There is a paternally inherited 'G' allele contribution in the mixed sample that results in an increase of G signal above the noise level observed in the maternal-only sample, and a maternally inherited 'C' allele contribution that increases the C signal. The effective value that has been assumed in these illustrations is f=0.2. At Locus 2, the paternal allele is 'T'. At Locus 3, the fetus is homozygous GG. In the third row of FIG. 2, the effect of a fetal trisomy is represented by the dashed red lines, superposed on a normal (diploid) mixed-sample pattern. The trisomy is assumed to include Loci 1 and 2, but not Loci 3 and 4. At Loci 1 and 2 both maternal allele strengths are increased in the mixed sample, as well as the separate paternal allele contribution. At Locus 3, it was assumed that the fetus was 'GG' and the paternal allele is the same as the first maternal allele. Note that the ratio between the average of the two maternal alleles and the paternal allele will be slightly greater at Loci 1 and 2 than at Locus 4—this is one indicator of trisomy.

The location and abundance of SNPs can be used to determine whether the fetus has an abnormal genotypes, such as Down syndrome or Kleinfelter Syndrome (XXY). Other examples of abnormal fetal genotypes include, but are not limited to, aneuploidy such as, monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g. XXXX, XXYY, XXXY, XYYY, XXXXXX, XXXXY, XXXYY, XYYYY and XXYYY), triploidy (three of every chromosome, e.g. 69 chromosomes in humans), tetraploidy (four of every chromosome, e.g. 92 chromosomes in humans) and multiploidy. In some embodiments, an abnormal fetal genotype is a segmental aneuploidy. Examples of segmental aneuploidy include, but are not limited to, 1p36 duplication, dup(17)(p11.2p11.2) syndrome, Down syndrome, Pelizaeus-Merzbacher disease, dup(22)(q11.2q11.2) syndrome, and cat-eye syndrome. In some cases, an abnormal fetal genotype is due to one or more deletions of sex or autosomal chromosomes, which may result in a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azospermia (factor a), Azospermia (factor b), Azospermia (factor c), or 1p36 deletion. In some embodiments, a decrease in chromosomal number results in an XO syndrome.

In some cases, data models are fitted for optimal detection of aneuploidy. For example, the data models can be used to simultaneously recover estimates of the fraction of fetal cells, and efficient detection of aneuploidy in hypothesized chromosomes or chromosomal segments. This integrated approach results in more reliable and sensitive declarations of aneuploidy.

Equations 1-3 represent five different models because of the ambiguity between $m_{k1}$ and $m_{k2}$ in the last term of Equations 1 and 3. In other words, since Equation 1 and 3 are different and in each equation there are two possibilities (i.e., $m_{k1}$ or $m_{k2}$) then it follows that each of Equations 1 and 3 represent two different models. Therefore, Equations 1-3 represent five different models. Testing for aneuploidy of Chromosomes 13, 18, and 21, for example entails 5×5×5=125 different model variants that would be fit to the data.

The parameter values for the maternal allele identities are taken from the results for the reference (i.e. maternal-only) sample and the remaining parameters are fit to the data from the mixed sample. Because the number of parameters is very large when the number of loci is large, a global optimization requires iterative search techniques. One possible approach is to do the following for each model variant i) Set f to 0 and solve for $A_k$ at each locus.
ii) Set f to a value equal to the smallest fetal/maternal cell ratio for which fetal cells are likely to be detectable.
iii) Solve for paternal allele(s) identities and strengths at each locus, one locus at a time, that minimize data-model residuals.
iv) Fix the paternal alleles and adjust f to minimize residuals over all the data.
v) Now vary only the $A_k$ to minimize residuals. Repeat iv and v until convergence.
vi) Repeat iii through v until convergence.

The best overall fit of model to data is selected from among all the model variants. The best overall fit yields the values of f and $A_k$ we will call $f_{max}$, $A_{kmax}$. The likelihood of observing the data given $f_{max}$ can be compared to the likelihood given f=0. The ratio is a measure of the amount of evidence for fetal DNA. A typical threshold for declaring fetal DNA would be a likelihood ratio of ~1000 or more. The likelihood calculation can be approximated by a more familiar Chi-squared calculation involving the sum of squared residuals between the data and the model, where each residual is normalized by the expected rms error. This Chi-squared is a good approximation to the Log(likelihood) to the extent the expected errors in the data are Gaussian additive errors, or can be made so by some amplitude transformation of the data.

If based on the above determination of likelihood ratio it is decided that fetal DNA is not present, then the test is declared to be non-informative. If it is decided that fetal DNA is present, then the likelihoods of the data given the different data model types can be compared to declare aneuploidy. The likelihood ratios of aneuploidy models (Equations 2 and 3) to the normal model (Equation 1) are calculated and these ratios are compared to a predefined threshold. Typically this threshold is set so that in controlled tests all the trisomic cases are declared aneuploid. Thus, it is expected that the vast majority (>99.9%) of all truly trisomic cases are declared aneuploid by the test. Another approach to accomplish approximately the 99.9% detection rate is to increase the likelihood ratio threshold beyond that necessary to declare all the known trisomic cases in the validation set by a factor of 1000/N, where N is the number of trisomy cases in the validation set.

Figure 7:
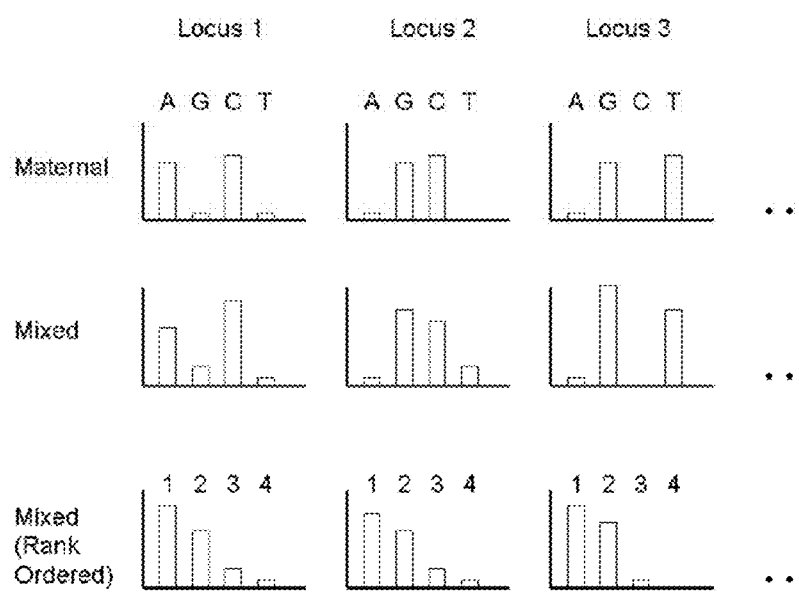
FIG. 7 illustrates the concept of rank ordering of allele strengths.
Figure 8:
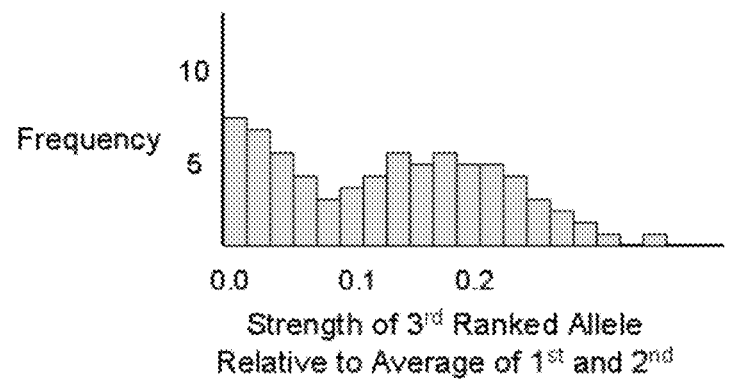
FIG. 8 illustrates a histogram of paternal allele strength normalized relative to maternal alleles.
Figure 9:
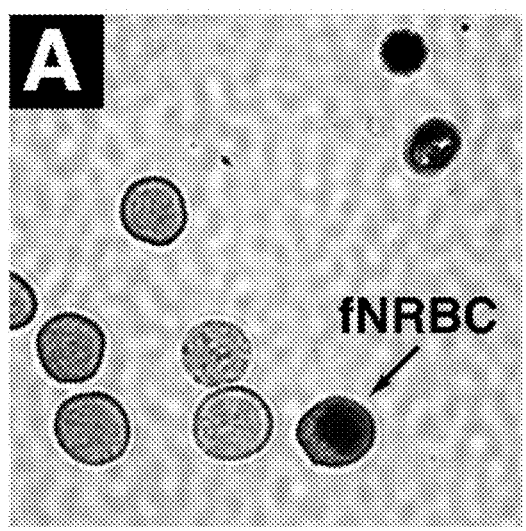
FIGS. 9A-9B illustrate cell smears of the product and waste fractions.
Figure 9:
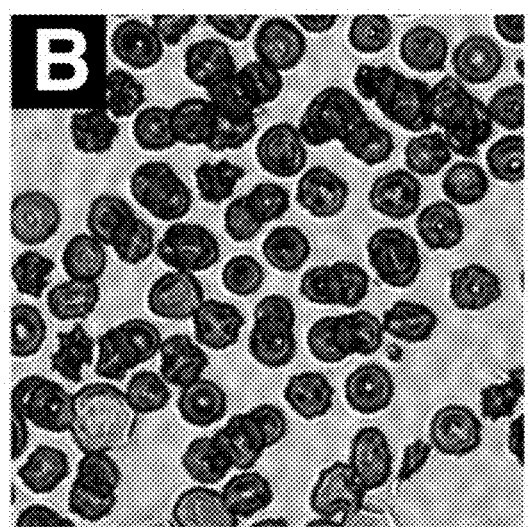

In step 161 (FIG. 1), which is optional, the presence of fetal cells and ratio of fetal alleles/maternal alleles is determined. Because the fraction of fetal cells can be small or even zero, the aneuploidy signal (the departure of the observed ratio from unity) may be weak even when fetal aneuploidy is present. An independent estimate of fetal cell fraction, including a confidence estimate of whether measurable fetal DNA is present at all, is useful in interpreting the observed aneuploidy ratios. FIG. 7 illustrates allele signals re-ordered by rank. Assuming the mother has no more than two alleles at each locus, the magnitude of the third ranked allele is potentially a robust indicator of the presence of fetal DNA. Although measurement errors can artificially inflate the size of the third and fourth alleles, it is very unlikely to result in a bimodal distribution for the relative magnitude of the third allele with respect to the first two. Such a bimodal distribution is illustrated in FIG. 8. The secondary peak of this distribution occurs at a value approximately equal to the fraction of fetal cells. (This is one way to determine the value of the variable fin the data model.) The statistical confidence that the bimodality is real can be used to assign a confidence that fetal DNA was present in the mixed sample. Statistical tests for bimodality are discussed in M. Y. Cheng and P. Hall, *J.R. Statist.* Soc. B (1998), 60 (Part 3) pp. 579-589. If this confidence level exceeds a threshold, e.g., 90%, 95%, 99% or 99.9%, an aneuploidy call may be made. The threshold set can be stringent (e.g. 99.9%) to avoid declaring a fetus normal when in fact it is not. Thus, the independently estimated fetal cell fraction can be used to interpret the aneuploidy statistic. For example, a value f=0.5 along with an estimated aneuploidy ratio from the fetal-maternal mixture of 0.05±0.01 would weaken the evidence for aneuploidy because the ratio is too small to be consistent with the independently determined f value (the ratio should be ~1+f/2). As another example, a value f=0.1 along with an estimated aneuploidy ratio from the fetal-maternal mixture of 0.05±0.02 would tend to strengthen the evidence for aneuploidy because the observed ratio is consistent with the independently derived value of f.

In any of the embodiments herein SNP data may be analyzed for possible errors. For example, in some instances SNP data can contain small additive errors associated with the readout technology, multiplicative errors associated with DNA amplification and hybridization efficiencies being different from locus to locus and from allele to allele within a locus, and errors associated with imperfect specificity in the process. By including the many parameters (Ak) in the model, rather than a single scale parameter, the residuals include allele-to-allele efficiency differences but not locus to locus differences. These tend to be multiplicative errors in the resulting observed allele strengths heights (e.g., two signals may be 20% different in strength although the starting concentrations of the alleles are identical). In other words, by providing ninny parameters, the errors that are otherwise attributable to locus to locus differences, are minimized. As a first approximation, one can assume errors are random from allele to allele; errors have relatively small additive measurement noise error components; and larger Poisson and multiplicative error components exist. The magnitudes of these error components can be estimated from repeated processing of identical samples. A Chi-square residuals calculation for any data-model fit then can be supported with these modeled squared errors for any peak height or data bin.

For example, we anticipate a large scale SNP genotyping platform such as the Golden Gate assay by Illumina will provide ~100 SNP loci per chromosome of interest. Measurements of repeated 'normal' pregnancy samples would give ratios of paternal to maternal allele strengths which varied by ~20% due to assay errors. Averaged over the 100 loci in a chromosome, the ratio error would be reduced to 20%/sqrt(100), or ~2%. For an assumed fetal/maternal cell ratio of 0.2 in a sample, the expected observed aneuploidy ratio in the case of a trisomy would be 1.10 with an estimation error of 0.02, yielding a confident (5 sigma) detection of aneuploidy.

Alternatively, when using a single A parameter, the residuals will be larger and will contain a component which is correlated between alleles at the same locus. Calculation of likelihood will need to take this correlation into account.

Another aspect of the invention involves a computer executable logic for determining the presence of fetal cells in a mixed sample and fetal abnormalities and/or conditions in such cells. A computer program product is described comprising a computer usable medium having the computer executable logic (computer software program, including program code) stored therein. Computer executable logic when executed by the processor causes the processor to perform one or more functions described herein. For example, a computer executable logic can be utilized to automate, process or control sample collection, sample enrichment, pre-amplification, SNP data modeling, estimating fetal/maternal allele ratio, comparing maternal allele intensity from suspected aneuploid region and control region and determining the existence of aneuploidy and the type of aneuploidy if one exists.

For example, the computer executable logic can determine the presence and ratio of fetal cells to maternal cells in a mixed sample. The executable code can also receive data for one or more SNPs, and apply such data to one or more data models. The computer executable logic can then calculate a set of values for each of the data sets associated with each data model; select the data model that best fit the data, model and calculate for any potential errors in the data models; for example, a computer executable logic can determine the ratio of maternal alleles to paternal alleles in one or more SNP locations; and/or the ratio of maternal alleles in a region suspected of aneuploidy and a control region. One example of a data model provides a determination of a fetal abnormality from given data signals of SNPs at two genomic regions. The executable logic can establish the presence or absence of trisomy, and conclude whether the trisomy is paternally derived or if it originated from a maternal non-disjunction event. For example, the program can fit SNP data to the following model, which can provide the diagnosis as follows:

A normal (diploid) fetus result in data $x_k$ at locus k and is represented by:

$$x_k = A_k[(1-f)(m_{k1}+m_{k2})+f((m_{k1} \text{ or } m_{k2})+p_k)] + \text{residual} \quad (1)$$

A trisomy caused by maternal non-dysjunction is represented by $$x_k = A_k[(1-f)(m_{k1}+m_{k2})+f(m_{k1}+m_{k2}+p_k)] + \text{residual} \quad (2)$$

and a paternally inherited trisomy is represented by $$x_k = A_k[(1-f)(m_{k1}+m_{k2})+f((m_{k1} \text{ or } m_{k2})+p_{k1}+p_{k2})] + \text{residual} \quad (3)$$

In Equations 1-3, $A_k$ denotes a scale factor which subsumes the efficiencies of amplification, hybridization, and readout common to the alleles at locus k. In this model amplification differences between different primer pairs are fitted and do not appear in the residuals. Alternatively, a single A parameter could be used and the residuals would reflect these differences. Further, f represents the fraction of fetal cells in the mixture, $m_{k1}$ and $m_{k2}$ denote the maternal alleles at locus k, and $p_k$ denotes the paternal allele at locus k. The allele symbols actually represent unit data contributions that can be arithmetically summed; e.g., $m_{k1}$ might be a detection of the 'C' genotype represented by unit contribution to the 'C' bin at that locus.

In some cases, the computer executable logic records data measurements corresponding to readouts (e.g., SNP intensities from DNA microamap or a sequencing machine. Such measurements can be processed by the computer executable logic to determine fetal/maternal allele ratios and provide a call with result with respect to detection of aneuploidy. Moreover, computer executable logic can control display of such results in print or electronic formats, which an operator can view. Thus, a computer executable logic can include code for receiving data on one or more target DNA polymorphisms (i.e. SNP loci); calculating a set of values for each of the data sets associated with each data model; selecting the data model that best fit the data, wherein the best model will be an indication of the presence of fetal cells in the mixed sample and fetal abnormalities and/or conditions in said cells. The determination of presence of fetal cells in the mixed sample and fetal abnormalities and/or conditions in said cells can be made by the computer executable logic or an user. Therefore, the computer based logic can provide results for estimating fetal/maternal ratios, allele strength and aneuploidy, which can be observed by a technician or operator.

EXAMPLES

Example 1. Separation of Fetal Cord Blood

FIG. 12A-D shows a schematic of the device used to separate nucleated cells from fetal cord blood.

Dimensions: 100 mm×28 mm×1 mm

Array design: 3 stages, gap size=18, 12 and 8 μm for the first, second and third stage, respectively.

Device fabrication: The arrays and channels were fabricated in silicon using standard photolithography and deep silicon reactive etching techniques. The etch depth is 140 μm. Through holes for fluid access are made using KOH wet etching. The silicon substrate was sealed on the etched face to form enclosed fluidic channels using a blood compatible pressure sensitive adhesive (9795, 3M, St Paul, Minn.).

Device packaging: The device was mechanically mated to a plastic manifold with external fluidic reservoirs to deliver blood and buffer to the device and extract the generated fractions.

Device operation: An external pressure source was used to apply a pressure of 2.0 PSI to the buffer and blood reservoirs to modulate fluidic delivery and extraction from the packaged device.

Experimental conditions: Human fetal cord blood was drawn into phosphate buffered saline containing Acid Citrate Dextrose anticoagulants. 1 mL of blood was processed at 3 mL/hr using the device described above at room temperature and within 48 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.) and 2 mM EDTA (15575-020, Invitrogen, Carlsbad, Calif.).

Measurement techniques: Cell smears of the product and waste fractions (FIG. 8A-8B) were prepared and stained with modified Wright-Giemsa (WG16, Sigma Aldrich, St. Louis, Mo.).

Performance: Fetal nucleated red blood cells were observed in the product fraction (FIG. 8A) and absent from the waste fraction (FIG. 8B).

Example 2: Isolation of Fetal Cells from Maternal Blood

The device and process described in detail in Example 1 were used in combination with immunomagnetic affinity enrichment techniques to demonstrate the feasibility of isolating fetal cells from maternal blood.

Experimental conditions: blood from consenting maternal donors carrying male fetuses was collected into K$_2$EDTA vacutaineis (366643, Becton Dickinson, Franklin Lakes, N.J.) immediately following elective termination of pregnancy. The undiluted blood was processed using the device described in Example 1 at mom temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.). Subsequently, the nucleated cell fraction was labeled with anti-CD71 microbeads (130-046-201, Miltenyi Biotech Inc., Auburn, Calif.) and enriched using the MiniMACS™ MS column (130-042-201, Miltenyi Biotech Inc., Auburn, Calif.) according to the manufacturer's specifications. Finally, the CD71-positive fraction was spotted onto glass slides.

Measurement techniques: Spotted slides were stained using fluorescence in situ hybridization (FISH) techniques according to manufacturer's specifications using Vysis probes (Abbott Laboratories, Downer's Grove, Ill.). Samples were stained from the presence of X and Y chromosomes. In one case, a sample prepared from a known Trisomy 21 pregnancy was also stained for chromosome 21.

Figure 11:
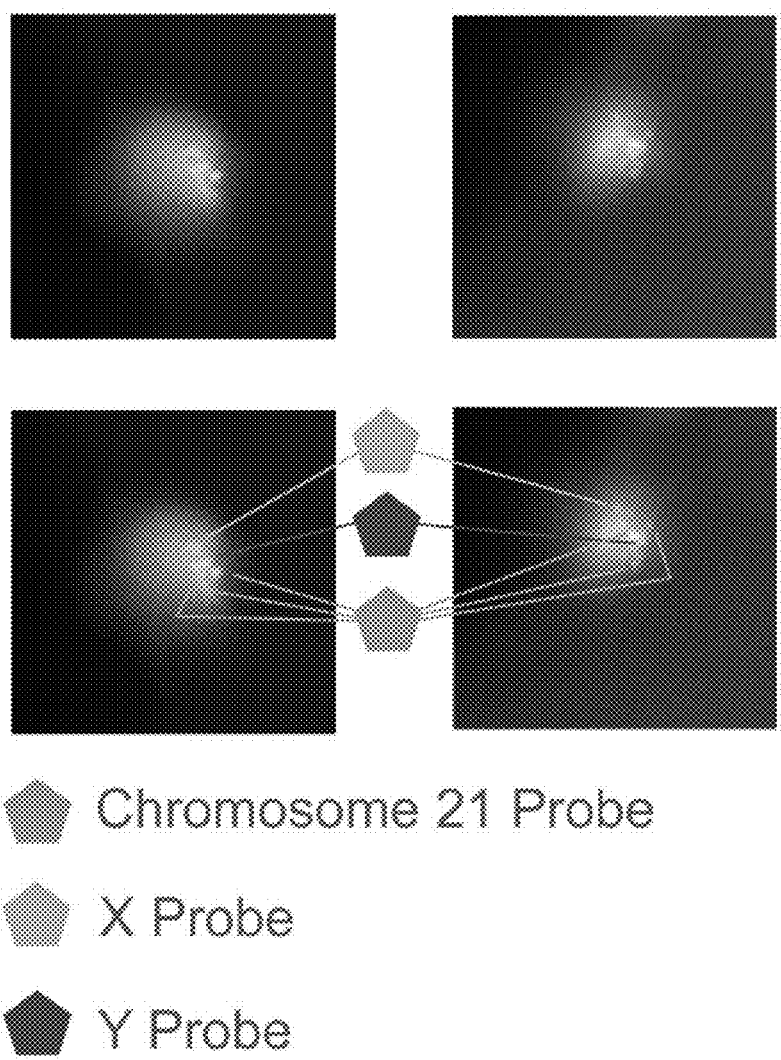
FIG. 11 illustrates trisomy 21 pathology in an isolated fetal nucleated red blood cell.
Figure 12A:
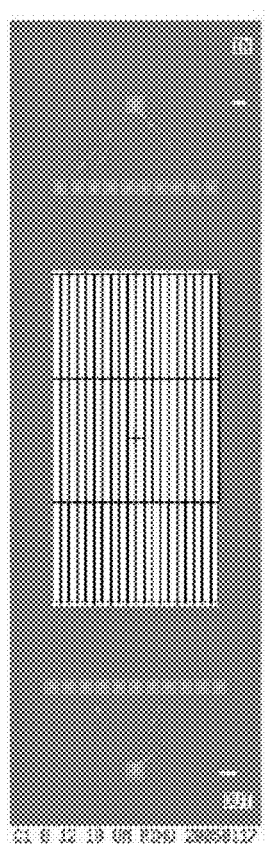
FIG. 12A-12D illustrate various embodiments of a size-based separation module.
Figure 12B:
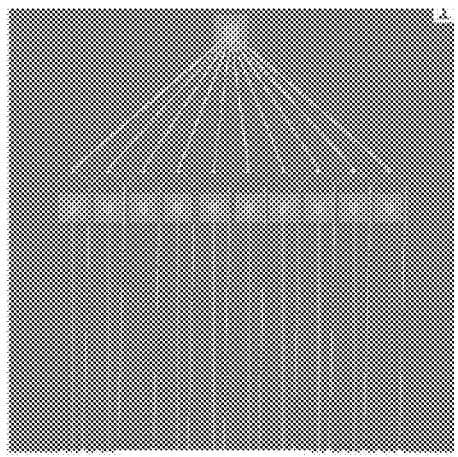
Figure 12C:
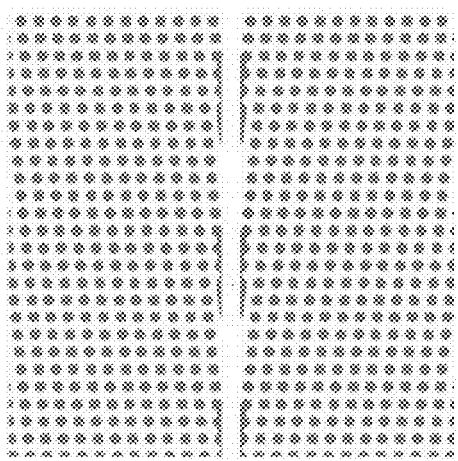
Figure 12D:
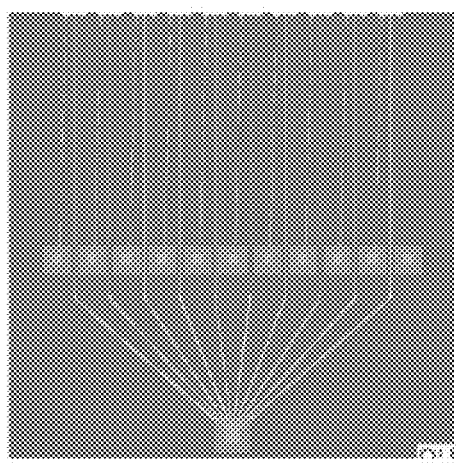

Performance: Isolation of fetal cells was confirmed by the reliable presence of male cells in the CD71-positive population prepared from the nucleated cell fractions (FIGS. 10A-10F). In the single abnormal case tested, the trisomy 21 pathology was also identified (FIG. 11).

Example 3. Confirmation of the Presence of Male Fetal Cells in Enriched Samples

Confirmation of the presence of a male fetal cell in an enriched sample is performed using qPCR with primers specific for DYZ, a marker repeated in high copy number on the Y chromosome. After enrichment of fnRBC by any of the methods described herein, the resulting enriched fnRBC are binned by dividing the sample into 100 PCR wells. Prior to binning, enriched samples may be screened by FISH to determine the presence of any fnRBC containing an aneuploidy of interest. Because of the low number of fnRBC in maternal blood, only a portion of the wells will contain a single fnRBC (the other wells are expected to be negative for fnRBC). The cells are fixed in 2% Paraformaldehyde and stored at 4° C. Cells in each bin are pelleted and resuspended in 5 PBS plus 1 µl 20 mg/ml Proteinase K (Sigma #P-2308). Cells are lysed by incubation at 65° C. for 60 minutes followed by inactivation of the Proteinase K by incubation for 15 minutes at 95° C. For each reaction, primer sets (DYZ forward primer TCGAGTGCATTCCATTCCG (SEQ ID NO:1); DYZ reverse primer ATGGAATGGCATCAAACG-GAA (SEQ ID NO:2); and DYZ Tagman Probe 6FAM-TGGCTGTCCATTCCA-MGBNFQ (SEQ ID NO: 3)), TaqMan Universal PCR master mix, No AmpErase and water are added. The samples are run and analysis is performed on an ABI 7300: 2 minutes at 50° C., 10 minutes 95° C. foll2wed by 40 cycles of 95° C. (15 seconds) and 60° C. (1 minute). Following confirmation of the presence of male fetal cells, further analysis of bins containing fnRBC is performed. Positive bins may be pooled prior to further analysis.

Figure 13:
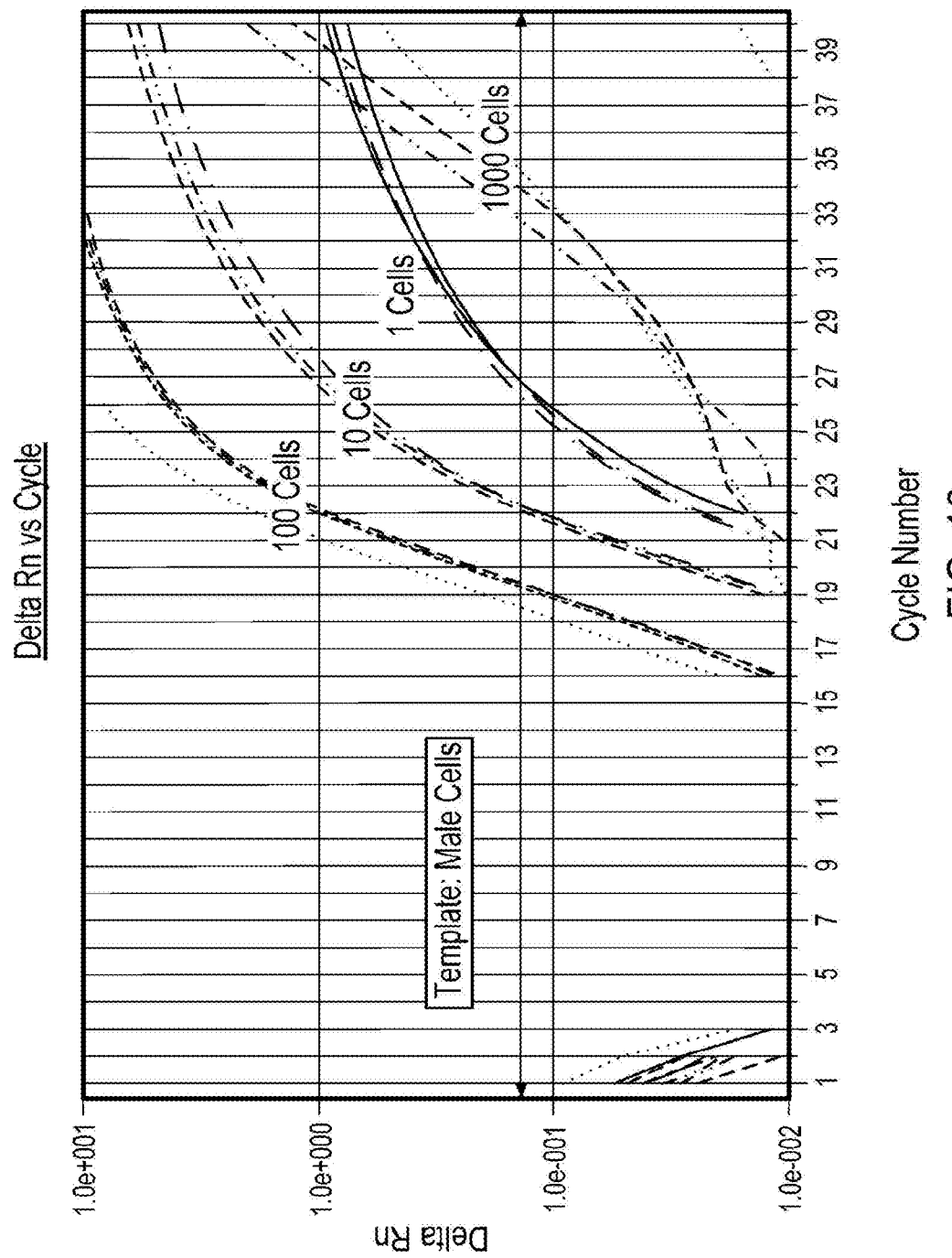
FIG. 13 illustrates the detection of single copies of a fetal cell genome by qPCR.

FIG. 13 shows the results expected from such an experiment. The data in FIG. 13 was collected by the following protocol. Nucleated red blood cells were enriched from cord cell blood of a male fetus by sucrose gradient two Heme Extractions (HE). The cells were fixed in 2% paraformaldehyde and stored at 4° C. Approximately 10×1000 cells were pelleted and resuspended each in 5 µl PBS plus 1 µl 20 mg/ml Proteinase K (Sigma #P-2308). Cells were lysed by incubation at 65° C. for 60 minutes followed by a inactivation of the Proteinase K by 15 minute at 95° C. Cells were combined and serially diluted 10-fold in PBS for 100, 10 and 1 cell per 6 µl final concentration were obtained. Six µl of each dilution was assayed in quadruplicate in 96 well format. For each reaction, primer sets (DYZ forward primer TCGAGTGCATTCCATTCCG (SEQ ID NO: 1); 0.9 uM DYZ reverse primer ATGGAATGGCATCAAACGGAA (SEQ ID NO: 2); and 0.5 uM DYZ TaqMan Probe 6FAM-TGGCTGTCCATTCCA-MGBNFQ (SEQ ID NO: 3)), TaqMan Universal PCR master mix, No AmpErase and water were added to a final volume of 25 µl per reaction. Plates were run and analyzed on an ABI 7300: 2 minutes at 50° C., 10 minutes 95° C. followed by 40 cycles of 95° C. (15 seconds) and 60° C. (1 minute). These results show that detection of a single fnRBC in a bin is possible using this method.

Example 4. Confirmation of the Presence of Fetal Cells in Enriched Samples by STR Analysis Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Individual positive cells are isolated by "plucking" individual positive cells from the enhanced sample using standard micromanipulation techniques. Using a nested PCR protocol, STR marker sets are amplified and analyzed to confirm that the FISH-positive aneuploid cell(s) are of fetal origin. For this analysis, comparison to the maternal genotype is typical. An example of a potential resulting data set is shown in Table 2. Non-maternal alleles may be proven to be paternal alleles by paternal genotyping or genotyping of known fetal tissue samples. As can be seen, the presence of paternal alleles in the resulting cells, demonstrates that the cell is of fetal origin (cells #1, 2, 9, and 10). Positive cells may be pooled for further analysis to diagnose genotyping of the fetus, or may be further analyzed individually.

TABLE 2

STR locus alleles in maternal and fetal cells

| DNA Source | STR locus D14S | STR locus D16S | STR locus D8S | STR locus F13B | STR locus vWA |
|---|---|---|---|---|---|
| Maternal alleles | 14, 17 | 11, 12 | 12, 14 | 9, 9 | 16, 17 |
| Cell #1 alleles | | 8 | | | 19 |
| Cell #2 alleles | 17 | | 15 | | |
| Cell #3 alleles | | | 14 | | |
| Cell #4 alleles | | | | | |
| Cell #5 alleles | 17 | 12 | | 9 | |
| Cell #6 alleles | | | | | |
| Cell #7 alleles | | | | | 19 |
| Cell #8 alleles | | | | | |
| Cell #9 alleles | 17 | | 14 | 7, 9 | 17, 19 |
| Cell #10 alleles | | | 15 | | |

Example 5. Confirmation of the Presence of Fetal Cells in Enriched Samples by SNP Analysis Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Samples testing positive with FISH analysis are then binned into 96 microliter wells, each well containing 15 µl of the enhanced sample. Of the 96 wells, 5-10 are expected to contain a single fnRBC and each well should contain approximately 1000 nucleated maternal cells (both WBC and mnRBC). Cells are pelleted and resuspended in 5 µl PBS plus 1 µl 20 mg/ml Proteinase K (Sigma #P-2308). Cells are lysed by incubation at 65° C. for 60 minutes followed by a inactivation of the Proteinase K by 15 minute at 95° C.

In this example, the maternal genotype (BB) and fetal genotype (AB) for a particular set of SNPs is known. The genotypes A and B encompass all three SNPs and differ from each other at all three SNPs. The following sequence from chromosome 7 contains these three SNPs (rs7795605, rs7795611 and rs7795233 indicated in brackets, respectively) (ATGCAGCAAGGCACAGACTAA[G/A]CAAGG-AGA[G/C]GCAAAATTTTC[A/G]TAGGGGAGAGAAA-TGGGTC ATT, SEQ ID NO: 4).

In the first round of PCR, genomic DNA from binned enriched cells is amplified using primers specific to the outer portion of the fetal-specific allele A and which flank the interior SNP (forward primer ATGCAGCAAGGCACA-GACTACG (SEQ ID NO: 5); reverse primer AGAGGG-GAGAGAAATGGGTCATT (SEQ ID NO: 6)). In the second round of PCR, amplification using real time SYBR Green PCR is performed with primers specific to the inner portion of allele A and which encompass the interior SNP (forward primer CAAGGCACAGACTAAGCAAGG-AGAG (SEQ ID NO: 7); reverse primer GGCAAAATTTT-CATAGGGGAGAGAAATGGGTCATT (SEQ ID NO: 8)).

Figure 14:
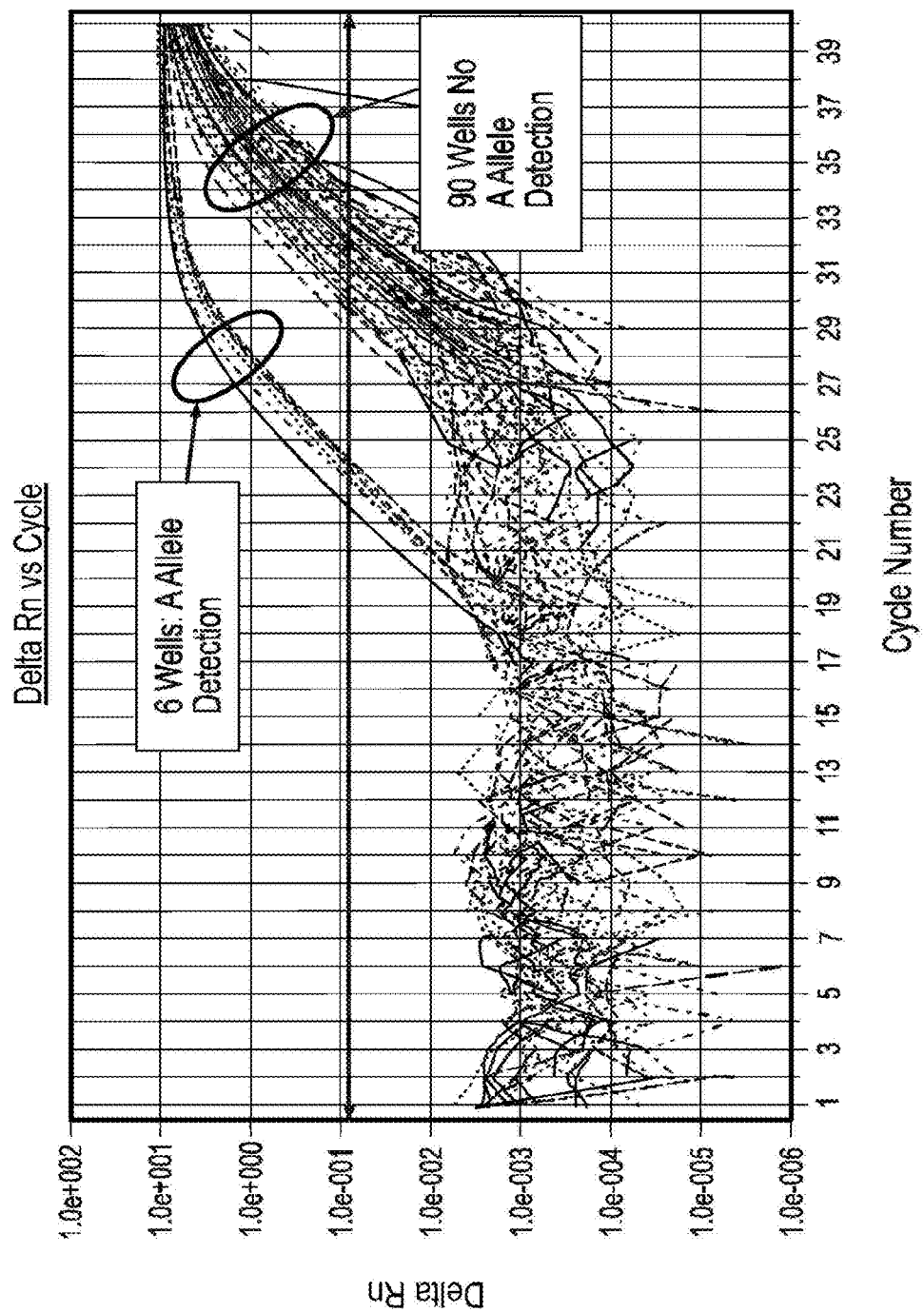
FIG. 14 illustrates detection of single fetal cells in binned samples by SNP analysis.
Figure 15:
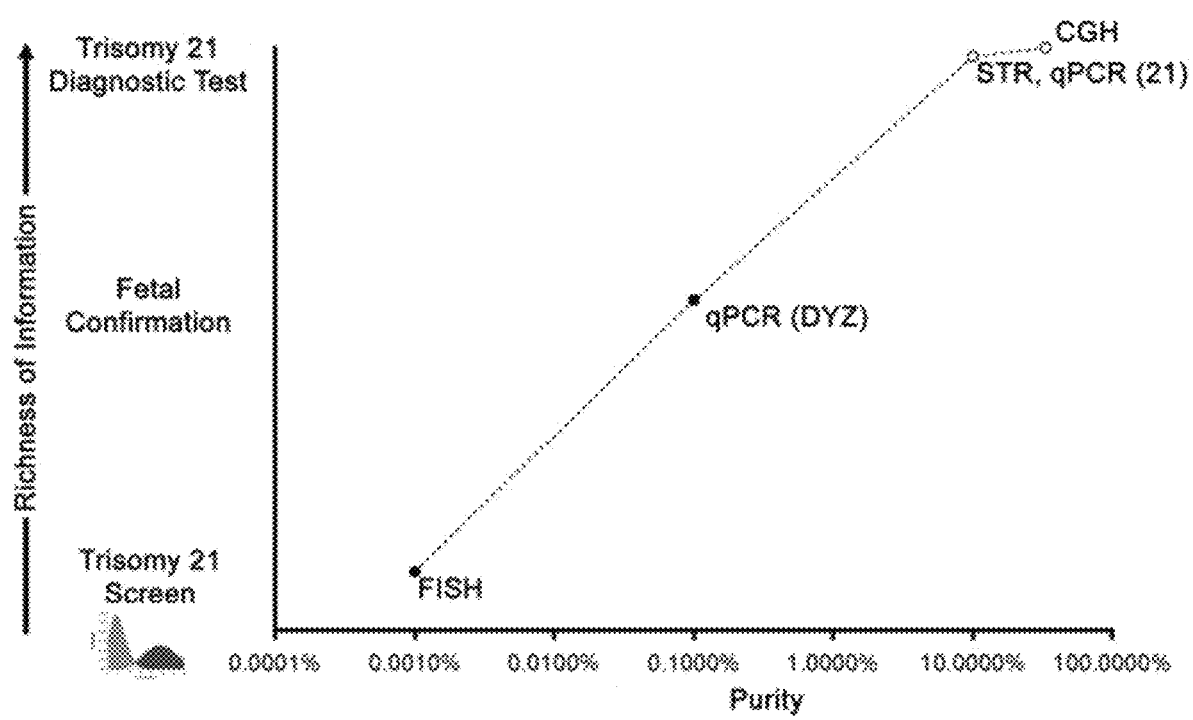
FIG. 15 illustrates a method of trisomy testing. The trisomy 21 screen is based on scoring of target cells obtained from maternal blood. Blood is processed using a cell separation module for hemoglobin enrichment (CSM-HE). Isolated cells are transferred to slides that are first stained and subsequently probed by FISH. Images are acquired, such as from bright field or fluorescent microscopy, and scored. The proportion of trisomic cells of certain classes serves as a classifier for risk of fetal trisomy 21. Fetal genome identification can performed using assays such as: (1) STR markers; (2) qPCR using primers and probes directed to loci, such as the multi-repeat DYZ locus on the Y-chromosome; (3) SNP detection; and (4) CGH (comparative genome hybridization) array detection.
Figure 16:
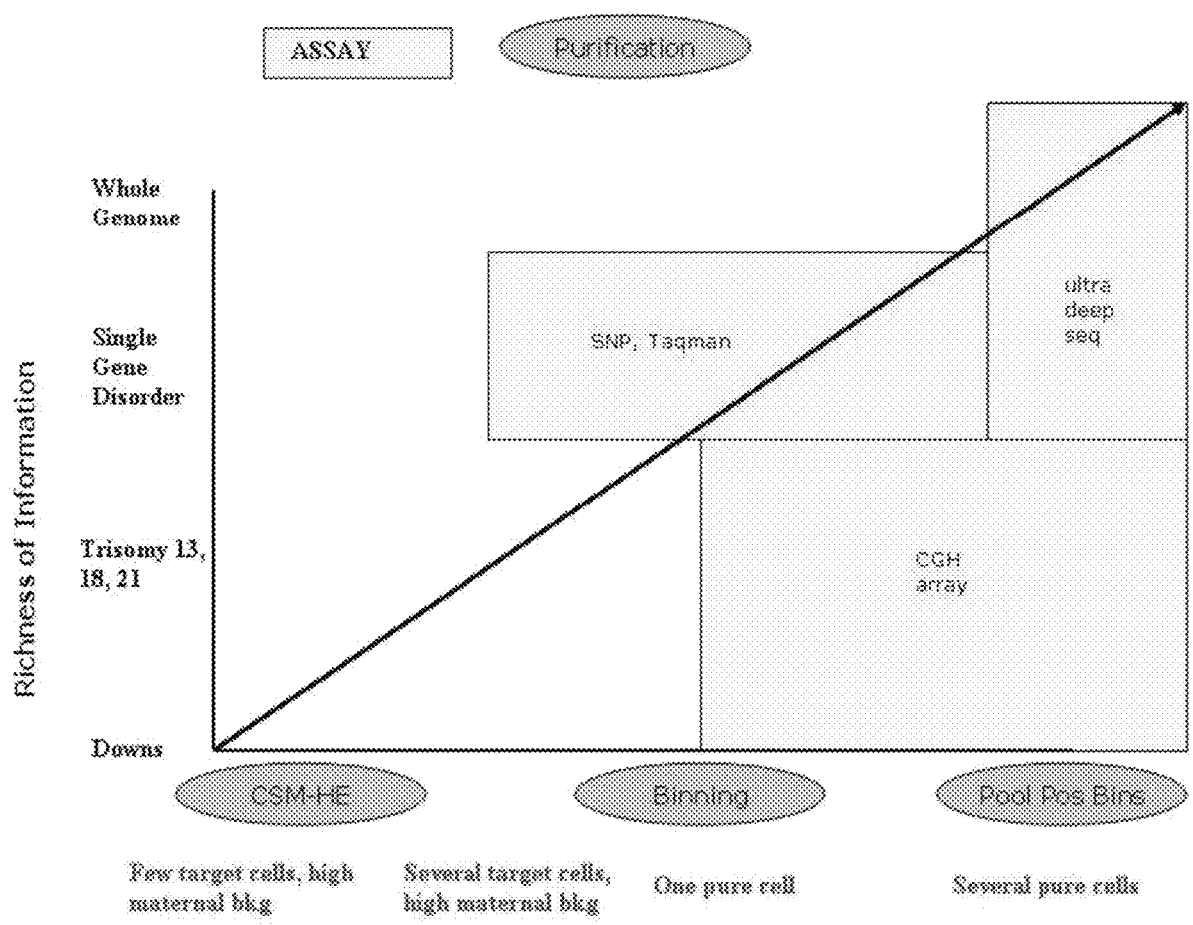
FIG. 16 illustrates assays that can produce information on the presence of aneuploidy and other genetic disorders in target cells. Information on anueploidy and other genetic disorders in target cells may be acquired using technologies such as: (1) a CGH array established for chromosome counting, which can be used for aneuploidy determination and/or detection of intra-chromosomal deletions; (2) SNP/taqman assays, which can be used for detection of single nucleotide polymorphisms; and (3) ultra-deep sequencing, which can be used to produce partial or complete genome sequences for analysis.

Expected results are shown in FIG. 14. Here, six of the 96 wells test positive for allele A, confirming the presence of cells of fetal origin, because the maternal genotype (BB) is known and cannot be positive for allele A. DNA from positive wells may be pooled for further analysis or analyzed individually.

Example 6: Use of Highly Parallel Genotyping and High Throughput Sequencing for Fetal Diagnosis Fetal cells or nuclei can be isolated as described in the enrichment section or as described in example 1. The enrichment process described in example 1 may generate a final mixture containing approximately 500 maternal white blood cells (WBCs), approximately 100 maternal nuclear red blood cells (mnBCs), and a minimum of approximately 10 fetal nucleated red blood cells (fnRBCs) starting from an initial 20 ml blood sample taken late in the first trimester. In the context of fetal diagnosis, it is very valuable to have a reference sample containing only the mother's genotype. When the diagnosis procedure is based on enriching for circulating fetal cells in the mother's blood, the reference sample can be created simply by not enriching for fetal cells, and then diluting enough to ensure that <<1 fetal cell is expected in the sample used as input to the SNP detection process. Alternatively, white blood cells can be selected, for which the circulating fetal fraction is negligible.

Perform Multiple Displacement Amplification (MDA): Current technologies and protocols for highly parallel SNP detection with DNA microarray readout result in inaccurate calls when there are too few starting DNA copies or when a particular allele represents a small fraction in the population of input DNA molecules. In the methods described herein a ratio-preserving pre-amplification of the DNA, such as multiple displacement amplification, is done to provide enough copies to support accurate SNP detection via primer extension ligation methods described below. This pre-amplification method is chosen to produce as close as possible the same amplification factor for all target regions of the genome.

Multiple displacement amplification protocols can be performed as described in Gonzalez et al. Environmental Microbiology 7(7) 1024-1028, (2005). Briefly, samples are suspended in 100 ul 10 mM Tris-HCl buffer (pH 7.5). Cells are lysed by adding 100 ul of alkaline lysis solution (400 mM KOH, 100 mM DTT, 10 mM EDTA) and incubating cells for 10 min on ice. Lysed cells are neutralized with 100 µl of neutralization solution (2 ml 1 M HCl and 3 ml 1 M Tris-HCl). Lysed cells are used directly as template in MDA and PCR reactions.

1 µl template DNA in 9 µl sample buffer (50 mM Tris-HCl, (pH 8.2), 0.5 mM EDTA) containing random hexamers is denatured at 95° C. for 3 min and placed on ice. Buffer (9 µl) containing dNTPs and 1 µl enzyme mix containing Φ29 DNA polymerase are added to the 10 µl of denatured DNA template-random hexamers solution and incubated at 30° C. for 6 h. A final incubation at 65° C. for 10 min inactivated the Φ29 DNA polymerase.

Highly Parallel Genotyping: Highly parallel SNP detection can be used to obtain information about genotype and gene copy numbers at a large number of loci scattered across the genome, in one procedure. Highly parallel SNP genotyping can be performed as described in Fan et al. Cold Spring Harb Symp Quant Biol; 68: 69-78, (2003). Genomic DNA is immobilized to streptavidin-coated magnetic beads by mixing 20 µl of DNA (100 ng/µl) with 5 µl of photobiotin (0.2 µg/µl) and 15 µl of mineral oil, and incubating at 95° C. for 30 minutes. Trizma base (25 µl of 0.1 M) is added, followed by two extractions with 75 µl of Sec-butanol to remove unreacted photobiotin. The extracted gDNA (20 µl) is then mixed with 34 µl of Paramagnetic Particle A Reagent (MPA; Illumina) and incubated at room temperature for 90 minutes. The immobilized gDNA is then washed twice with DNA wash buffer (WDI) (Illumina) and resuspended at 10 ng/µl in WDI. In each subsequent reaction, 200 ng (10 µl) of DNA is used.

Assay oligonucleotides are then annealed to the genomic DNA by combining the immobilized DNA (10 µl) with annealing reagent (MAI; Illumina; 30 µl) and SNP-specific oligonucleotides (10 µl) containing 25 nM of each oligonucleotide) to a final volume of 50 µl. LSOs are synthesized with a 5' phosphate to enable ligation. Annealing is carried out by ramping temperature from 70° C. to 30° C. over ~8 hours, then holding at 30° C. until the next processing step.

After annealing, excess and mishybridized oligonucleotides are washed away, and 37 µl of master mix for extension (MME; Illumina) is added to the beads. Extension is carried out at room temperature for 15 minutes. After washing, 37 µl of master mix for ligation (MML; Illumina) is added to the extension products, and incubated for 20 minutes at 57° C. to allow the extended upstream oligo to ligate to the downstream oligo.

The extension products are then amplified by PCR. After extension and ligation, the beads are washed with universal buffer 1 (UB 1; Illumina), resuspended in 35 μl of elution buffer (IPI; Illumina) and heated at 95° C. for one minute to release the ligated products. The supernatant is then used in a 60-μl PCR. PCR reactions are thermocycled as follows: 10 seconds at 25° C.; 34 cycles of (35 seconds at 95° C., 35 seconds at 56° C., 2 minutes at 72° C.); 10 minutes at 72° C.; and cooled to 4° C. for 5 minutes. The three universal PCR primers (PI, P2, and P3) are labeled with Cy3, Cy5, and biotin, respectively.

High throughput sequencing: After the SNP-specific ligation-extension reaction, and amplification of the products, readout of the SNP types can be done using high throughput sequencing as described in Margulies et al. Nature 437 376-380, (2005). Briefly, the amplicons are diluted and mixed with beads such that each bead captures a single molecule of the amplified material. The DNA-carrying beads are isolated in separate 100 urn aqueous droplets made through the creation of a PCR-reaction-mixture-in-oil emulsion. The DNA molecule on each bead is then amplified to generate millions of copies of the sequence, which all remain bound to the bead. Finally, the beads are placed into a highly parallel sequencing-by-synthesis machine which can generate over 400,000 sequence reads (~100 bp per read) in a single 4 hour run.

Fetal Diagnosis: The SNP data obtained from the high throughput sequencing is analyzed for fetal diagnosis using the methods described in Example 9.

Example 7: Use of Highly Parallel Genotyping and Bead Arrays for Fetal Diagnosis Fetal cells or nuclei can be isolated as described in the enrichment section or as described in example 1. The enrichment process described in example 1 may generate a final mixture containing approximately 500 maternal white blood cells (WBCs), approximately 100 maternal nuclear red blood cells (mnBCs), and a minimum of approximately 10 fetal nucleated red blood cells (fnRBCs) starting from an initial 20 ml blood sample taken late in the first trimester. In the context of fetal diagnosis, it is very valuable to have a reference sample containing only the mother's genotype. When the diagnosis procedure is based on enriching for circulating fetal cells in the mother's blood, the reference sample can be created simply by not enriching for fetal cells, and then diluting enough to ensure that <<1 fetal cell is expected in the sample used as input to the SNP detection process. Alternatively, white blood cells can be selected, for which the circulating fetal fraction is negligible.

Perform Linear Amplification of Genomic DNA: Current technologies and protocols for highly parallel SNP detection with DNA microarray readout result in inaccurate calls when there are too few starting DNA copies or when a particular allele represents a small fraction in the population of input DNA molecules. In the methods described herein a ratio-preserving pre-amplification of the DNA, such as linear amplification of genomic DNA, is done to provide enough copies to support accurate SNP detection via primer extension ligation methods described below. This pre-amplification method is chosen to produce as close as possible the same amplification factor for all target regions of the genome.

Linear amplification protocols can be performed as described in Liu et al. BMC Genomics 4(1) 19-30 (2003). This protocol uses a terminal transferase tailing step and second strand synthesis to incorporate T7 promoters at the ends of the DNA fragments prior to in vitro transcription (IVT). Briefly, genomic DNA can be obtained either by ChIP or by restriction digests. ChIP DNA is fragmented by sonication and isolated using antibody against di-methyl-H3 K4. Restricted genomic DNA is prepared as follows: genomic DNA isolated by bead lysis, phenol/chloroform extraction, and ethanol precipitation, is restricted either with Mu I or with Rsa I (New England BioLabs (NEB)). Digested products then undergo electrophoresis on a 2% agarose gel. Restriction fragments in the 100-700 bp size range are excised from the gel and purified using the QIAquick Gel Extraction Kit (Qiagen).

Calf intestinal alkaline phosphatase (CIP) (NEB) is used to remove 3' phosphate groups from DNA samples prior to IVT. Up to 500 ng DNA is incubated with 2.5 U enzyme in a 10 μl volume with the supplied buffer at 37° C. for 1 hour. The reaction was cleaned up with the MinElute Reaction Cleanup Kit (Qiagen) per manufacturer instructions except that the elution volume is increased to 20 μl.

PolyT tails are generated using terminal transferase (TdT) as follows. Up to 50 ng of CIP-treated template DNA is incubated for 20 minutes at 37° C. in a 10 μl solution containing 20 U TdT (NEB), 0.2 M potassium cacodylate, 25 mM Tris-HCl pH 6.6, 0.25 mg/ml BSA, 0.75 mM $CoCl_2$, 4.6 μM dTTP and 0.4 μM ddCTP. The reaction is halted by the addition of 2 μl of 0.5 M EDTA pH 8.0, and product isolated with the MinElute Reaction Cleanup Kit (Qiagen), increasing the elution volume to 20 μl.

Second strand synthesis and incorporation of the T7 promoter sequence is carried out as follows: the 20 μl tailing reaction product is mixed with 0.6 μl of 25 μM T7-A18B primer (5'-CATTAGCGGCCGCGAAATTAATACGACT-CACTATAGGGAG(A)18 [B], where B refers to C, G or T, SEQ ID NO: 9), 5 μl 10×EcoPol buffer (100 mM Tris-HCl pH 7.5, 50 mM MgCl2, 75 mM dTT), 2 μl 5.0 mM dNTPs, and 20.4 μl nuclease-free water. In experiments with 10-50 ng starting material, the end primer concentration is kept at 300 nM, while the reaction volume is scaled down to maintain an end concentration of 1 ng/ul starting material. For starting amounts less than 10 ng, the volume is kept at 10 μl. If necessary, volume reduction of the eluate from the TdT tailing is performed in a vacuum centrifuge on medium heat. Samples are incubated at 94° C. for 2 minutes to denature, ramped down at −1 C.°/sec to 35° C., held at 35° C. for 2 minutes to anneal, ramped down at −0.5 C.°/sec to 25° C. and held while Klenow enzyme is added (NEB) to an end concentration of 0.2 U/μl. The sample is then incubated at 37° C. for 90 minutes for extension. The reaction is halted by addition of 5 μL 0.5 M EDTA pH 8.0 and product is isolated with the MinElute Reaction Cleanup Kit (Qiagen), increasing the elution volume to 20 μL.

Prior to in vitro transcription, samples are concentrated in a vacuum centrifuge at medium heat to 8 μl volume. The in vitro transcription is performed with the T7 Megascript Kit (Ambion) per manufacturer's instructions, except that the 37° C. incubation is increased to 16 hours. The samples are purified with the RNeasy Mini Kit (Qiagen) per manufacturer's RNA cleanup protocol, except with an additional 500 μL, wash with buffer RPE. RNA is quantified by absorbance at 260 nm, and visualized on a denaturing 1.25×MOPS-EDTA-Sodium Acetate gel.

Highly Parallel Genotyping: Highly parallel SNP detection can be used to obtain information about genotype and gene copy numbers at a large number of loci scattered across the genome, in one procedure. Highly parallel SNP genotyping can be performed as described in Example 6.

Bead Array: After the SNP-specific ligation-extension reaction, and amplification of the products, readout of the SNP types can be done using bead arrays as described in Shen at al. Mutation Research 573 70-82, (2005). Double-stranded PCR products are immobilized onto paramagnetic particles by adding 20 µl of Paramagnetic Particle B Reagent (MPB; Illumina) to each 60-µl PCR, and incubated at room temperature for a minimum of 60 minutes. The bound PCR products are washed with universal buffer 2 (UB2; Illumina), and denatured by adding 30 µl of 0.1 N NaOH. After one minute at room temperature, 25 µl of the released ssDNAs is neutralized with 25 µl of hybridization reagent (MH I: Illumina) and hybridized to arrays.

Arrays are hydrated in UB2 for 3 minutes at room temperature, and then preconditioned in 0.1 N NaOH for 30 seconds. Arrays are returned to the UB2-reagent for at least 1 minute to neutralize the NaOH. The pretreated arrays are exposed to the labeled ssDNA samples described above. Hybridization is conducted under a temperature gradient program from 60° C. to 45° C. over −12 hours. The hybridization is held at 45° C. until the army is processed. After hybridization, the arrays are first rinsed twice in UB2 and once with ISI (ISI; Illumina) at room temperature with mild agitation, and then imaged at a resolution of 0.8 microns using a BeadArray Reader (Illumina). PMT settings are optimized for dynamic range, channel balance, and signal-to-noise ratio. Cy3 and Cy5 dyes are excited by lasers emitting at 532 nm and 635 nm, respectively.

The automatic calling of genotypes is performed by genotype calling software (GenCall) genotyping software, using a Bayesian model, which compared intensities between probes for allele A and allele B across a large number of samples to create archetypal clustering patterns. These patterns allowed the genotyping data to be assigned membership to clusters using a probabilistic model and allowed assignment of a corresponding GenCall score. For example, data points falling between two clusters are assigned a low probability score of being a member of either cluster and had a correspondingly low GenCall score. The cluster quality can be assessed by evaluating the CSS, a measure of statistical separation between clusters. It is defined as $$CSS = \min\left(\frac{|\theta_{AB} - \theta_{AA}|}{|\sigma_{AB} + \sigma_{AA}|}, \frac{|\theta_{AB} - \theta_{BB}|}{|\sigma_{AB} + \sigma_{BB}|}\right).$$

Loci with cluster scores around the cutoff of 3.0 are visually evaluated and the training clusters refined by manual intervention. A cutoff value of 3.0 can be chosen for the CSS on the basis of minimizing strand concordance errors. Loci with questionable clusters are scored as unsuccessful and excluded from further analysis.

Fetal Diagnosis: The SNP data obtained from the bead array assay is analyzed for fetal diagnosis using the methods described in Example 9.

Example 8: Use of Highly Parallel Genotyping and DNA Arrays for Fetal Diagnosis

Fetal cells or nuclei can be isolated as described in the enrichment section or as described in example 1. The enrichment process described in example 1 may generate a final mixture containing approximately 500 maternal white blood cells (WBCs), approximately 100 maternal nuclear red blood cells (mnBCs), and a minimum of approximately 10 fetal nucleated red blood cells (fnRBCs) starting from an initial 20 ml blood sample taken late in the first trimester. In the context of fetal diagnosis, it is very valuable to have a reference sample containing only the mother's genotype. When the diagnosis procedure is based on enriching for circulating fetal cells in the mother's blood, the reference sample can be created simply by not enriching for fetal cells, and then diluting enough to ensure that <<1 fetal cell is expected in the sample used as input to the SNP detection process. Alternatively, white blood cells can be selected, for which the circulating fetal fraction is negligible.

Perform Multiple Displacement Amplification: Current technologies and protocols for highly parallel SNP detection with DNA microarray readout result in inaccurate calls when there are too few starting DNA copies or when a particular allele represents a small fraction in the population of input DNA molecules. In the methods described herein a ratio-preserving pre-amplification of the DNA, such as multiple displacement amplification, is done to provide enough copies to support accurate SNP detection via primer extension ligation methods described below. This pre-amplification method is chosen to produce as close as possible the same amplification factor for all target regions of the genome. Multiple displacement amplification protocols can be performed as described in Example 6.

Highly Parallel Genotyping: Highly parallel SNP detection can be used to obtain information about genotype and gene copy numbers at a large number of loci scattered across the genome, in one procedure. Highly parallel SNP genotyping can be performed as described in Example 6.

DNA Array: After the SNP-specific ligation-extension reaction, and amplification of the products, readout of the SNP types can be done using DNA arrays as described in Gunderson et al. Nature Genetics 37(5) 549-554, (2005). The army data can be obtained using Illumina's Sentrix BeadArray matrix. Oligonucleotide probes on the beads are 75 bases in length; 25 bases at the 5' end are used for decoding and the remaining 50 bases are locus-specific. The oligonucleotides are immobilized on activated beads using a 5' amino group. The army can contain probes for SNP assays (probe pairs, allele A and allele B).

The amplification products of the SNP-specific ligation-extension reaction are denatured at 95° C. for 5 min and then exposed it to the Sentrix array matrix, which is mated to a microtiter plate, submerging the fiber bundles in 15 ml of hybridization sample. The entire assembly is incubated for 14-18 h at 48° C. with shaking. After hybridization, arrays are washed in 1× hybridization buffer and 20% formamide at 48 IC for 5 min.

Allele Specific Primer Extension (ASPE) can be used to score SNPs. Before carrying out the array-based primer extension reaction, Sentrix array matrices are washed for 1 min with wash buffer (33.3 mM NaCl, 3.3 mM potassium phosphate and 0.1% Tween-20, pH 7.6) and then incubated for 15 min in 50 µl of ASPE reaction buffer (Illumina EMM, containing polymerase, a mix of biotin-labeled and unlabeled nucleotides, single-stranded binding protein, bovine serum albumin and appropriate buffers and salts) at 37° C. After the reaction, the arrays are immediately stripped in freshly prepared 0.1 N NaOH for 2 min and then washed and neutralized twice in 1× hybridization buffer for 30 s. The biotin-labeled nucleotides incorporated during primer extension using a sandwich assay is then detected as described in Pinkel et al. PNAS 83 (1986) 2934-2938. The arrays are blocked at room temperature for 10 min in 1 mg ml$^{-1}$ bovine serum albumin in 1× hybridization buffer and then washed for 1 min in 1× hybridization buffer. The arrays are then stained with streptavidin-phycoerythrin solution (1× hybridization buffer, 3 µg ml$^{-1}$ streptavidin-phycoerythrin (Molecular Probes) and 1 mg ml$^{-1}$ bovine serum albumin) for 10 min at room temperature. The arrays are washed with 1× hybridization buffer for 1 min and then counterstained them with an antibody reagent (10 mg ml$^{-1}$ biotinylated antibody to streptavidin (Vector Labs) in 1×PBST (137 mM NaCl, 2.7 mM KCl, 4.3 mM sodium phosphate, 1.4 mM potassium phosphate and 0.1% Tween-20) supplemented with 6 mg ml$^{-1}$ goat normal serum) for 20 min. After counterstaining, the arrays are washed in 1× hybridization buffer and restrained them with streptavidin-phycoerythrin solution for 10 min. The arrays are washed one final time in 1× hybridization buffer before imaging them in 1× hybridization buffer on a custom CCD-based BeadArray imaging system. The intensities are extracted intensities using custom image analysis software.

The automatic calling of genotypes is performed by genotype calling software (GenCall) genotyping software as described in example 7.

Fetal Diagnosis: The SNP data obtained from the DNA array assay is analyzed for fetal diagnosis using the methods described in Example 9.

Example 9: Fetal Diagnosis

Results obtained in Example 6, 7, and 8 can be used for fetal diagnosis.

A model for SNP data in the context of fetal diagnosis is given in Equations 1-3. A normal (diploid) fetus will result in data xk at locus k $$x_k = A_k[(m_{k1} + m_{k2}) + f(m_{k1} \text{ or } m_{k2}) + p_k)] + \text{residual} \quad (1)$$

A trisomy caused by maternal non-dysjunction would be represented by $$x_k = A_k[(m_{k1} + m_{k2}) + f(m_{k1} + m_{k2} + p_k)] + \text{residual} \quad (2)$$

and a paternally inherited trisomy would be represented by $$x_k = A_k[(m_{k1} + m_{k2}) + f((m_{k1} \text{ or } m_{k2}) + p_{k1} + p_{k2})] + \text{residual} \quad (3)$$

In Equations 1-3, $A_k$ denotes a scale factor which subsumes the efficiencies of amplification, hybridization, and readout common to the alleles at locus k. In this model amplification differences between different primer pairs are fitted and do not appear in the residuals. Alternatively, a single A parameter could be used and the residuals would reflect these differences. f represents the fraction of fetal cells in the mixture, $m_{k1}$ and $m_{k2}$ denote the maternal alleles at locus k, and $p_k$ denotes the paternal allele at locus k. The allele symbols actually represent unit data contributions that can be arithmetically summed; e.g., $m_{k1}$ might be a detection of the 'C' genotype represented by unit contribution to the 'C' bin at that locus.

FIG. 6 illustrates the kinds of SNP calls that result under this data model. At Locus 1, the fetal genotype was GC. There is a paternally inherited 'G' allele contribution in the mixed sample that results in an increase of G signal above the noise level observed in the maternal-only sample, and a maternally inherited 'C' allele contribution that increases the C signal. The effective value off that has been assumed in these illustrations is f=0.2. At Locus 2, the paternal allele is 'T'. At Locus 3, the fetus is homozygous GG. In the third row of FIG. 6, the effect of a fetal trisomy is represented by the dashed red lines, superposed on a normal (diploid) mixed-sample pattern. The trisomy is assumed to include Loci 1 and 2, but not Loci 3 and 4. At Loci 1 and 2 both maternal allele strengths are increased in the mixed sample, as well as the separate paternal allele contribution. At Locus 3, it was assumed that the fetus was GG' and the paternal allele is the same as the first maternal allele. Note that the ratio between the average of the two maternal alleles and the paternal allele will be slightly greater at Loci 1 and 2 than at Locus 4—this is one indicator of trisomy.

Simple, Suboptimal Detection Methods

A simple intuitive understanding of the effect of trisomy is that it increases the abundances of fetal alleles at loci within the affected region. Trisomies are predominately from maternal non-disjunction events, so typically both maternal alleles, and a single paternal allele, are increased, and the ratio of maternal allele abundance to paternal allele abundance is higher in the trisomic region. These signatures may be masked by differences in DNA amplification and hybridization efficiency from locus to locus, and from allele to allele.

Within a locus, the PCR differences are smaller than between loci, because the same primers are responsible for all the different allele amplicons at that locus. Therefore, the allele ratios may be more stable than the overall allele abundances. This can be exploited by identifying loci where the paternal allele is distinct form the maternal allele and taking the ratio of the paternal allele strength to the average of the maternal allele strengths. These allele ratios then can be averaged over the hypothesized aneuploidy region and compared to the average over a control region. The distributions of these ratio values in the hypothesized aneuploidy region and in the control region can be compared to create an estimate of statistical significance for the observed difference in means. A simple example of this procedure would use Student's t-test.

Alternatively, the maternal allele strengths over the suspected aneuploid region can be compared to those in the control region, all without forming any ratios to paternal alleles. In this approach, errors in the measurement of the paternal allele abundances do not enter; however, the differences in amplification efficiency between primer pairs do enter, and these typically will be larger than differences between alleles in the same locus. In this approach there also may be a residual bias between the efficiencies averaged over certain chromosomes; therefore it may be useful to perform the entire detection process resulting in an observed abundance ratio for the mixed sample, do it also for the maternal sample, and then take the ratio of ratios. This ratio of ratios will be free of the chromosome bias; however, it will include errors in the measurements of the maternal sample.

Because the fraction of fetal cells can be small or even zero, the aneuploidy signal (the departure of the observed ratio from unity) may be weak even when fetal aneuploidy is present. An independent estimate of the fetal cell fraction, including a confidence estimate of whether measurable fetal DNA is present at all, is useful in interpreting the observed aneuploidy ratios. FIG. 7 illustrates allele signals re-ordered by rank. Assuming the mother has no more than two alleles at each locus, the magnitude of the third ranked allele is potentially a robust indicator of the presence of fetal DNA. Although measurement errors can artificially inflate the size of the third and fourth alleles, it is very unlikely to result in a bimodal distribution for the relative magnitude of the third allele with respect to the first two. Such a bimodal distribution is cartooned in FIG. 8 The secondary peak of this distribution occurs at a value approximately equal to the fraction of fetal cells. This is one way to determine the value of the variable fin the data model. The statistical confidence that the bimodality is real can be used to assign a confidence that fetal DNA was present in the mixed sample. Statistical tests for bimodality are discussed in MY Cheng and P Hall,

*J.R. Statist.* Soc. B (1998), 60 (Part 3) pp579-589, and these authors prefer bootstrap based methods. Only if this confidence exceeds a threshold, say 99.9%, would an aneuploidy call be attempted. This threshold needs to be quite stringent to avoid the expensive mistake of declaring a fetus normal when in fact it is not. The estimated fetal cell fraction can be used to interpret the aneuploidy statistic: a large value of f and an observed aneuploidy ratio very close to unity would suggest no aneuploidy; a small value of f along with an aneuploidy ratio approximately equal to 1+f/2 would suggest trisomy, but it is still necessary to decide whether the observed aneuploidy is significantly different from unity and this requires an error model. A simple robust estimate of the error distribution could come from repeated processing of nominally identical samples.

Fitting of Data to the Model for Optimal Detection of Aneuploidy

The data model can be used to simultaneously recover estimates of the fraction of fetal cells, and efficient detection of aneuploidies in hypothesized chromosomes or chromosomal segments. This integrated approach should result in more reliable and sensitive declarations of aneuploidy.

Equations 1-3 actually represent five different models because of the ambiguity between $m_{k1}$ and $m_{k2}$ in the last term of Equations 1 and 3. Testing for aneuploidy of Chromosomes 13, 18, and 21 then would entail 5×5×5=125 different model variants that would be fit to the data.

The parameter values for the maternal allele identities are taken from the results for the maternal-only sample and the remaining parameters are fit to the data from the mixed sample. Because the number of parameters is very large when the number of loci is large, a global optimization requires iterative search techniques. One possible approach is to do the following for each model variant i) Set f to 0 and solve for $A_k$ at each locus.
ii) Set f to a value equal to the smallest fetal/maternal cell ratio for which fetal cells are likely to be detectable.
iii) Solve for paternal allele(s) identities and strengths at each locus, one locus at a time, that minimize data-model residuals.
iv) Fix the paternal alleles and adjust f to minimize residuals over all the data.
v) Now vary only the $A_k$ to minimize residuals. Repeat iv and v until convergence.
vi) Repeat iii through v until convergence.

The best overall fit of model to data is selected from among all the model variants. The best overall fit yields the values off and $A_k$ we will call $A_{kmax}$. The likelihood of observing the data given $f_{kmax}$ can be compared to the likelihood given f=0. The ratio is a measure of the amount of evidence for fetal DNA. A typical threshold for declaring fetal DNA would be a likelihood ratio of ~1000 or more. The likelihood calculation can be approximated by a more familiar Chi-squared calculation involving the sum of squared residuals between the data and the model, where each residual is normalized by the expected rms error. This Chi-squared is a good approximation to the Log(likelihood) to the extent the expected errors in the data are Gaussian additive errors, or can be made so by some amplitude transformation of the data.

If based on the above determination of likelihood ratio it is decided that fetal DNA is not present, then the test is declared to be non-informative. If it is decided that fetal DNA is present, then the likelihoods of the data given the different data model types can be compared to declare aneuploidy. The likelihood ratios of aneuploid models (Equations 2 and 3) to the normal model (Equation 1) are calculated and these ratios are compared to a predefined threshold. Typically this threshold would be set so that in controlled tests all the trisomic cases would be declared aneuploid, and so that it would be expected that the vast majority (>99.9%) of all truly trisomic cases would be declared aneuploid by the test. Given a limited patient cohort size for test validation, one strategy to accomplish approximately the 99.9% detection rate is to increase the likelihood ratio threshold beyond that necessary to declare all the known trisomic cases in the validation set by a factor of 1000/N, where N is the number of trisomy cases in the validation set.

Error Modeling

The data contain small additive errors associated with the readout technology, multiplicative errors associated with DNA amplification and hybridization efficiencies being different from locus to locus and from allele to allele within a locus, and errors associated with imperfect specificity in the process. By including the many parameters $A_k$ in the model, rather than a single scale parameter, the residuals will include allele-to-allele efficiency differences but not locus to locus differences. These tend to be multiplicative errors in the resulting observed allele strengths heights; i.e. two signals may be 20% different in strength although the starting concentrations of the alleles were identical. As a first approximation we can assume errors are random from allele to allele, and have relatively small additive errors, and larger Poisson and multiplicative error components. The magnitudes of these error components can be estimated from repeated processing of identical samples. The Chi-square residuals calculation for any data-model fit then can be supported with these modeled squared errors for any peak height or data bin.

Alternatively, when using a single A parameter, the residuals will be larger and will contain a component which is correlated between alleles at the same locus. Calculation of likelihood will need to take this correlation into account.

What is claimed is:

1. A method for determining a ratio of signal intensities of amplification products for a maternal allele in a first genomic region on a first chromosome suspected of being aneuploid and for a maternal allele in a second genomic region on a second chromosome that is not aneuploid or not suspected of being aneuploid in a mixed sample comprising a mixture of fetal and maternal cells, the method comprising:
   a. enriching the mixed sample for fetal cells to produce an enriched sample comprising fetal and maternal cells having an increased concentration of fetal cells relative to maternal cells before enrichment, and lysing cells in the enriched sample to obtain genomic DNA (gDNA);
   b. hybridizing probes to each of a plurality of loci in the gDNA on at least two different chromosomes to produce hybridized probes;
   c. ligating the hybridized probes at each locus to each other to create an amplification template specific to each locus;
   d. amplifying the amplification template specific to each locus to create amplification products;
   e. hybridizing the amplification products to probes on a microarray; and
   f. detecting, among the amplification products hybridized to probes on the microarray, a first signal intensity of the amplification products for a maternal allele in a first genomic region on a first chromosome suspected of being aneuploid and a second signal intensity of the amplification products for a maternal allele in a second genomic region on a second chromosome that is not aneuploid or not suspected of being aneuploid, and determining a ratio of the first signal intensity to the second signal intensity.

2. The method of claim 1, wherein the mixed sample comprises a maternal blood sample from a pregnant woman within a first or second trimester.

3. The method of claim 1, further comprising attaching the gDNA to a solid support.

4. The method of claim 3, wherein the solid support comprises a paramagnetic particle.

5. The method of claim 3, wherein the solid support comprises streptavidin.

6. The method of claim 3, wherein the gDNA is biotin-labeled.

7. The method of claim 1, wherein three oligonucleotide probes are provided for each locus.

8. The method of claim 1, wherein the gDNA is attached to a particle and the ligation occurs while the gDNA is attached to the particle, thereby forming an amplification template annealed to the gDNA attached to the particle.

9. The method of claim 8, further comprising releasing the amplification template from the gDNA attached to the particle.

10. The method of claim 1, wherein the amplification template comprises universal polymerase chain reaction (PCR) primer sites and the amplification comprises hybridization of universal primers to the universal PCR primer sites.

11. The method of claim 1, wherein the microarray is a DNA microarray.

* * * * *